(12) United States Patent
Clapp et al.

(10) Patent No.: US 11,393,159 B2
(45) Date of Patent: *Jul. 19, 2022

(54) METHODS AND APPARATUS FOR EFFICIENTLY RENDERING, MANAGING, RECORDING, AND REPLAYING INTERACTIVE, MULTIUSER, VIRTUAL REALITY EXPERIENCES

(71) Applicant: Colorado State University Research Foundation, Fort Collins, CO (US)

(72) Inventors: Tod Robert Clapp, Fort Collins, CO (US); Brendan Garbe, Fort Collins, CO (US); Chad Eitel, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/178,073

(22) Filed: Feb. 17, 2021

(65) Prior Publication Data
US 2022/0012936 A1 Jan. 13, 2022

Related U.S. Application Data

(63) Continuation of application No. 16/842,009, filed on Apr. 7, 2020, now Pat. No. 10,930,055, which is a
(Continued)

(51) Int. Cl.
G06T 19/00 (2011.01)
G06T 19/20 (2011.01)
(Continued)

(52) U.S. Cl.
CPC ............ G06T 15/08 (2013.01); G02B 27/017 (2013.01); G06T 1/60 (2013.01); G06T 7/0012 (2013.01);
(Continued)

(58) Field of Classification Search
None
See application file for complete search history.

(56) References Cited

U.S. PATENT DOCUMENTS

2004/0122310 A1 6/2004 Lim
2008/0055305 A1 3/2008 Blank et al.
(Continued)

FOREIGN PATENT DOCUMENTS

WO  WO 2018/093921 A1  5/2018

OTHER PUBLICATIONS

International Search Report and Written Opinion of the International Searching Authority for International Application No. PCT/US2019/039576 dated Oct. 9, 2019.

*Primary Examiner* — Joni Hsu
(74) *Attorney, Agent, or Firm* — Cooley LLP

(57) ABSTRACT

In some embodiments, an apparatus includes a volatile memory, a non-volatile memory, a first processor coupled to the non-volatile memory and configured to receive a data set associated with an object and user information associated with a spatial position of a user in a multi-user virtual (IMVR) environment, and a second processor coupled to the volatile memory, the second processor configured to render an instance of the portion of the object in the IMVR environment from a perspective of the user based on the spatial position of the user. The first processor is configured to generate a look-up table (LUT) based on a set of inputs received from a user. The second processor is configured to render, based on the LUT and information related to a manipulation by a user, an updated instance of the portion of the object that manifests an effect of the manipulation in the IMVR environment.

15 Claims, 57 Drawing Sheets

Related U.S. Application Data continuation of application No. PCT/US2019/039576, filed on Jun. 27, 2019.

(60) Provisional application No. 62/690,879, filed on Jun. 27, 2018, provisional application No. 62/690,880, filed on Jun. 27, 2018.

(51) Int. Cl.
    *G06T 15/08*      (2011.01)
    *G06T 1/60*      (2006.01)
    *G06T 7/00*      (2017.01)
    *G02B 27/01*      (2006.01)

(52) U.S. Cl.
    CPC ............ *G06T 19/006* (2013.01); *G06T 19/20* (2013.01); *G02B 2027/014* (2013.01); *G06T 2207/10081* (2013.01); *G06T 2207/10088* (2013.01)

(56) References Cited

U.S. PATENT DOCUMENTS

| | | |
|---|---|---|
| 2015/0029092 A1 | 1/2015 | Holz et al. |
| 2016/0019718 A1 | 1/2016 | Mukkamala et al. |
| 2017/0064211 A1 | 3/2017 | Omid-Zohoor |
| 2017/0075813 A1 | 3/2017 | Kaburaki |
| 2017/0236496 A1* | 8/2017 | Saito ................. B60K 37/02 345/531 |
| 2017/0289533 A1 | 10/2017 | Ono |
| 2017/0293995 A1 | 10/2017 | Saleh et al. |
| 2018/0018792 A1 | 1/2018 | Ballard et al. |
| 2018/0168780 A1 | 6/2018 | Kopelman et al. |
| 2018/0247449 A1 | 8/2018 | Park et al. |
| 2018/0284914 A1 | 10/2018 | Yanai et al. |
| 2018/0357809 A1 | 12/2018 | Lawless et al. |
| 2019/0243599 A1 | 8/2019 | Rochford et al. |
| 2019/0279416 A1 | 9/2019 | Lee et al. |
| 2019/0347071 A1 | 11/2019 | Mackinnon, Jr. |
| 2020/0234487 A1 | 7/2020 | Clapp et al. |

* cited by examiner

```
using System.Collections;
using System.Collections.Generic;
using UnityEngine;
using UnityEngine.UI;

public class ModuleUI : MonoBehaviour { public GameObject playButton;
    public GameObject pauseButton;
    public GameObject stopButton;
    public GameObject recordButton;
    public string shortPathNoExtension;
    public Text txtRef;
    private bool activated;
    private bool recordableFile;

private ModulePlayer modulePlayer;

// Use this for initialization
    void Start () {
        Debug.Log("Module Interface Started.. .**");
        this.DisableButtons();
        this.modulePlayer = FindObjectOfType<ModulePlayer>();
        this.modulePlayer.TryBindToModule(this);
        this.SetPath(this.shortPathNoExtension, 1);
    } public void SetPath(string shortPathNoExtension, int recordable)
    {
        Debug.Log("(ModuleUI) shortPath: " + shortPathNoExtension);
        this.shortPathNoExtension = shortPathNoExtension;
        if(recordable == 0)
        {
            this.recordableFile = false;
        }
        else
        {
            this.recordableFile = true;
        }
        //this.recordableFile = recordable;
        this.InitializeButtons();
        this.txtRef.text = "Module: " + this*shortPathNoExtension;
    } private void DisableButtons()
    {
        Debug.Log("buttons disabled on module player...");
        this.playButton.SetActive(false);
        this.stopButton.SetActive(false);
        this.pauseButton.SetActive(false);
        this.recordButton.SetActive(false);
    }
```

FIG. 9A

```
private void InitializeButtons()
{
    Debug.Log("buttons initialized on module player..");
    this.playButton.SetActive(true);
    this.stopButton.SetActive(false);
    this.pauseButton.SetActive(false);
    if (!recordableFile)
    {
        this.recordButton.SetActive(false);
    }
    else
    {
        this.recordButton.SetActive(true);
    }
} public void Activate()
{
    this.activated = true;
    this.SetPath("temp", 1);
} public void Play()
{
    if (this.activated)
    {
        this.recordButton.SetActive(false);
        this.stopButton.SetActive(true);
        this.playButton.SetActive(false);
        this.pauseButton.SetActive(true);
        modulePlayer.TryPlayModule(this.shortPathNoExtension);
    }
} public void Record()
{
    Debug.Log("Record (ModuleUI) shortPathNoExtension: " + shortPathNoExtension);
    if (this.activated && this.recordableFile)
    {
        this.recordButton.SetActive(false);
        this.playButton.SetActive(false);
        this.pauseButton.SetActive(false);
        this.stopButton.SetActive(true);
        modulePlayer.Record(Application.persistentDataPath + shortPathNoExtension);
    }
} public void Pause()
{
    if (this.activated)
    {
        this.pauseButton.SetActive(false);
        this.playButton.SetActive(true);
        modulePlayer.PauseModule(true);
    }
} public void Stop()
{
    if (this.activated)
    {
        this.InitializeButtons();
        modulePlayer.StopModule(this.shortPathNoExtension);
    }
}
}
```

FIG. 9B

FIG. 29A  Exclusion Tool

When enabled, data within this 3D shape is skipped over by the rayMarch algorithm, effectively creating a "hollow" space where the shape exists within the volume See also FIG. 18

FIG. 29B  Inclusion Tool

When enabled, data outside this 3D shape is skipped over by the rayMarch algorithm, effectively creating a "filled" space where the shape exists within the volume See also FIG. 18

FIG. 30  CrossSection Tool

When enabled, the intersection of this plane and the volume cube creates an opaque image of the data intersected, effectively creating a 2D image/cross-section at any angle through the 3D volume.

FIG. 31A 

User is able to color voxels relative to the volume data voxels in a separate 3D texture. This texture is then added to the channels list and composited with the data during the rayMarch algorithm, effectively adding a customizable color/opacity on top of the data.

FIG. 31B 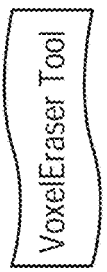

Building on the VoxelPainter Tool, "painted" Voxels of a specified value cause the rayMarch algorithm to skip compositing for that position in all channels, effectively creating an "empty" or "erased" space at the sampled position.

FIG. 31C 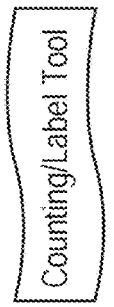

A user can choose points within the volume. These begin with a numbering system, but can be overwritten with any text chosen by the user.

FIG. 32A

MagicWand Tool

Building on the VoxelPainter Tool, the user selects a desired position in the volume, thus selecting a value from the underlying data voxels. This tool then systematically spreads from the chosen voxel and value to neighboring voxels with values within a desired "similarity" to the chosen value. This procedure continues to spread to additional neighboring voxels that are either (variant A) within the desired "similarity" to the initiating (neighbor) voxel OR (variant B) within the desired "similarity" to the initial chosen value.

All selected/spread to voxels are now considered "selected" and can be colored/erased at once

FIG. 32B

Directional MagicWand Tool

Similar to the MagicWand Tool, but is given an initial "forward" direction. The selection begins by spreading as far tangential to the "forward" direction initially, once complete, will spread in the forward direction, thus, will not spread "backwards"

MeshCreator Tool voxels that are selected or colored a specific color can be converted into a hollow mesh object and exported

FIG. 33A

Vessel Diameter Calculator

Using a method similar to the magic wand, spreads to neighboring voxels but in a strict spherical manor until sphere can't spread any larger, returns the diameter of the sphere

FIG. 33B

Key

+id: uint
+color: Color
+uv: Vector2

Event Overview

| SerializableEvent |
|---|
| +timeStamp: float |

| UserPose: SerializableEvent |
|---|
| +playerID: int |
| +hmdPosition: Vector3 |
| +hmdRotation: Quaternion |
| +leftControllerPosition: Vector3 |
| +leftControllerRotation: Quaternion |
| +rightControllerPosition: Vector3 |
| +rightControllerRotation: Quaternion |

| ObjectInterpolation: SerializableEvent |
|---|
| +position: Vector3 |
| +pivot: Vector3 |
| +rotation: Quaternion |

| ButtonEvent: SerializableEvent |
|---|
| +buttonID: int |

FIG. 44A

METHODS AND APPARATUS FOR EFFICIENTLY RENDERING, MANAGING, RECORDING, AND REPLAYING INTERACTIVE, MULTIUSER, VIRTUAL REALITY EXPERIENCES

CROSS-REFERENCE TO RELATED APPLICATIONS

This application is a continuation of U.S. application Ser. No. 16/842,009, filed Apr. 7, 2020 and titled "METHODS AND APPARATUS FOR EFFICIENTLY RENDERING, MANAGING, RECORDING, AND REPLAYING INTERACTIVE, MULTIUSER, VIRTUAL REALITY EXPERIENCES", now U.S. Pat. No. 10,930,055, which is a continuation of International Patent Application No. PCT/US2019/039576, filed on Jun. 27, 2019 and titled "METHODS AND APPARATUS FOR EFFICIENTLY RENDERING, MANAGING, RECORDING, AND REPLAYING INTERACTIVE, MULTIUSER, VIRTUAL REALITY EXPERIENCES", which claims priority to and the benefit of U.S. Provisional App. No. 62/690,879, filed on Jun. 27, 2018 and titled "Methods and Apparatus for Efficiently Rendering, Managing, Recording, and Replaying Interactive, Multiuser, Virtual Reality Experiences", and U.S. Provisional App. No. 62/690,880, also filed on Jun. 27, 2018 and titled "Methods and Apparatus for Efficiently Rendering, Managing, Recording, and Replaying Interactive, Multiuser, Virtual Reality Experiences". Each of the above-mentioned applications is incorporated herein by reference in its entirety.

BACKGROUND

The present disclosure relates data processing and distribution, and in particular, to rendering, managing, recording, and replaying interactive multiuser virtual reality presentations and experiences.

Computers can include a keyboard and mouse, and programs that respond to user instructions from the keyboard or mouse. Such computers can also provide feedback to a user through a television screen or computer monitor.

SUMMARY

In some embodiments, an apparatus includes a volatile memory, a non-volatile memory, a first processor operatively coupled to the non-volatile memory and configured to receive a data set associated with an object and user information associated with a spatial position of a user with reference to the object and in a virtual environment (IMVR environment), the data set including a spatial data series of the object, and a second processor operatively coupled to the volatile memory, the second processor configured to render, based on the look-up table and the user information, an instance of the portion of the object in the IMVR environment, the instance of the portion of the object being from a perspective of the user, the perspective being based on the spatial position of the user. The first processor is configured to receive a set of inputs from the user, the set of inputs being associated with a set of predetermined properties associated with a portion of the object, the first processor configured to generate a look-up table based on the set of inputs, and the second processor is configured to receive manipulation information related to a manipulation of the instance of the portion of the object by the user, the second processor configured to render, based on the manipulation-information, an updated instance of the portion of the object that manifests an effect of the manipulation in the IMVR environment.

Some embodiments described herein include a non-transitory processor-readable medium storing code representing instructions to be executed by a processor, the code comprising code to cause the processor to receive data including but not restricted to medical images associated with an object and extract a data set associated with a structure of the object (e.g., a bone, muscle, etc.) and user information associated with a spatial position of a user with reference to the object in a virtual environment. The code can further include code to cause the processor to receive a set of inputs from the user, the set of inputs being associated with a set of predetermined properties associated with a portion of the object in the virtual environment, render, based on the set of inputs and the user information, an instance of the portion of the object in the virtual environment, receive manipulation information related to a manipulation of the rendered instance of the portion of the object by the user and in the virtual environment and render, based on the manipulation information, an updated instance of the portion of the object that manifests an effect of the manipulation in the virtual environment. The code can also include code to cause the processor to record media associated with the manipulation and the rendering of the updated instance of the portion of the object, the media including audio and spatial information associated with the rendering of the updated instance of the portion of the object, from a perspective of the user, and the perspective being based on the spatial position of the user.

Some embodiments described herein include a method, including receiving, from a first device and at a second device, (1) a data package associated with a first instance of a portion of an object in a virtual environment, the data package including a data set associated with a three-dimensional structure of the object, (2) first user information including a spatial position of a first user, associated with the first device, with reference to the object in the virtual environment, and (3) a first set of inputs associated with a set of predetermined properties of the object. The method further includes (1) receiving, at the second device, second user information including a spatial position of a second user associated with the second device with reference to the object in the virtual environment, (2) transforming, based on the second user information, the first set of inputs into a second set of inputs, (3) generating, based on the second set of inputs, a look-up-table, and (3) rendering, at the second device and based on (i) the data set, (ii) the second set of inputs, and (iii) the look-up-table, a second instance of the portion of the object in the virtual environment, the second instance of the portion of the object being from a perspective of the second user, and the perspective being based on the spatial position of the second user.

Virtual reality systems have a wide area of applications including entertainment, education, healthcare, business operations, manufacturing, and resource management. Several of these applications can benefit from a joint user experience by two or more users. Providing an interactive user experience where the virtual experience can be manipulated and the results of the manipulations can be experienced by the users can also provide substantial benefits.

Thus, the disclosed embodiments address a need for improved apparatuses and methods for an efficient, managed, recordable, and/or replayable interactive multiuser virtual reality presentation/environment, particularly one that is an efficiently rendered and maintained multiuser virtual reality experience that is interactive to multiple users, in some embodiments at real-time and/or near real-time.

In some embodiments, an apparatus includes a memory and a processor. In some embodiments, a system can include multiple apparatuses. The processor is configured to receive information that can be used to generate an interactive multiuser virtual reality environment. The processor is configured to initialize a state machine to define the interactive multiuser virtual reality environment, render the interactive multiuser virtual reality environment based at least partly on the state machine, communicate with one or more user devices connected to an interactive multiuser virtual reality system, and distribute the information about the rendered interactive multiuser virtual reality environment and/or the state machine defining the interactive multiuser virtual reality environment. The processor is further configured to receive information related to a state of one or more user devices, receive information related to changes induced in the rendered interactive multiuser virtual reality environment due to one or more user actions, and update the rendered interactive multiuser virtual reality environment and/or the state machine defining the interactive multiuser virtual reality environment based on the information received. The processor is configured to provide modifying parameters related to changes in the state of the interactive multiuser virtual reality environment in an efficient, low-bandwidth manner. The processor is further configured to record portions of the interactive multiuser virtual reality environment and allow playback of one or more recorded portions by one or more users.

BRIEF DESCRIPTION OF THE DRAWINGS

FIGS. 9A and 9B are example portions of code that when executed can cause a processor to generate portions of an IMVR experience using an IMVR system, according to an embodiment.

FIGS. 29A, 29B, 30, 31A-31C, 32A, 32B, 33A, and 33B illustrate flowcharts describing implementation of example tools associated with the rendering of a volume object in an IMVR environment, using an IMVR system, according to various embodiment.

FIG. 44A a schematic representation of different types of events associated with an IMVR system.

DETAILED DESCRIPTION

Embodiments described herein relate to methods and apparatus for efficiently rendering and updating an interactive multiuser virtual reality environment that is served to multiple users via multiple user devices connected within a multiuser virtual reality (VR) system. The disclosure includes methods, systems and apparatuses for rendering, managing, recording, and replaying interactive multiuser VR presentations and experiences, including, for example, medical data. Such medical data can be transformed for VR, and can include multiple sources (such as but not limited to Computed Tomography (CT), Magnetic Resonance Imaging (MRI), Electroencephalography (EEG), Magnetoencephalography (MEG), ultrasound imaging, etc.). In some implementations, the medical data is near real-time or real time, and interactions between multiple users can similarly be coordinated. Embodiments can be configured to reduce bandwidth used when multiple users are interacting and manipulating data in a shared VR environment. Additionally or alternatively, embodiments can be configured to reduce storage space used when a multi-user session is recorded, such that subsequent replay by one or more users uses reduced processing power and/or bandwidth.

Described herein are methods and apparatuses for efficient rendering and maintenance of an interactive multiuser virtual reality environment, that can be used for various applications including but not limited to education, training, entertainment, research, diagnosis, surgery, management of patient healthcare, restorative techniques and use of prosthetic devices in healthcare, and manufacturing and repair in the machinery and automotive industry, among others. In some embodiments, an apparatus includes a memory and a processor operatively coupled to the memory. The processor can be configured to be part of a system including one or more user devices. The processor is configured to render an interactive multiuser virtual reality (IMVR) environment and efficiently distribute information related to the rendered IMVR environment to the user devices such that users can be connected to the user devices and can experience and/or interact with the rendered IMVR environment. The processor can be configured to efficiently receive input from the user devices, for example input related to a user interaction. The system is further configured such that the processor can efficiently transfer information related to changes in the state of the IMVR environment, including changes induced by user interaction, to the user devices. In addition, the user devices can also be configured to be able to efficiently transfer information to the processor and/or to each other, enhancing the user experience of the IMVR environment.

Figure 1A:
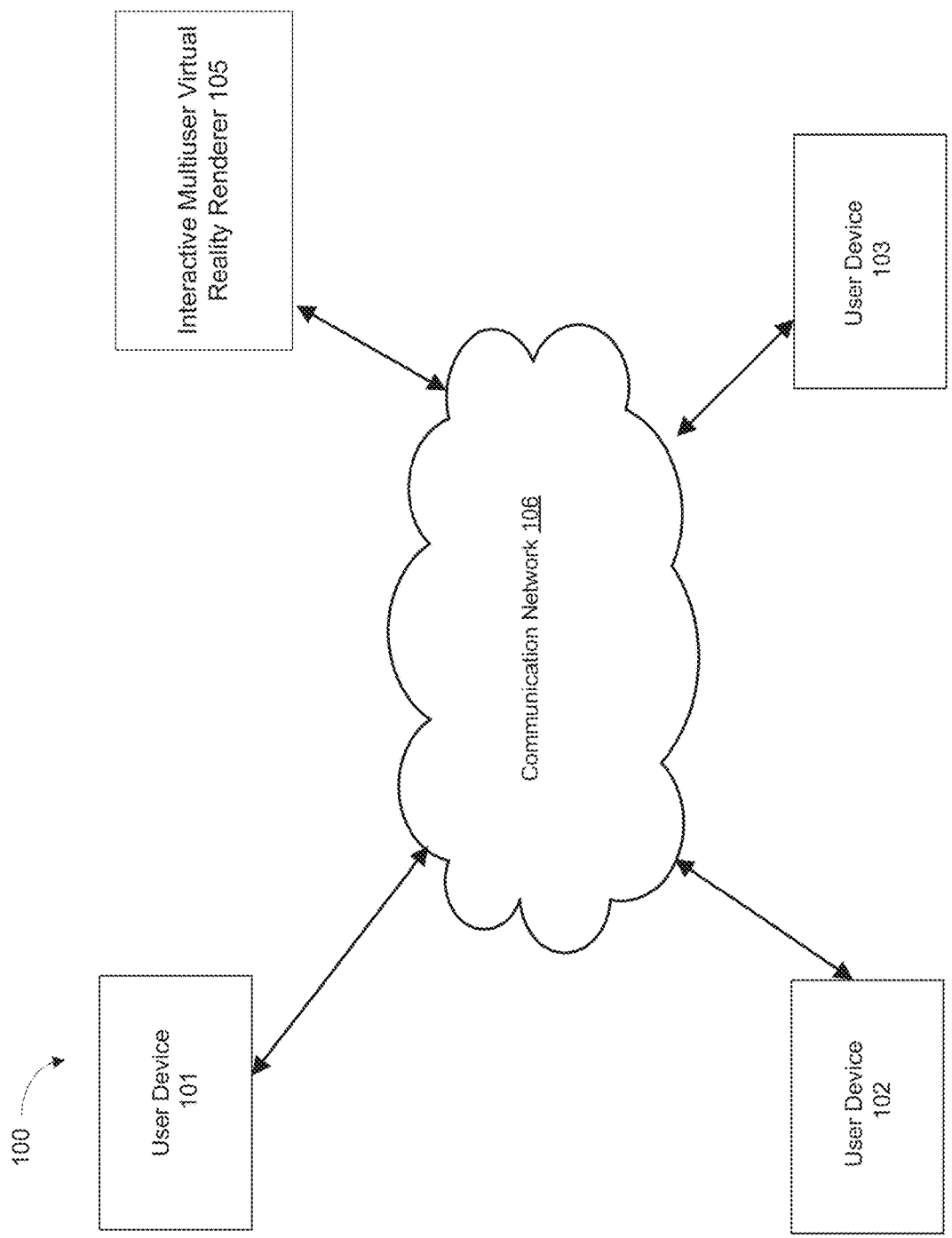
FIG. 1A is a schematic illustration of an Interactive Multiuser Virtual Reality (IMVR) system, according to an embodiment.

FIG. 1A is a schematic illustration of an Interactive Multiuser Virtual Reality system 100, also referred to herein as "an IMVR system" or "a system". The IMVR system 100 is configured to render and maintain an interactive, manipulatable, multiuser virtual reality environment accessed by a set of user devices 101-103 by building, initializing, and maintaining a synchronized and interactive three dimensional IMVR environment. The IMVR system 100 can generate a three dimensional interactive virtual environment from any suitable data provided as basis of the environment, according to an embodiment. The IMVR system 100 includes user devices 101, 102, and 103, connected to an interactive multiuser virtual reality renderer 105 (also referred to as "the renderer") through a communication network 106, as illustrated in FIG. 1A.

Data suitable to be used to render an IMVR environment can include any spatial data series that includes an object. A spatial data series can in some instances includes information defining among other things a volume of an object, In some instances a spatial data series includes information defining a structure (e.g., a three dimensional structure) of an object. A data series can include serial section images of an object obtained through any mode of light microscopy. A data series can include a series of multi-dimensional data including images or point-cloud data. Examples may include data collected using Computed Tomography (CT), Magnetic Resonance Imaging (MRI), Positron Emission Tomography, Confocal Imaging, Light Microscopy, Electron Microscopy, Electroencephalography (EEG), Magnetocardiography (MCG), Magnetoencephalography (MEG), and/or Ultrasound Imaging. In some instances, the spatial data series can include data collected using more than one technique, technology and/or data source. For example, the spatial data series can include data collected from multiple different data sources and loaded to different channels used by the IMVR renderer 105. For example, CT data can be input to a first channel and MRI data can be input into a second channel. The image can then be rendered in the IMVR environment, as described herein, using both the CT data and the MRI data. In other instances, any other combination and/or number of data sources can be used as input.

A spatial data series can include objects related to human or animal anatomy, objects used for research, diagnosis, treatment, veterinary studies of mammalian and/or non-mammalian species, plant studies, other living or non-living tissue (e.g., in-vivo, ex-vivo, in situ, etc.) and organisms naturally occurring or synthetic. While described herein using medical images as an example, the systems, apparatuses and methods described herein can be used to visualize any object using a spatial data series including information related to the structural properties of the object. Other examples of object can be gem stones, or samples from geological studies, samples from archaeological studies, samples from architectural work, etc. A spatial data series can, in some instances, include information related to one or more cellular or sub-cellular objects structure of a molecule (e.g., macromolecules, proteins, etc.). For example, a spatial data series can include data related to a structure and/or surface features of an enzyme molecule modeled and/or generated in three-dimensions from a suitable source, for example a protein structure predicting server (e.g., Advanced Protein Secondary Structure Prediction Server). A spatial data series can, in some instances, include information related to atomic or sub-atomic particles. A spatial data series can, in some instances, include information related to objects electronically generated, for example, mesh objects rendered by an artist. In some instances, the objects can be generated in an IMVR environment, as described herein, using tools provided by an IMVR system, as described herein. In some instances, the electronically generated objects can be obtained or imported from external sources (e.g. any suitable commercially available platform for generating two and/or three-dimensional models of objects), or any other suitable data processing environment, such that the spatial data series can be obtained from a suitable data format.

The communication network 106 (also referred to as "the network") can be any suitable data communication pathway for transferring data that can operate over public and/or private networks. The communication network 106 can include a private network, a Virtual Private Network (VPN), a Multiprotocol Label Switching (MPLS) circuit, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof. In some instances, the communication network 106 can be a wireless network such as, for example, a Wi-Fi or wireless local area network ("WLAN"), a wireless wide area network ("WWAN"), and/or a cellular network. In other instances, the communication network 106 can be a wired connection such as, for example, an Ethernet network, a digital subscription line ("DSL") network, a broadband network, and/or a fiber-optic network. In some instances, the network can use Application Programming Interfaces (APIs) and/or data interchange formats (e.g., Representational State Transfer (REST), JavaScript Object Notation (JSON), Extensible Markup Language (XML), Simple Object Access Protocol (SOAP), and/or Java Message Service (JMS)). The communications can be encrypted or unencrypted. In some instances, the communication network 106 can include multiple networks or subnetworks operatively coupled to one another by, for example, network bridges, routers, switches and/or gateways.

The user devices 101, 102, and 103, in the IMVR system 100 can each be a device or a suitable combination of devices interconnected to each other, associated with one or more users or groups of users. That is, the user devices 101, 102, and 103 can be structurally and/or functionally similar to each other. While illustrated to include three user devices any IMVR system described herein is not limited to two or three user devices and can support a shared IMVR experience via an IMVR session including any number of users.

Figure 1B:
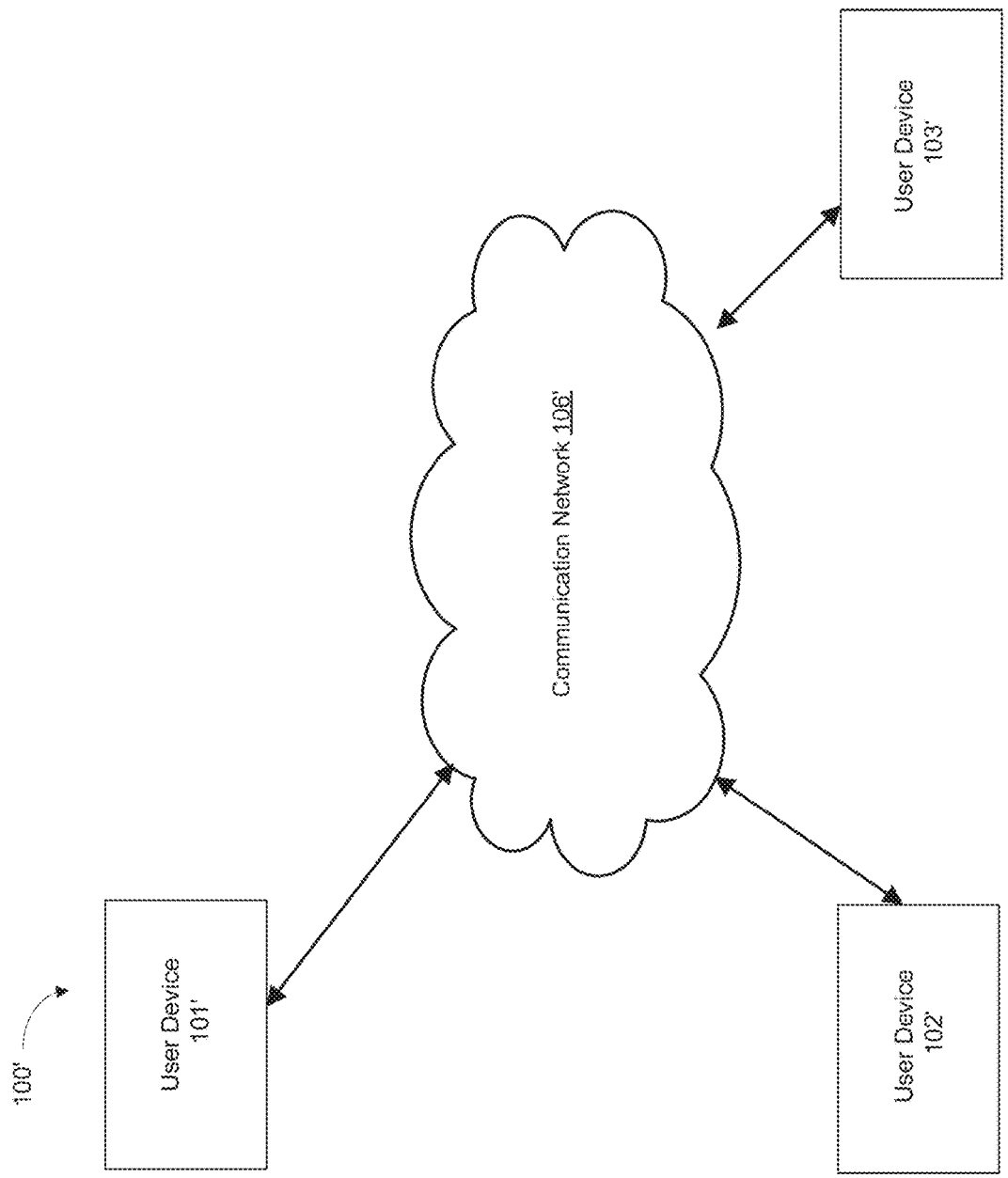
FIG. 1B is a schematic illustration of an Interactive Multiuser Virtual Reality (IMVR) system, according to an embodiment.

FIG. 1B is a schematic illustration of an Interactive Multiuser Virtual Reality system 100', also referred to herein as "an IMVR system" or "a system". The IMVR system 100' is configured to render and maintain an interactive, manipulatable, multiuser virtual reality environment accessed by a set of user devices 101'-103', which each build, initialize, and maintain a synchronized and interactive three dimensional IMVR environment. The IMVR system 100' can generate a three dimensional interactive virtual environment from any suitable data provided as basis of the environment. The IMVR system 100' includes user devices 101', 102', and 103, connected to each other in a peer-to-peer network through a communication network 106', as illustrated in FIG. 1B.

The IMVR system 100' in FIG. 1B can be substantially similar to the IMVR system 100 in FIG. 1A except that the IMVR system 100' does not include an IMVR renderer as a separate device as in the IMVR system 100 (e.g. IMVR renderer 105). Instead, the user devices 101'-103', that are substantially similar to user devices 101-103, can in addition be configured to build, initialize and maintain a synchronized and interactive IMVR environment in a peer-to-peer manner without the use of a server (like an IMVR renderer 105 of the IMVR system 100). While devices, apparatuses, and methods described herein may refer to an IMVR renderer (methods or functions being carried out by an IMVR renderer e.g. IMVR renderer 105, 305 etc.), in some embodiments the IMVR system can be configured similar to the IMVR system 100' and the functions, methods, or processes described as being associated with the IMVR renderer can be performed or carried out in a distributed manner using one or more components in the user devices associated with the IMVR system (e.g. user devices 101'-103' associated with the IMVR system 100').

Figure 2:
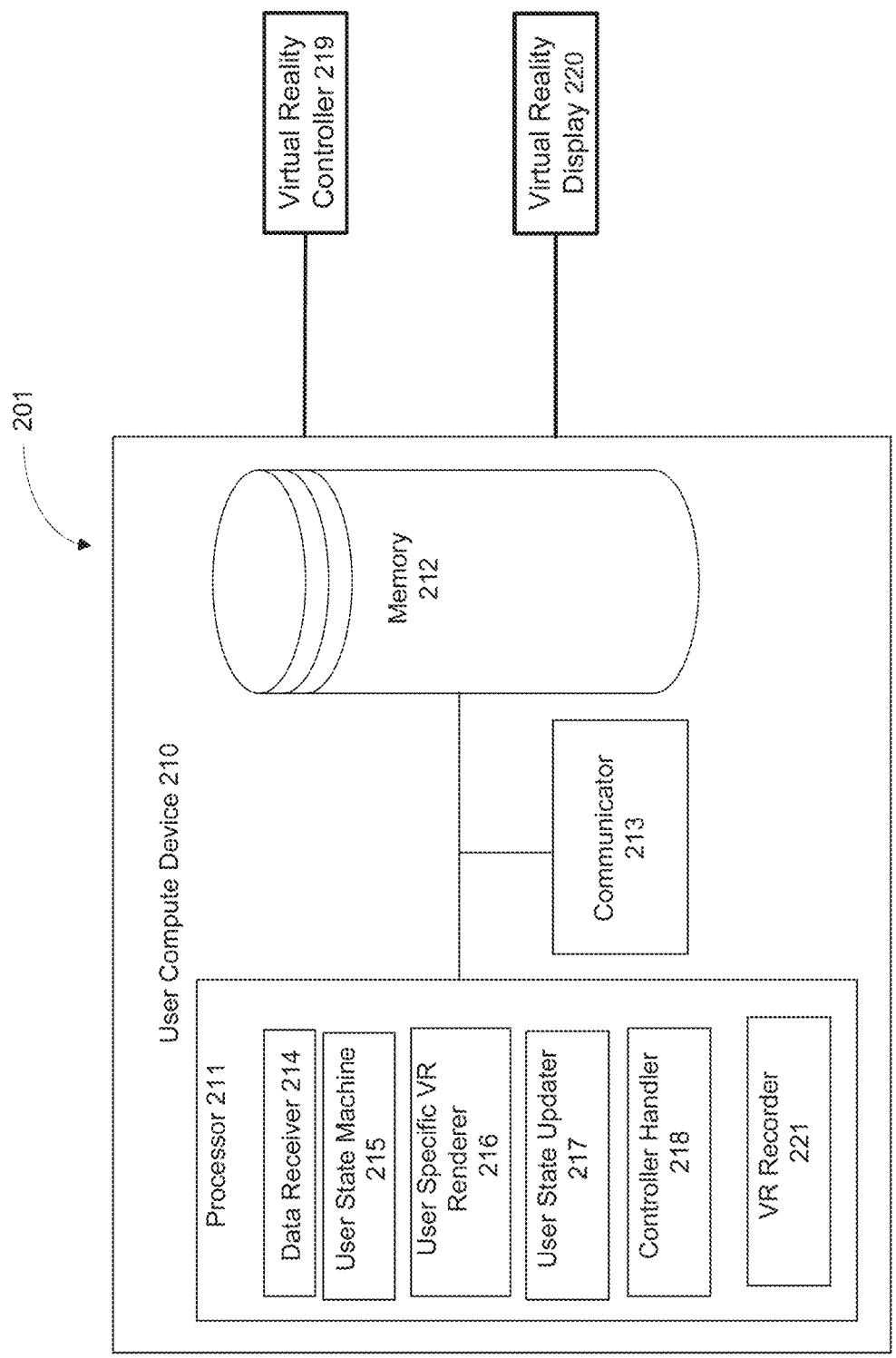
FIG. 2 is a schematic representation of a user device within an IMVR system, according to an embodiment.

FIG. 2 illustrates an example user device 201 that can be substantially similar to the user devices 101, 102, and 103 of FIG. 1. The user device 201 includes a user compute device 210, a virtual reality controller 219, and a virtual reality display 220. In some embodiments, the VR controller 219 and the VR display 220 can be separate devices connected to each other using a suitable wired or wireless connection. In other embodiments, the VR controller 219 and the VR display 220 can be integrated into a single device that includes a display and a controller for the IMVR experience. While not illustrated in FIG. 2, the user device 201 can also include one or more peripheral sensing, receiving or actuating devices of other modalities, such as audio receivers (e.g., microphones) and/or audio players (e.g., speakers), haptic or tactile sensors or actuators, accelerometers, and/or the like, that can be interconnected with the compute device 210, the VR controller 219 and/or the VR display 220.

The VR controller 219 can be any suitable device that can be configured to be used to control one or more components of the user device 201 such as the user compute device 210 and/or the VR display 220. The VR controller 219, in some embodiments, can be a mouse, a keyboard and/or a joystick device. In some embodiments, the VR controller 219 can be an inertial measurement device. In some embodiments, the VR controller 219 can be a motion controller including one or more sensors such as accelerometers, magnetometers, and/or the like. The VR controller 219 can include one or more actuators or control items such as buttons, scroll wheels, handling sticks, etc., that can be used to manipulate components of the user device 201 and/or the IMVR environment. As described herein, while user device 201 is described to include one VR controller 219, any suitable number of VR controllers can be used to manipulate a user device or manipulate an instance of an object rendered in association with the user device and/or an IMVR environment, as described herein. For example, VR controller 219 can be used to initiate an IMVR experience by initiating a user interface (UI) that may be viewed through the VR display 220. The VR controller 219 can be used to modify the UI such as, for example, by clicking buttons, opening menus, etc. The VR controller can be used to generate cursor-like control items that can be used as pointing and manipulating devices in the user interface and/or an IMVR environment.

In some instances, an IMVR environment can include one or more mobile entities, generated within an IMVR environment, that can be manipulated to obtain a two-dimensional view of an IMVR environment from within the IMVR environment, and join an IMVR session. In some instances, a user manipulating a mobile entity may not join an IMVR session but be an observer of the IMVR session from within the IMVR environment. For example, the mobile entity (e.g., a Fly-cam) can be defined within the IMVR environment, and can be used to project a perspective two-dimensional view (from the perspective of the mobile entity) to one or more users. The user associated with the mobile entity can move, rotate and/or orient the mobile entity as desired to view various regions or aspects of the IMVR environment.

In some embodiments, the VR display 220 can be a suitable two-dimensional monitor that is configured to receive data and generate a two-dimensional window into an IMVR environment for a user. In some embodiments, the VR display can also include one or more sensors and/or actuators that can be used to enhance or augment the IMVR experience of the user, such as audio speakers, microphones to receive audio input, eye-movement or pupil tracker to track the movement of the user's eyes, and/or the like.

The VR display 220 can be a suitable virtual reality headset that is configured to receive data and generate a virtual reality experience for a user. In some embodiments, the VR display can include a graphical display unit that can be configured to project 2-D and/or 3-D. In some embodiments, the VR display can also include one or more sensors and/or actuators that can be used to enhance or augment the VR experience of the user, such as audio speakers, microphones to receive audio input, eye-movement or pupil tracker to track the movement of the users eyes, sensors to recognize postural and orientation changes of the users body (e.g. head movements, head orientation, gestures, etc.), sensors to capture body movements and stature, and/or the like.

The user compute device 210 can be a hardware-based computing device and/or a multimedia device, such as, for example, a server, a desktop compute device, a smartphone, a tablet, a wearable device, a laptop and/or the like. In some embodiments, the compute device 210 can be integrated with or part of the VR controller 219 and/or the VR display. In some embodiments, the compute device 210 can be separately housed from and connected to the VR controller 219 and the VR display 220. The compute device 210 includes a processor 211, a memory 212, and a communicator 213.

The processor 211 can be, for example, a hardware based integrated circuit (IC) or any other suitable processing device configured to run and/or execute a set of instructions or code. For example, the processor 211 can be a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 211 can be operatively coupled to the memory 212 through a system bus (for example, address bus, data bus and/or control bus).

The processor 211 can include a data receiver 214, a user state machine 215, a user specific VR renderer 216, a user state updater 217, a controller handler 218, and a VR recorder 221, as illustrated in FIG. 2. Each of the components including the data receiver 214, user state machine 215, user specific VR renderer 216, user state updater 217, controller handler 218, and VR recorder 221, can be software stored in the memory 212 and executed by processor 211 (e.g., code to cause the processor 211 to execute the data receiver 214, the user state machine 215, the user specific VR renderer 216, the user state updater 217, the controller handler 218, and the VR recorder 221). The code to execute the components can be stored in the memory 212 and/or a hardware-based device such as, for example, an ASIC, an FPGA, a CPLD, a PLA, a PLC and/or the like.

The data receiver 214 is configured to receive data transferred from the VR controller 219, the VR display 220, an IMVR renderer connected to the user device 201 via a communication network (e.g., the IMVR renderer 105 in the IMVR system 100 illustrated in FIG. 1), and/or other user devices (e.g., user devices connected to the same IMVR system that the user device 201 is part of). In some implementations, the data receiver 214 can be configured to receive an initialized state indicating the state of an interactive multiuser VR environment generated by an IMVR renderer. In some instances, the data receiver 214 can receive updates to the state of the VR environment already generated and initialized by the IMVR renderer. For example, the updates can represent changes to relative location and/or state of objects or other users in the VR environment that may be from interaction of other users also connected to the IMVR system.

The user state machine 215 can be configured to generate and maintain a set of indications that represent a state of the user using the user device 201. In some implementations, the user state machine 215 can define a user state based on inputs received from the user such as inputs from the VR controller 219, and/or other sensing, receiving, and/or actuating device(s) connected to the user (e.g. microphones, haptic receivers, accelerometers, etc.) and maintain the user state during a session of the users VR experience.

The user specific VR renderer 216 can be configured to use data received from a renderer (e.g., renderer 105 of IMVR system 100 shown in FIG. 1) relaying information about an IMVR environment, and the user specific VR renderer 216 can be configured to generate and maintain a user specific IMVR experience for the user of the user device 201. In some embodiments, in an IMVR system operating without a server having an IMVR renderer (e.g., IMVR system 100' of FIG. 1B), the user specific VR renderer 216 can be configured to use data relaying information about an IMVR environment, received directly, and the user specific VR renderer 216 can be configured to generate and maintain a user specific IMVR experience for the user of the user device 201. For example, the user specific VR renderer 216 can receive information related to the IMVR environment in which the user of device 201 is participating and the relative action, position or vantage point of the user using the user device 201 (e.g., spatial location, posture, interaction with the VR environment, etc.). Using this information the user specific VR renderer 216 can generate a user specific version of the IMVR environment that is tailored to apply to the user of the user device 201. The user specific version of the IMVR environment can include presentation of the IMVR environment from the perspective of the user of user device 201 including suitable modifications to the visual, audio, haptic and/or other modalities of the IMVR environment as will be perceived by the user's virtual presence in the IMVR environment. For example, in some implementations, the user specific VR renderer 216 can modify the view of the IMVR environment based on the spatial location of the user as deduced by tracking the location of the VR controller 219 and/or the VR display 220. In some implementations, the user specific renderer 216 can be configured to reveal certain aspects of the IMVR environment (e.g., certain objects or views in the IMVR environment) to the user of the user device 201, where the revealed objects are otherwise unavailable to one or more other users (e.g., invisible or occluded from view, etc.).

The processor 211 includes a user state updater 217 that is configured to receive information from the VR controller 219, the VR display 220, and/or other peripheral sensing, receiving and/or actuating devices. The user state updater 217 is further configured use the information received to record changes in the state of the user and/or the user's immediate environment, that is, any action of the user or any manipulation by the user upon the IMVR environment. The user state updater 217 uses the information to update the user state machine 215 and communicates the changes to the user state machine 215 and/or to an IMVR renderer (e.g., the renderer 105 of system 100 in FIG. 1A). In some implementations, the user state updater 217 can be configured to also communicate the changes to the user state machine 215 to other users that may be connected to the same IMVR system. In some implementations, the user state updater 217 can be configured to directly communicate the changes to the user state machine 215 to other user devices that may be connected to the same IMVR system, in a peer-to-peer manner, without involving a server such as an IMVR renderer (e.g. in a IMVR system 100' of FIG. 1B).

In some implementations, the user state updater 217 can also record changes to the IMVR environment induced by the changes to the user state and communicate the changes to an IMVR renderer (e.g., renderer 105 of system 100) and/or other user devices (e.g., user devices 101, 102, and 103 of IMVR system 100). As an example, if a user of the user device 201 magnifies a portion of a VR environment, for example, the heart portion in a VR environment depicting internal anatomical structures (e.g., vasculature) of the circulatory system of a subject, the user state updater 217 can record properties of manipulation such as the points of magnification, the scale of magnification, the axis along which the VR environment is magnified, etc. The user state updater 217 can update the user state machine 215 relating to the state of the user (e.g., the control points used by the user, the gesture of the user to magnify, positions of one or more control objects such as cursors used by the user, etc.) and communicate the changes to an IMVR renderer. The user state machine can also record changes induced in the IMVR environment by the user's manipulation as perceived by the user and communicate the induced changes in the IMVR environment to the renderer. For example, the user state updater 217 can also communicate the resulting change in magnification of the specific structures or portions of the IMVR environment to the IMVR renderer and/or other user devices in the IMVR system.

The processor 211 includes a controller handler 218 configured to send commands and receive feedback from the VR controller 219. In some implementations, the controller handler 218 can be configured to generate and guide and/or direct one or more control objects associated with the VR controller 219. In some implementations, the controller handler 218 can be configured to perform pointing and tracking procedures using the VR controller 219. In some implementations, the controller handler 218 can deduce the point of focus and the actions performed by the user via the VR controller 219 using one or more procedures such as ray casting, orientation detection, rotation detection, detecting the positional vectors of the VR controller in a suitable co-ordinate space, and/or the like. In some implementations, the controller handler 218 can work in concert with one or more other components or portions of components of the user device 201. For example, the controller handler 218 can work in concert with an eye-tracking device in the VR display 220 or with other sensors and actuators that may be included (not shown in FIG. 2). While the user device 201 in FIG. 2 shows one VR controller 219, any number of suitable VR controllers can be included in a user device. For example, in some implementations, a user device can include two controllers each guiding one cursor, that can be used to manipulate two points of access in an IMVR environment or two points of access on an instance of an object rendered in association with the user device to perform manipulations that may sometimes use two point access such as, for example, change in magnification, pivoting, turning, etc. The controller handler 218 can also be configured to work in concert with other components of the processor 211 such as the user state machine 215, the user state updater 217, and/or the user specific VR renderer 216 to present and update the IMVR environment to the user of the user device 201 as well as to communicate any user-induced changes to a IMVR renderer and/or other user devices in a IMVR system.

The processor 211 can include a VR recorder 221 that is configured to, upon initiation by a user, record at least a portion of the IMVR environment experienced by the user. Such a recording can be saved for later playback, for example, in memory 212 of the user compute device 211.

The memory 212 of the user compute device 210 can include a non-volatile and a volatile memory, for example, a random access memory (RAM), a video RAM (VRAM) a memory buffer, a hard drive, a read-only memory (ROM), an erasable programmable read-only memory (EPROM), and/or the like. In some embodiments, the non-volatile memory can be associated with a processor and the volatile memory can be associated with the processor. In some embodiments, different processors (e.g., a first processor (CPU) and a second processor (GPU)) or portions of processors can be associated with the non-volatile and the volatile memory, respectively. The memory 212 can store, for example, one or more software modules and/or code that can include instructions to cause the processor 211 to perform one or more processes, functions, and/or the like (e.g., the data receiver 214, the user state machine 215, the user specific VR renderer 21, the user state updater 217, the controller handler 218 and/or the VR recorder 221). In some implementations, the memory 212 can be configured to receive and store data transferred from and/or to an IMVR renderer (e.g. the IMVR renderer 105 of system 100 in FIG. 1A), the VR controller 219, and/or the VR display 220. In some implementations, the memory 212 can be configured to receive and store data transferred directly from and/or to one or more user devices (e.g., the user devices 101'-103' of system 100' in FIG. 1B) in a peer-to-peer manner, in addition to and/or from the VR controller 219, and/or the VR display 220. In some implementations, the memory 212 can be a portable memory (for example, a flash drive, a portable hard disk, and/or the like) that can be operatively coupled to the processor 211. In some instances, the memory can be remotely operatively coupled with the user compute device 210. For example, a remote database server can be operatively coupled to the user compute device 210.

The communicator 213 can be a hardware device operatively coupled to the processor 211 and memory 212 and/or software stored in the memory 212 executed by the processor 211. The communicator 213 can be, for example, a network interface card (NIC), a Wi-Fi™ module, a Bluetooth® module and/or any other suitable wired and/or wireless communication device. Furthermore the communicator can include a switch, a router, a hub and/or any other network device. The communicator 213 can be configured to connect the user compute device 210 to a communication network (such as the communication network 106 shown in FIG. 1). In some instances, the communicator 213 can be configured to connect to a communication network such as, for example, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof.

In some instances, the communicator 213 can facilitate receiving and/or transmitting a file and/or a set of files through a communication network (e.g., the communication network 106 in the IMVR system 100 of FIG. 1). In some instances, a received file can be processed by the processor 211 and/or stored in the memory 212 as described in further detail herein.

Figure 3:
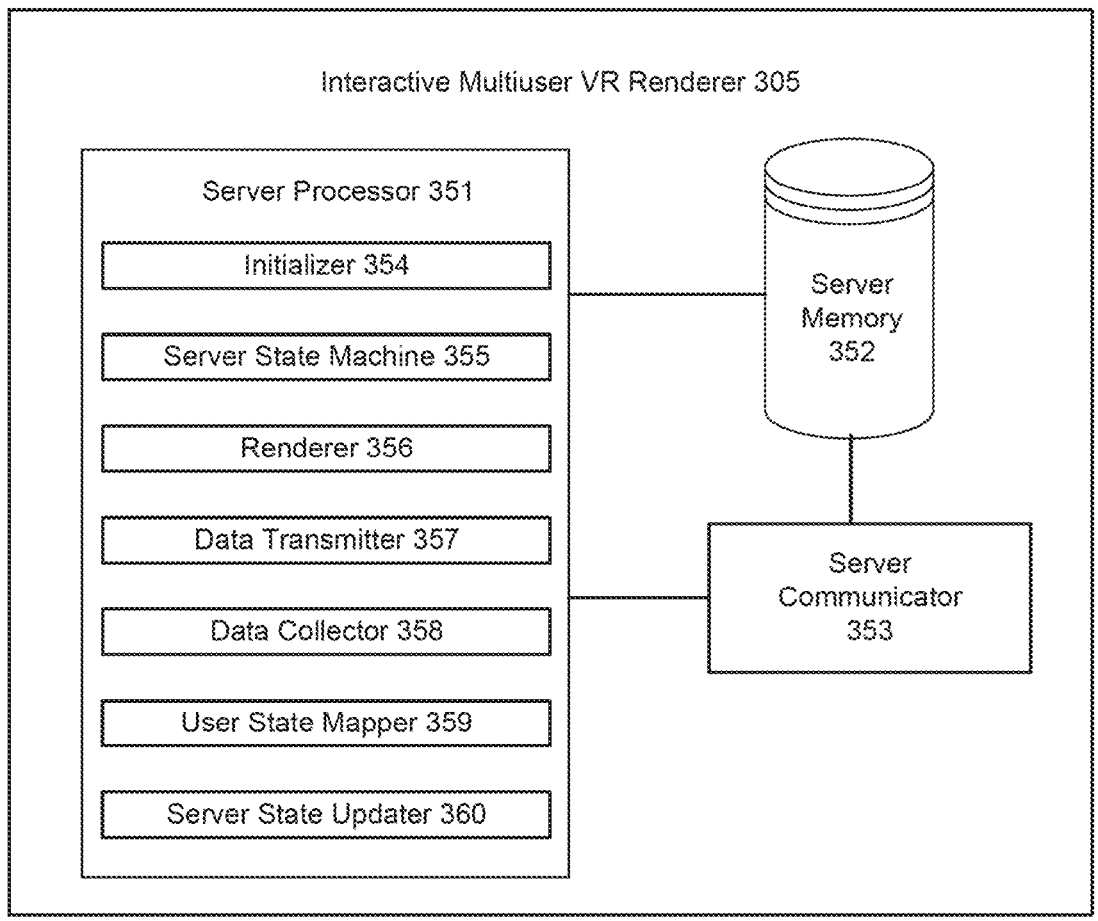
FIG. 3 is a schematic representation of an interactive multiuser VR renderer within an IMVR system, according to an embodiment.

Returning to FIG. 1A, the user devices 101-103 that are connected to IMVR system 100 can be configured to communicate with an IMVR renderer. FIG. 3 is a schematic representation of an IMVR renderer 305 that is part of an IMVR system. The IMVR renderer 305 can be structurally and functionally similar to the renderer 105 of the system 100 illustrated in FIG. 1. The IMVR renderer 305 includes a server processor 351, a server memory 352, and a server communicator 353. As described previously, in some embodiments an IMVR system can be configured to operate in a peer-to-peer manner without an IMVR renderer (e.g., IMVR system 100' in FIG. 1B) in which case the components (e.g., server processor 351, server memory 352, and server communicator 353) and operations associated with the components, described below with reference to the IMVR renderer 305, can be performed by one or more components in the user devices (e.g., user devices 101'-103' of FIG. 1B) in a distributed manner.

In some embodiments, an IMVR environment (hybrid between the centrally controlled IMVR system 100 of FIG. 1A and the peer-to-peer IMVR system 100' of FIG. 1B) can be configured such that it includes a server that is used for one or more functions and/or operations while other operations are performed in a distributed manner by the user devices connected to each other. For example, in some such embodiments, there may be included a server that is used to save and serve data packages to user devices during initialization of an IMVR session but plays limited or no part in data transfers or communications during an IMVR session. As another example, in some embodiments, an IMVR system can include a server used to save information related to an IMVR session (e.g., save a recording of an IMVR session) but does not perform other functions related to the IMVR session.

The server processor 351 can be a hardware based integrated circuit (IC) or any other suitable processing device configured to run and/or execute a set of instructions or code. For example, the server processor 351 can be a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The server processor 351 is operatively coupled to the server memory 352 through a system bus (e.g., address bus, data bus and/or control bus). The server processor 351 is operatively coupled with the server communicator 353 through a suitable connection or device as described in further detail.

Similar to the communicator 213 within user compute device 210 of the user device 201 of FIG. 2, the server communicator 353 can be a hardware device operatively coupled to the server processor 351 and the server memory 352 and/or software stored in the server memory 352 executed by the server processor 351. The server communicator 353 can be, for example, a network interface card (NIC), a Wi-Fi™ module, a Bluetooth® module and/or any other suitable wired and/or wireless communication device. Furthermore the communicator 353 can include a switch, a router, a hub and/or any other network device. The server communicator 353 can be configured to connect the IMVR renderer 305 to a communication network (such as the communication network 106 shown in FIG. 1). In some instances, the server communicator 353 can be configured to connect to a communication network such as, for example, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof.

The server memory 352 can be a random access memory (RAM), a memory buffer, a hard drive, a read-only memory (ROM), an erasable programmable read-only memory (EPROM), and/or the like. The server memory 352 can store, for example, one or more software modules and/or code that can include instructions to cause the server processor 351 to perform one or more processes, functions, and/or the like. In some implementations, the server memory 352 can be a portable memory (e.g., a flash drive, a portable hard disk, and/or the like) that can be operatively coupled to the server processor 351. In some instances, the server memory can be remotely operatively coupled with the server. For example, the server memory can be a remote database server operatively coupled to the server and its components.

The server processor 352 can be configured to perform several functions, as described in further detail herein, including collecting receiving and storing data from external sources, using the data to generate IMVR environments, collecting data from user devices connected though an IMVR system (similar to the IMVR system 100 in FIG. 1), maintaining and updating an IMVR environment with one or more online users and/or the like. The server processor 351 can include one or more units configured to perform predetermined functions, the one or more units being hardware based units (e.g., an integrated circuit (IC) or any other suitable processing device configured to run and/or execute a set of instructions or code) or virtual machine units generated by execution of a set of instructions or code, or a combination of the two. For example, as illustrated in FIG. 3, the server processor 351 can include an initializer 354, a server state machine 355, a renderer 356, a data transmitter 357, a data collector 358, a user state mapper 359, and a server state updater 360. Each of the components including the initializer 354, the server state machine 355, the renderer 356, the data transmitter 357, the data collector 358, the user state mapper 359, and the server state updater 360, can be software stored in the server memory 352 and executed by server processor 351 (e.g., code to cause the server processor 351 to execute the initializer 354, the server state machine 355, the renderer 356, the data transmitter 357, the data collector 358, the user state mapper 359, and/or the server state updater 360). The code to execute the components can be stored in the server memory 352 and/or a hardware-based device such as, for example, an ASIC, an FPGA, a CPLD, a PLA, a PLC and/or the like.

The Initializer 354 can be configured to generate and initialize an IMVR environment that can be used by one or more users. In some implementations, the initializer 354 can be configured to generate a user interface (UI) that can be used to communicate with an IMVR system (e.g., IMVR system 100 of FIG. 1), and/or generate an IMVR environment. FIGS. 9A and 9B show example portions of code that can be executed by a processor (e.g., server processor 351) to generate a UI (e.g. a ModuleUI). In some implementations, the initializer can be configured to browse and load data, in suitable formats, from external sources (e.g., via the server communicator 353) and use the data to generate the IMVR environment. For example, in some instances, the initializer 351 can receive medical images of known data formats (e.g., Digital Imaging and Communications in Medicine (DICOM) images or RAW images) and initialize an IMVR environment based on the images. As an example, the images can contain information regarding a subject's organ systems (e.g., nervous system, circulatory system, or respiratory system), which can be used to generate an IMVR environment where the internal structures can be viewed and/or probed with high magnification, definition and specificity, etc. The initializer 354 can define various variables and parameters related to generating the IMVR environment. In some implementations, the initializer 354 can call any number of functions and/or sub-functions that generate various aspects of the initial IMVR environment. In some implementations, the initializer 354 can be configured to build a server state machine 355 that defines the IMVR environment based on a set of properties.

The server state machine 355 can be a device or a unit of the server processor 351 that can be in one of a set of predetermined stable states. The state machine 355 can be defined by a set of properties and each property can assume one of a set of parameter values. The state of the server state machine 355 can be defined by the parameter values of the set of properties of the server state machine 355. The properties and the parameter values of the server state machine 355 can be set and/or modified by other components or units of the server processor 351 such as the initializer 354 or the server state updater 360. For example, the initializer 354 can set initial parameter values for each of the properties of the server state machine 355, and initialize the server state machine 355.

The server processor 351 can include a renderer 356 configured to use information such as the state of the server state machine 355 and render the IMVR environment for the participation and interaction of one or more users. The renderer 356 can in turn call or cause the execution of one or more functions or sub-functions that perform portions of rendering the IMVR environment. For example, the renderer 356 can call other functions, including a volumizer (also referred to herein as a "volume renderer"), that fills volumes of objects with three dimensional shape in the environment, and/or functions that control various aspects of surface appearance of objects included in the IMVR environment (e.g., a texturizer, a shader, a blender, etc.), example embodiments of which are described in further detail herein.

Figure 12:
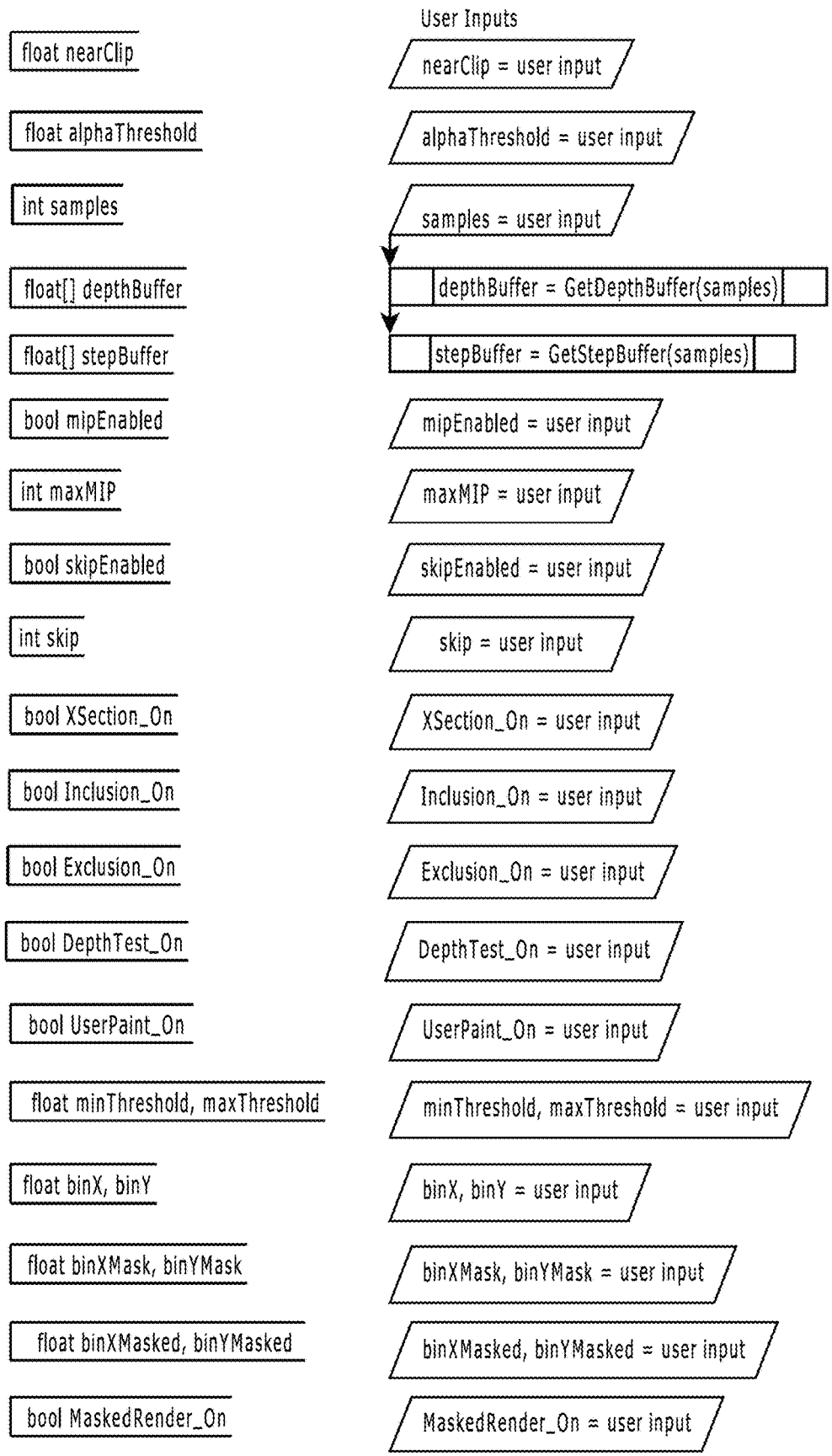
FIG. 12 is a schematic representation of a subset of variables, with values set based on user input, used to render an IMVR environment, according to an embodiment.

In some implementations, the renderer 356 can generate and/or use predetermined values in the form of threshold criteria, preset coefficients or look up tables (LUT) to guide rendering of objects within the IMVR environment. In some instances, the one or more predetermined values and parameter values of the server state machine 355 can be accessible to be set or modified by one or more users. In some implementations, the renderer 356 can receive information from a user to set values of a subset of variables used to render an IMVR environment. FIG. 12 illustrates some example variables that can be configured to be set by the renderer 356 based on user input. In some instances, the IMVR renderer 305 may be operated in one or more test implementations such that the renderer 356 can try various values of the one or more predetermined values and/or parameter values of the server state machine 355, which can then be stored and used to initialize an IMVR environment in a later implementation.

The server processor 351 can include a data transmitter 357 and a data collector 358 configured to send to and receive from any number of user devices connected to the IMVR Renderer 305. The data transmitter 357 can, for example, transmit information about a rendered IMVR environment, the state of a server state machine, properties of the environment, etc. The data collector 358 can be configured to receive or collect data from the connected user devices, the data including information of the states of various user state machines (e.g., the user state machine 215 described with reference to the user device 201), movements or gestures by a user, communication between users, etc.

The server processor 351 can include a user state mapper 359 that assimilates information received from user devices and maps the information onto potential changes in the IMVR environment and/or server state machine 355. The server state updater 360 then can be configured to use the information received from user devices and mapped by the user state mapper 359 to update the server state machine 355. For example, changes to an IMVR environment from a perspective of a particular user device (i.e., the changes being induced by actions of a user using that user device), can be received by the data collector 358. The changes induced by the user's action can be converted from the perspective of the user to the general coordinates of the IMVR environment by the user state mapper 359. The server state updater 360 can then use this information to update the server state machine 355.

In some instances, the data collector 358 and the data transmitter 357 can aid in establishing a synchronized IMVR experience between two user devices connected to the IMVR Renderer 305. In some implementations, the user devices can themselves mediate the establishment of a synchronized IMVR experience, for example by communication of data related to the server state machine and the user state machines between the user devices.

While the description of a user device includes a user compute device that includes a processor and a memory, in some embodiments a user device can be configured to include more than one memory and more than one processor that can be used to carry out the functions described above. A user device can include a volatile memory (e.g. memory associated with a Graphics Processing unit (GPU), video random-access memory (VRAM)) and a non-volatile memory (e.g. memory associated with a Central Processing unit (CPU), RAM), and a first processor operatively coupled to a non-volatile memory (e.g. CPU) and a second processor operatively coupled to the volatile memory (e.g., GPU). Any combination of the functions described above as being performed by a component of a processor can be performed by a component of the first processor or the second processor. For example, the functions described in association with the user compute device 210 can be split between a first processor and a second processor, with the data receiver, controller handler, and/or the VR recorder can be associated with the first processor and the user state machine, user specific VR renderer, and/or the user state updater can be associated with the second processor.

While the description of an IMVR renderer (IMVR renderer 305) includes a server processor and a server memory, in some embodiments the server memory can include a volatile memory (e.g. memory associated with a Graphics Processing unit (GPU), video random-access memory (VRAM)) and a non-volatile memory (e.g. memory associated with a Central Processing unit (CPU), RAM). And the functions described to be associated with the IMVR renderer can be split between a first processor and a second processor, the first processor being operatively coupled to the non-volatile memory (e.g. CPU) and the second processor being operatively coupled to the volatile memory (e.g., GPU). For example, in some embodiments, the initializer, data transmitter, and/or the data collector, can be components associated with the first processor and the server state machine, the render, the user state mapper and/or the server state updater can be associated with the second processor.

Figure 4:
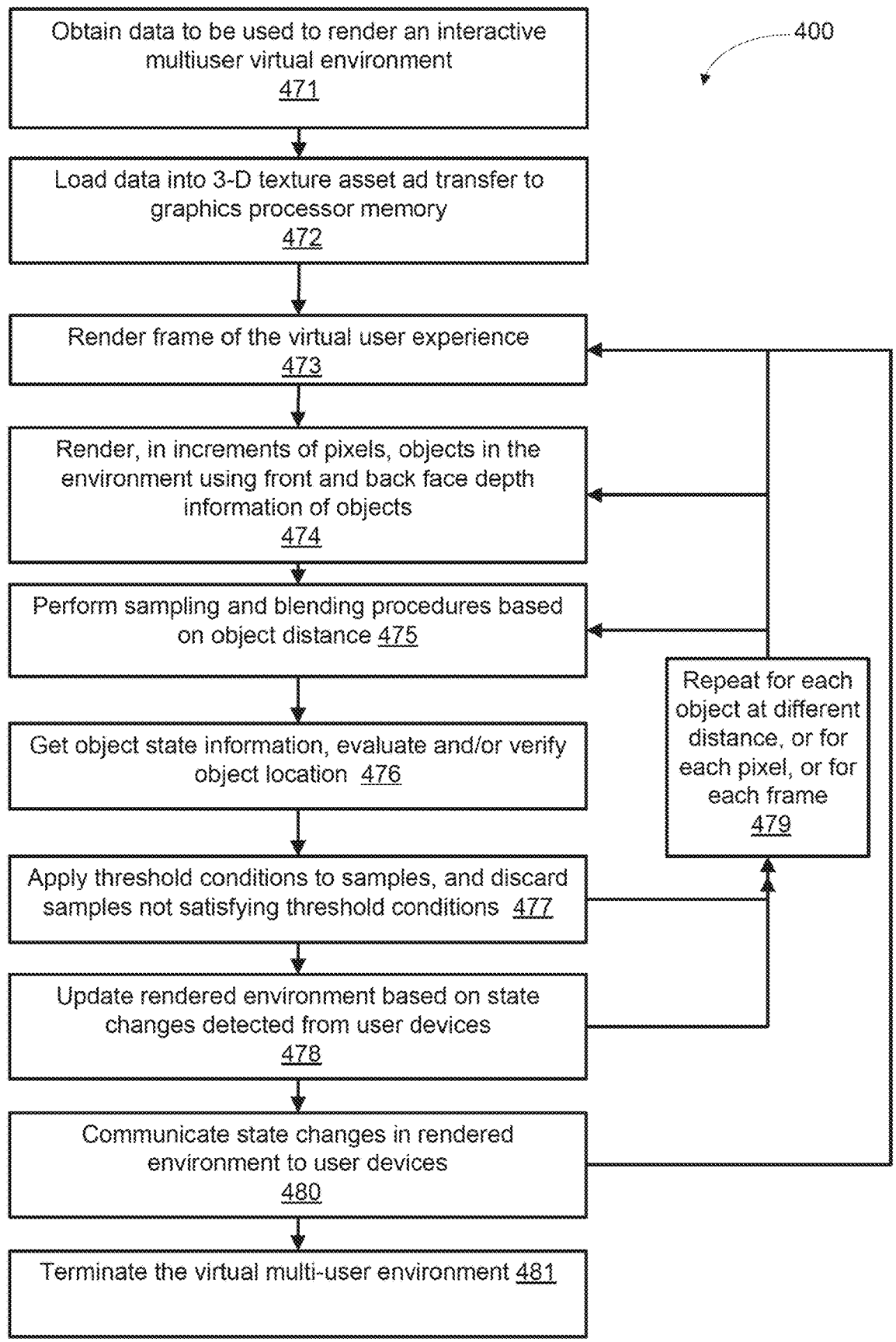
FIG. 4 is a flowchart describing a method of initializing, rendering and updating an IMVR system, using an IMVR renderer, according to an embodiment.

FIG. 4 is a flowchart describing an example method 400 carried out by an IMVR renderer (such as the IMVR renderer 305) to generate and maintain an IMVR environment. As described previously, in some embodiments an IMVR system (e.g., IMVR system 100' of FIG. 1B) can be configured such that user devices are connected to each other in a peer-to-peer manner, without an IMVR renderer. In such embodiments, methods and/or functions described herein as being carried out by an IMVR renderer (e.g., method 400 of FIG. 4) can be performed or carried out by one or more components of the user devices (e.g., user devices 101'-103' of IMVR system 100'). In use, the IMVR renderer can, at 471, obtain data related to imagery or other information that can be used in the generation of an IMVR environment or IMVR experience. In some instances, the data can include three dimensional stacks of imagery such as medical imagery, that can be used to generate interactive multiuser VR environments that can be used for diagnostic, educational, research, or training purposes, among others.

At 472, the obtained data can be loaded into a suitable basis for an IMVR environment. For example, the data can be loaded onto a pre-existing or pre-determined texture basis called a texture asset. The loaded three dimensional texture asset can be transferred from a temporary memory or a random-access memory (RAM) to a graphics processor memory (GPU memory).

At 473, the IMVR server can render a frame of the virtual experience. At 474, the IMVR renderer renders, in increments of pixels, objects in the environment using front and back face depth information of objects. At 475, the IMVR renderer performs sampling and blending procedures on the populated objects, based on the object distances. For example, a sampling procedure can include querying a set of points in space in a three dimensional data set, based on a calculated spatial position of a user, to receive sampling information related to intensity values of object in that point in space. The IMVR renderer can based on the sampling information present a projection of a three dimensional object via a projected representation of the set of points in space from a perspective of the user.

At 476, the IMVR renderer receives information about the state of the objects (e.g., via a state of a server state machine) and evaluates and/or verifies the object location based on other related data such as relative size of objects, occlusion, etc.

At 477, the IMVR renderer applies threshold conditions to samples, and discards samples not satisfying the threshold conditions. For example an IMVR renderer can receive inputs associated with a threshold setting defining the viewable range of a data set, with only sample above threshold being rendered viewable. In some implementations the IMVR renderer can receive the threshold setting using a threshold slider control tool. Using the samples that have been evaluated against threshold criteria and predetermined conditions, the server state machine can be updated. The evaluation step can be performed repeatedly and iteratively over pixels, over objects listed by distances, and/or over frames of the rendered IMVR environment, as indicated by the step 479. For example a renderer can operate at pixels being updated every 200 msec, As another example a renderer can operate at frames being updated at 60 frames per second (fps).

At 478, the IMVR renderer updates the rendered environment based on state changes detected from user devices. The IMVR renderer can receive information related to user state changes from one or more connected user devices and, based on the received information, the IMVR renderer can update the server state machine. At 479 the IMVR renderer repeats the steps from 475 to 477, from 474 to 477, and from 473 to 477 in iterative cycles, for each object at different distance, for each pixel, and for each frame, respectively. The server state machine can be updated with information from user state changes in an iterative process after evaluation of the rendered environment by each pixel, each object listed by location or distance, and/or by each frame of the rendered environment, as indicated at 479.

At 480, the IMVR renderer communicates state changes in the rendered environment to user devices. The IMVR renderer can communicate to one or more user devices, the updated state of the rendered environment, for example via a state of the server state machine. The steps of rendering an IMVR environment or a portion of an IMVR environment and communicating the state changes to user devices (473-480) can be repeated iteratively as user movements and/or actions are monitored. Upon completion of the user experience by one or more of the connected users, at 481, the rendered multiuser environment can be terminated.

Figure 5:
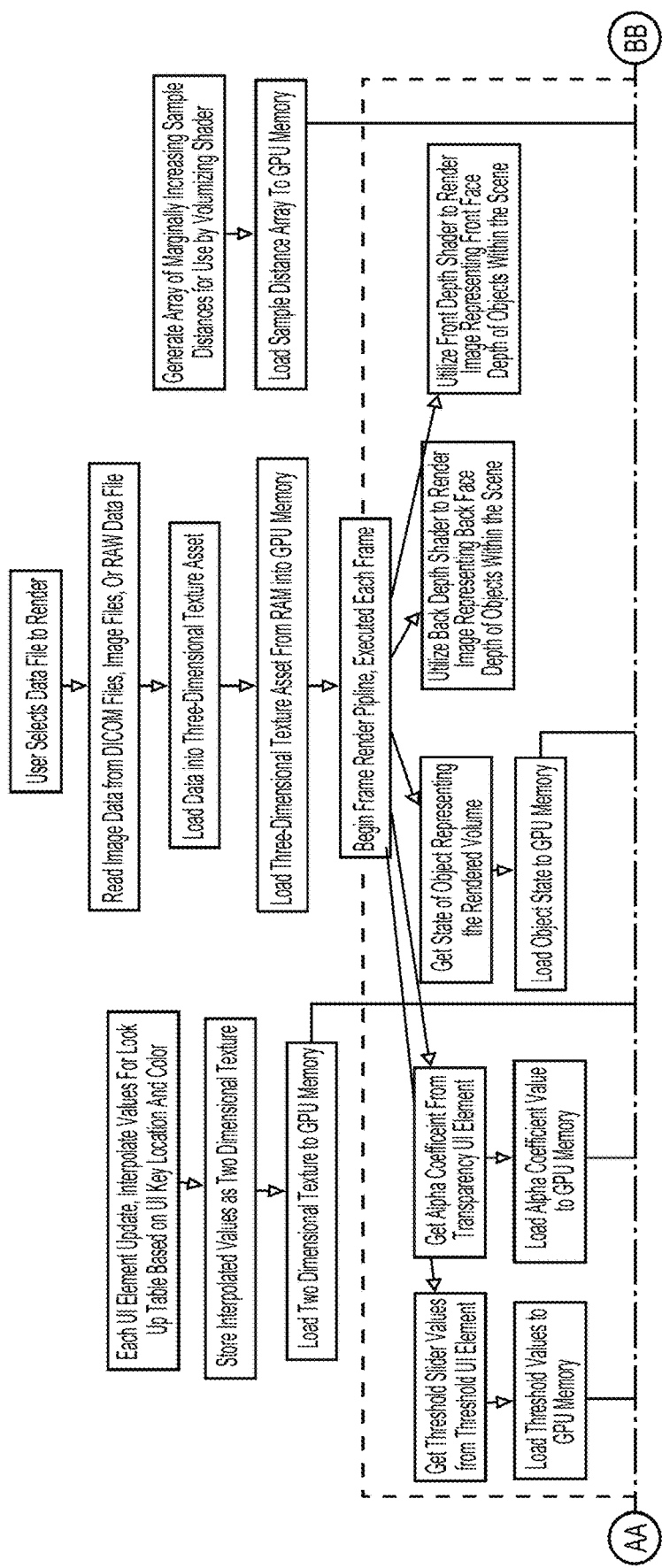
FIG. 5 is a flowchart describing an example method of rendering a volumetric environment portion of an IMVR experience, according to an embodiment.
Figure 5:
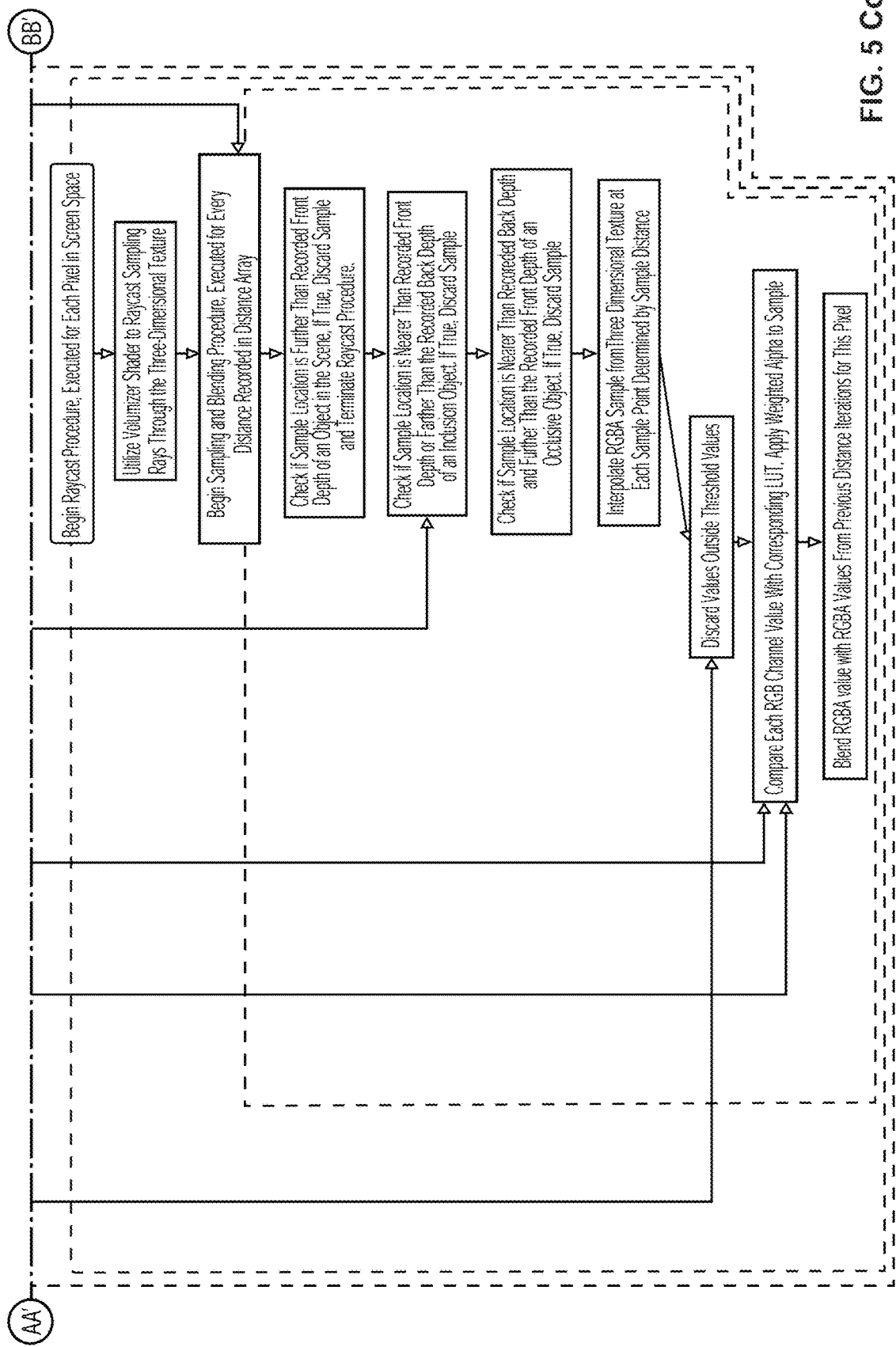

FIG. 5 is an illustration of a flowchart 500 describing an example method of rendering a volumetric IMVR environment using an IMVR system as described herein, according to an embodiment. In some instances, the volumetric rendering can be performed by an IMVR renderer (e.g., Renderer 305) in an IMVR system. As described previously, in some embodiments an IMVR system (e.g., IMVR system 100' of FIG. 1B) can be configured such that user devices are connected to each other in a peer-to-peer manner, without an IMVR renderer. In such embodiments, methods and/or functions described herein as being carried out by an IMVR renderer (e.g., method 500 of FIG. 5) can be performed or carried out by one or more components of the user devices (e.g., user devices 101'-103' of IMVR system 100'). In some instances, the volumetric rendering can be performed by a renderer associated with a user device (e.g., User specific renderer 216 of user device 201). For example, the Renderer can read data from a set of DICOM files or Image files or RAW data files, or any other suitable data series and load the data into a volatile memory (e.g., GPU memory) or a user device.

The renderer can obtain a set of values associated with properties that may be associated with a volume object to be rendered. Some example properties include viewability set using a threshold value, transparency set using an alpha coefficient, state of object, depth of object from a user's perspective (e.g., front face depth representing the front most surface of the object with respect to the user and a back face depth representing the farthest depth of the object from the user). In some instances, one or more values associated with the properties can be provided by a user.

The IMVR renderer can sample a point in space provided by one or more channels of three dimensional data. The sample can for example be an RGBA sample including intensity values associated with three color coded data channels—Red (R), Green (G) and Blue (B), and a transparency channel (A) corresponding to intensity data. The IMVR renderer can evaluate the depth of the sampled point and its relation to the object to be rendered (e.g. the depth of the sampled point with respect the front face depth and the back face depth), evaluate for an occlusive object in the path of sight from the user. The IMVR renderer can receive inputs associated with a threshold property configured to set a viewable range of the data set, with only sample above threshold being rendered viewable. In some implementations the IMVR renderer can receive the threshold setting using a threshold slider control to compare the sampled value against a threshold property value indicating viewability. Upon the sample value(s) being greater than the threshold, the renderer can map the sample value(s) to one or more look-up tables (e.g., one LUT per channel) generated based on user predetermined properties (e.g., color and transparency properties associated with an object) and can present the mapped value as an instance of a portion the volume object to be rendered. The IMVR renderer can present the returned mapped value in a pixel by pixel manner, and render the volume object in a frame by frame manner. The IMVR renderer can repeat this process of sampling and rendering in a distance dependent manner depending on object distance from the user. In some implementations, the IMVR renderer can blend the values in the RGBA sample with values from other RGBA samples from previously made distance iterations for a pixel.

Figure 6:
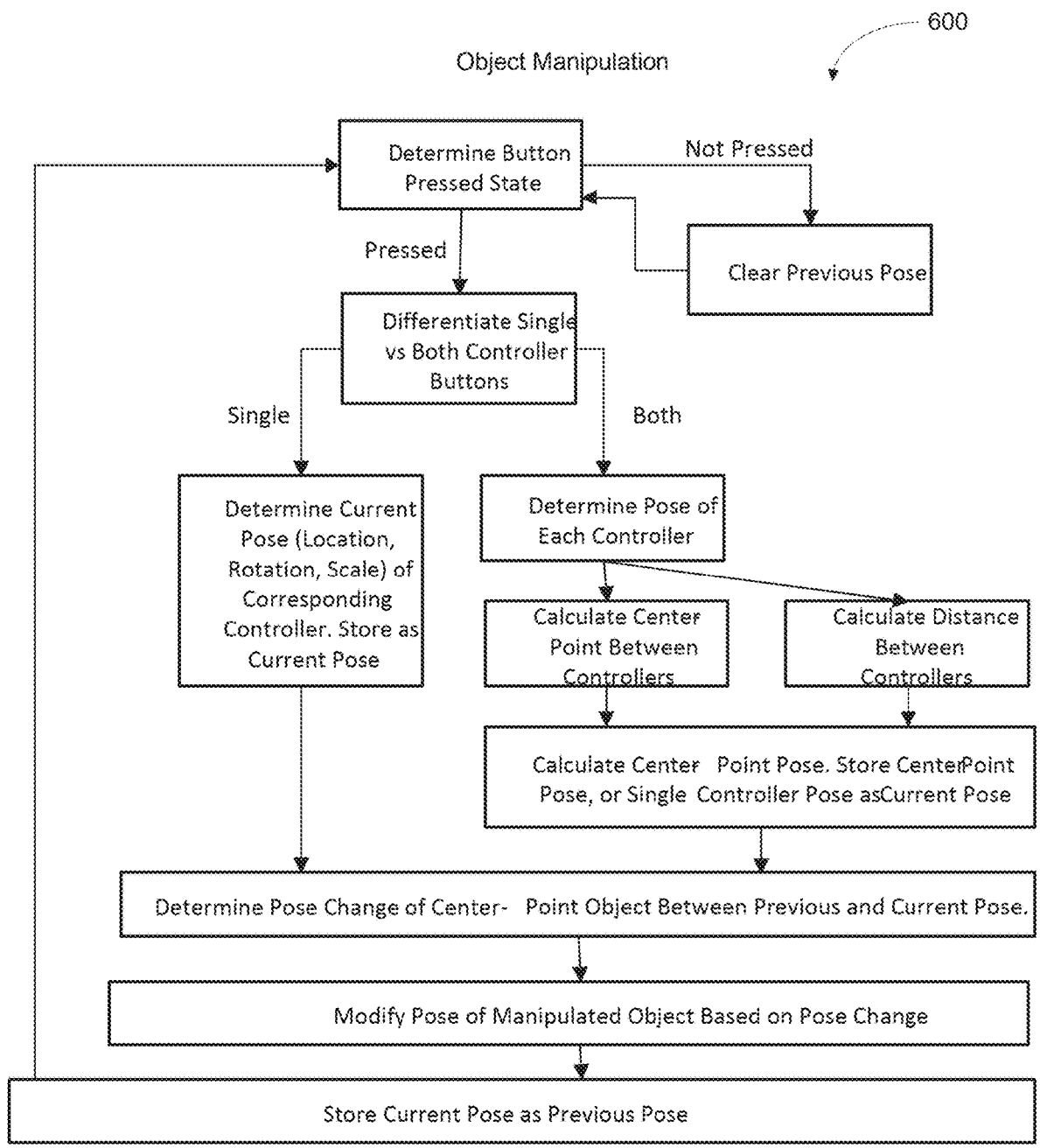
FIG. 6 is a flowchart describing an example method of object manipulation by one or more users, in an IMVR environment, according to an embodiment.

FIG. 6 is a flowchart describing an example method 600 of object manipulation by a user. The method 600 can include recoding, evaluating and/or storing actions, movements, and/or positions of a user, via monitoring properties of a VR controller used by the user, a controller handler associated with a user device (e.g., controller handler 218 of user device 201 in FIG. 2), a renderer associated with a user device (e.g. User specific renderer 216) and/or an IMVR renderer (e.g. IMVR renderer 305) of an IMVR system, according to an embodiment. For example, a controller handler of a user device (e.g., controller handler 218 of user device 201 shown in FIG. 2) can perform one or more functions described in the flowchart 600. As described previously, in some embodiments an IMVR system (e.g., IMVR system 100' of FIG. 1B) can be configured such that user devices are connected to each other in a peer-to-peer manner, without an IMVR renderer. In such embodiments, methods and/or functions described herein as being carried out by an IMVR renderer (e.g., method 600 of FIG. 6) can be performed or carried out by one or more components of the user devices (e.g., user devices 101'-103' of IMVR system 100'). For example, as illustrated in flowchart 600, a user device can include one or two or more controllers, each controller including a button with functionality to be in a pressed state or a unpressed state.

The user device and/or the renderer can receive user inputs via the controller(s) and determine the button press state of each controller. In the case of a single controller, the pressing down of the button can invoke a renderer to determine the current pose of a user within the IMVR environment, including a location, rotation, and scale of the controller. These values can be stored as "current pose". The renderer can determine a change in pose with respect to a center point and calculate a difference between a previous pose and a current pose. Based on the determination of pose change, the renderer can modify the pose of a manipulated object. This process can be carried out iteratively with the current pose being tagged as a previous pose and to be used to compare against the current pose of the next iteration.

In the case of two controllers the renderer can determine the pose of each controller with reference to the IMVR environment and calculate the center point between the controllers and the distance between the controllers. The renderer can calculate, using the center point and the distance, a center point pose that can then be used to determine a pose change as described above. Based on the determination of pose change, the renderer can modify a pose of a manipulated object. This process can be carried out iteratively as described above with reference to the single controller method.

Figure 7:
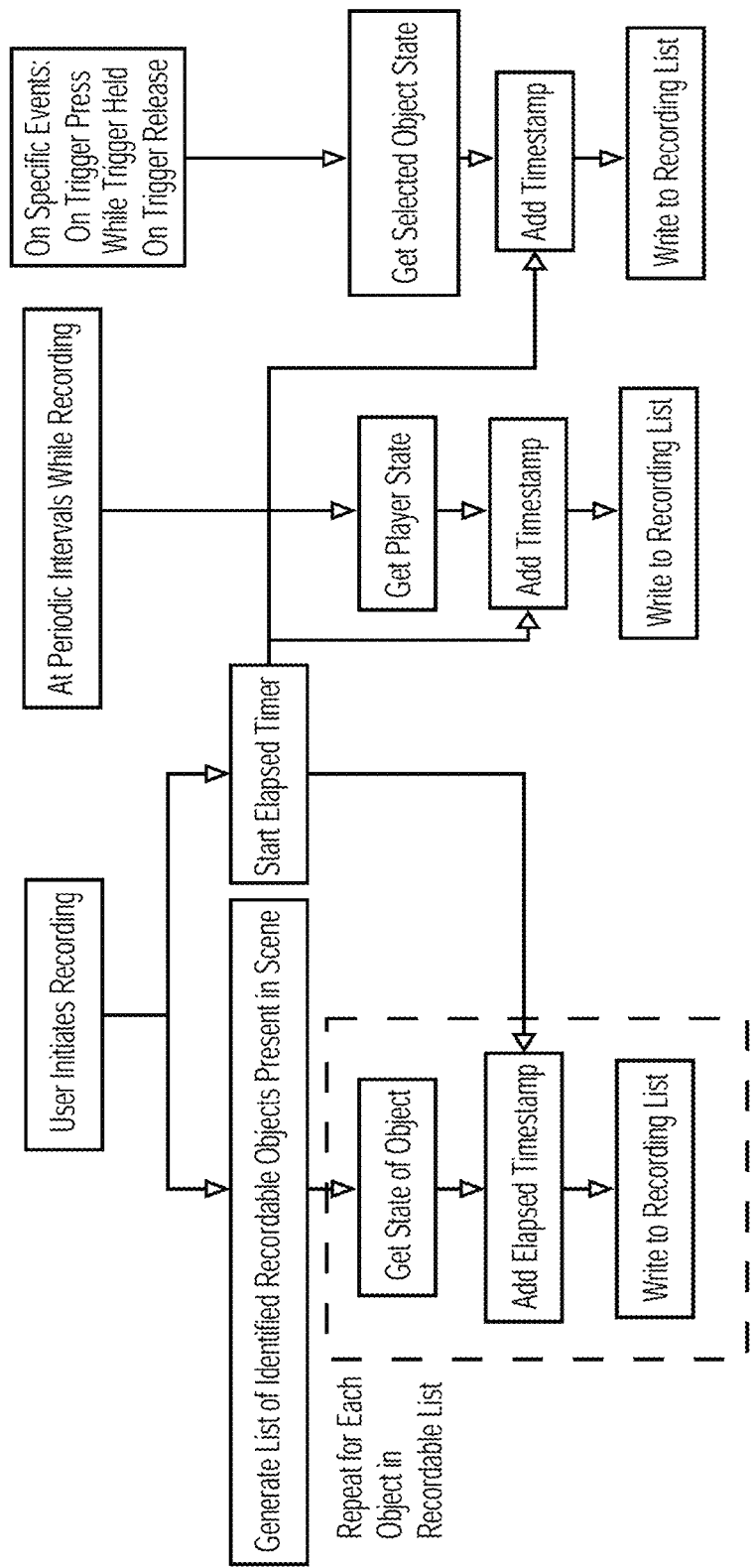
FIG. 7 is a flowchart describing an example method of efficiently recording an IMVR experience when initiated by a user of an IMVR system, according to an embodiment.

In some embodiments, an IMVR system can be configured such that an IMVR experience by one or more users can be recorded and/or played-back. FIG. 7 illustrates a flowchart describing an example method executed by an IMVR system (e.g., a user device (e.g., user device 201) or an IMVR renderer (e.g., renderer 305), as described above) to carryout user initiated recording of an IMVR experience. In some embodiments, the IMVR system can be configured such that the recording can be conducted efficiently and the generated recording file can be configured to be of reduced size, for ease of storage and/or transfer.

Figure 13:
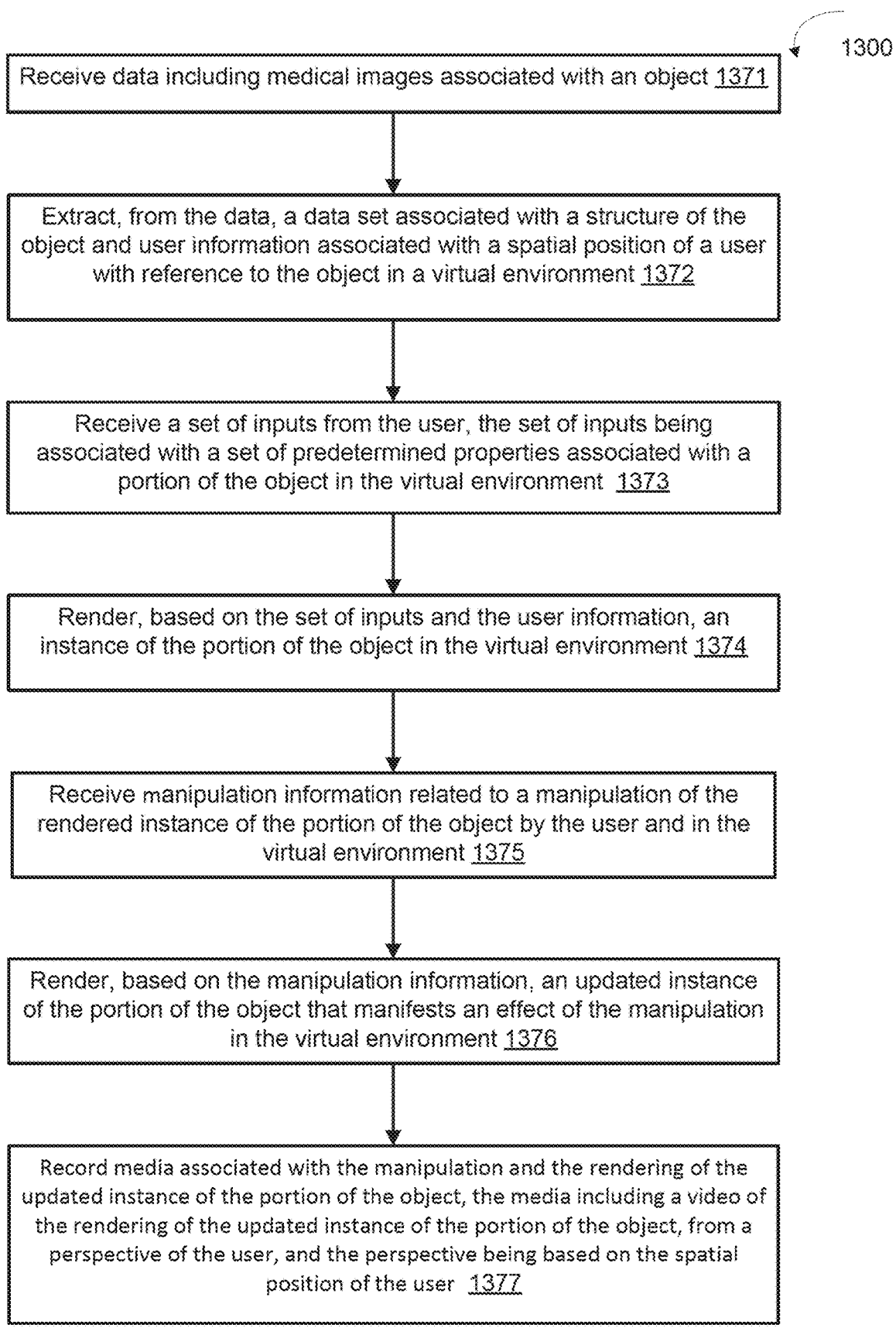
FIG. 13 is a flowchart describing an example method of generating an IMVR environment and recording media associated with the IMVR environment by an IMVR system, according to an embodiment.
Figure 44B:
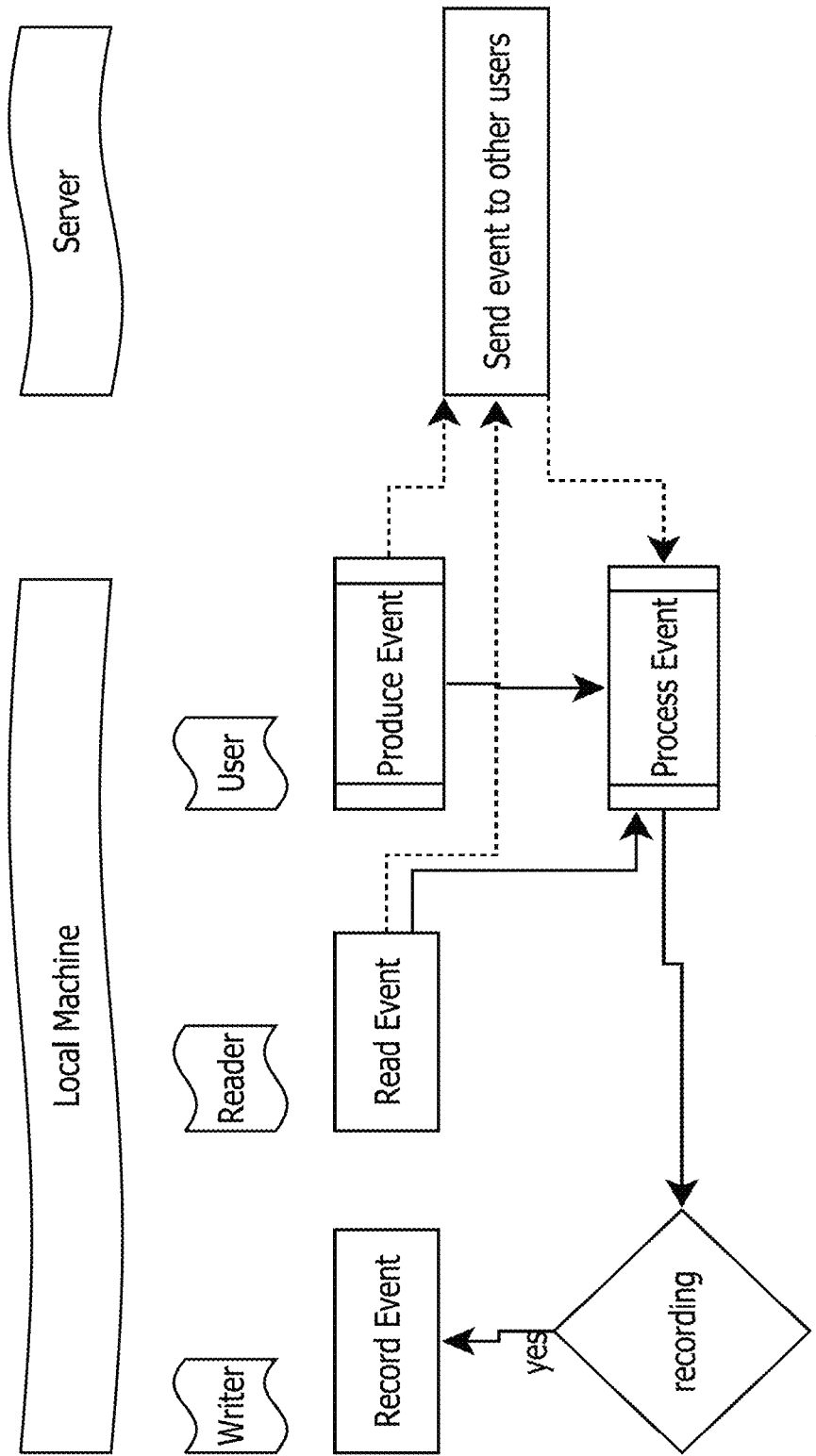
FIG. 44B is a schematic illustration of an example read and write event-based organization of an IMVR system, according to an embodiment.

In some implementations, for example, a user can initiate recording of an IMVR experience and a user device (e.g. user device 201) or an IMVR renderer (e.g. IMVR renderer 305) can generate a list of identified recordable objects available in an IMVR environment associated with that IMVR experience. For each object, the renderer can start a timer. For each time point from a set of time points the renderer can get the state of the object and a timestamp associated with the object at that time point and write the values to a recording list. The renderer can get, at periodic intervals of recording, the player state or the state of the user along with a timestamp associated with the player at that time point. The renderer can be configured to also get an object state at specific events (e.g., on being triggered by trigger events such as a trigger press or a trigger release after being held, etc). FIG. 13 describes an example method of generating an IMVR environment and recording media associated with the IMVR environment by an IMVR system, according to an embodiment. In some implementations, an IMVR renderer or a user device can perform recording in an event-based manner. FIG. 44B is a flowchart describing an example method of event-based handling of IMVR experiences.

Figure 8:
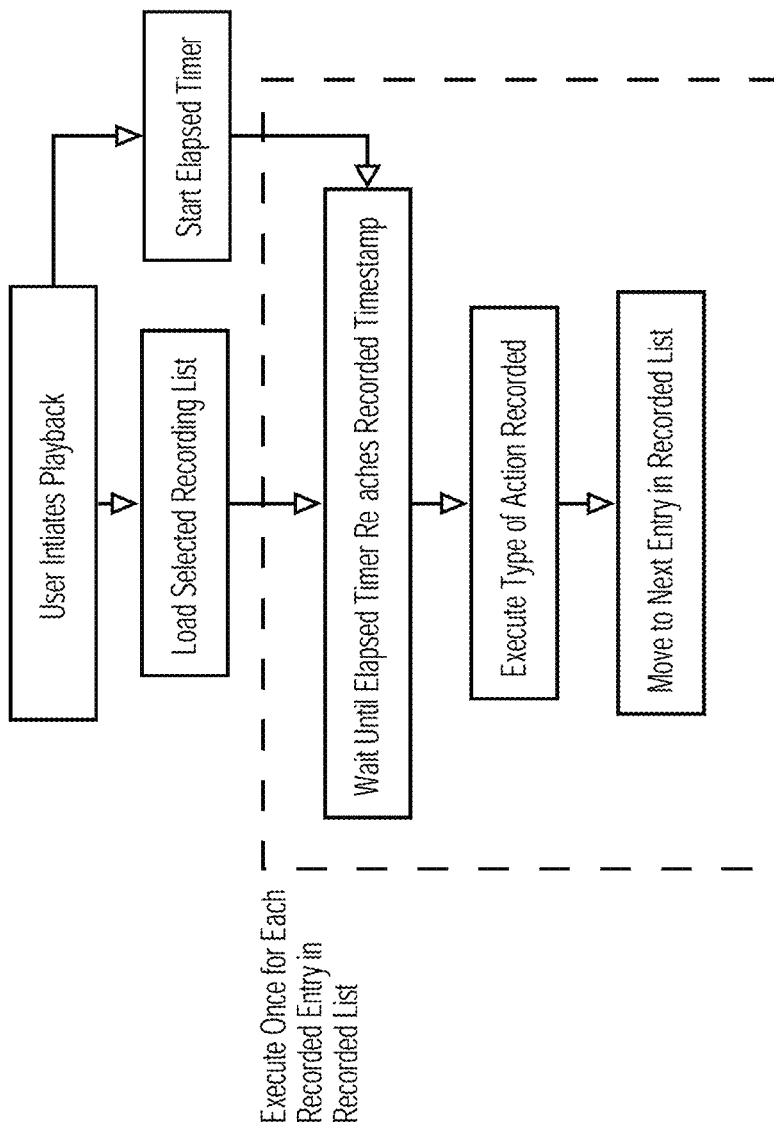
FIG. 8 is a flowchart describing an example method of playing back a recording of an IMVR experience initiated by a user of an IMVR system, according to an embodiment.

In some instances, portions of the IMVR system can be configured to allow playback of a recorded IMVR experience. FIG. 8 illustrates an example method 800 of playing-back recorded IMVR experiences using an IMVR system according to an embodiment. For example, a user device can receive a data set including a recording of an IMVR experience, and as illustrated in method 800 the user initiates playback. The data set can include a recording list including objects, actions, and/or events. Upon initiation of playback, the recording list is loaded onto a user device (e.g., user device 201). The user device starts a time at the point of initiating playback and, at the point of the timer reaching a recorded timestamp, the user device can execute a type of action that has been recorded and is presented in the recording list. The user device can perform execution of events and/or actions in the recording list in an iterative manner. For example, if a recording includes an instructor presenting an instance of a circulatory system of a human body and isolating the heart in a modified magnification, the playback can proceed with presenting each of the objects, events, and/or actions presented by the instructor including any manipulations of the objects (e.g., heart) by the instructor.

In some embodiments, recording and/or playback or an IMVR experience can include information related to a spatial position of a user initiating the recording and/or playback such that one or more objects in the IMVR environment of the IMVR experience can be rendered to the user from a perspective based on the user's spatial position. In some embodiments, recording and/or playback can be managed based on events associated with an IMVR environment or IMVR experience.

Figure 45:
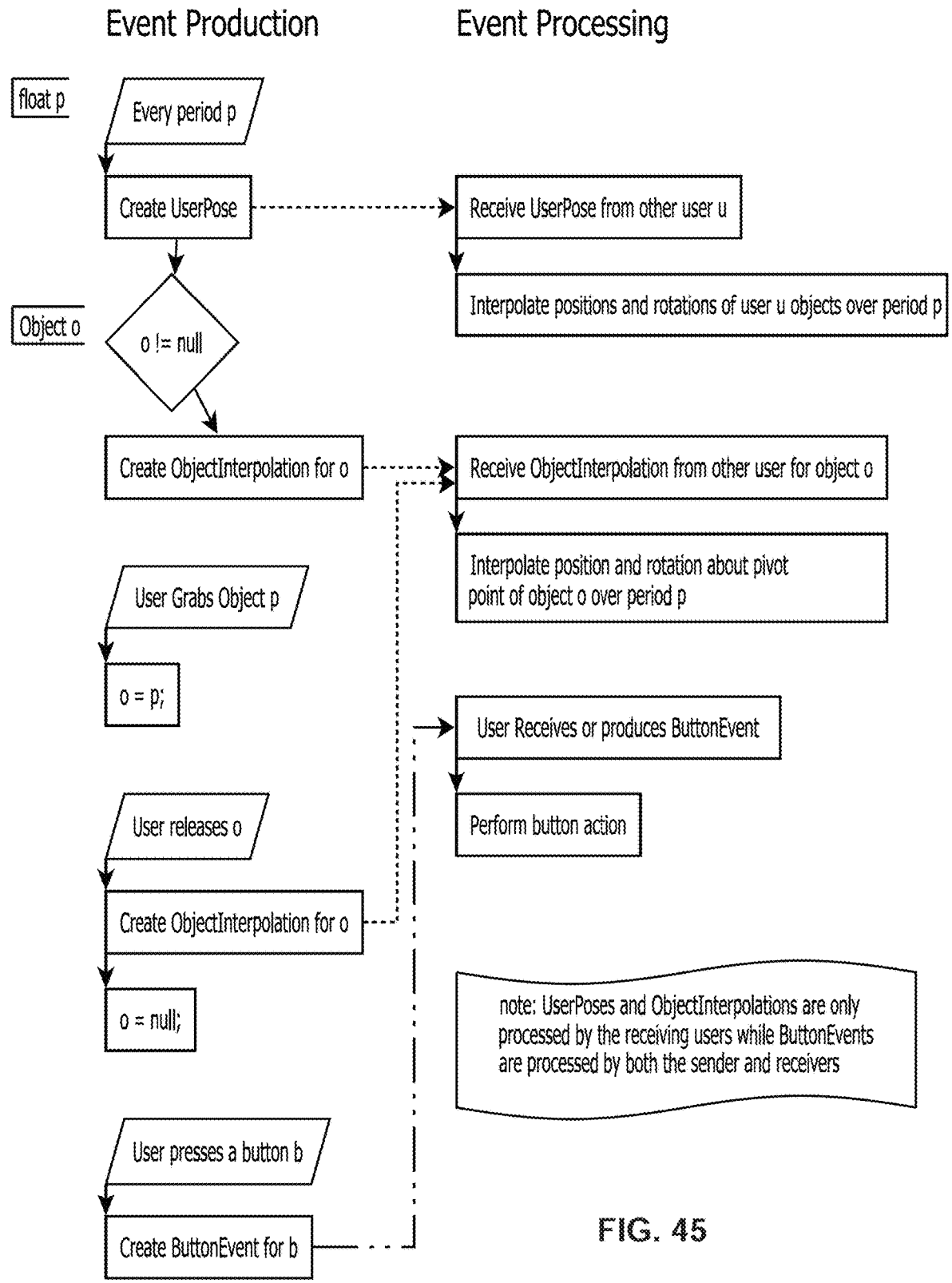
FIG. 45 is a flowchart illustrating an example method to generate and process an event defined in association with an IMVR session, according to an embodiment.

FIG. 44A is a schematic representation of different types of events. FIG. 44B is a flowchart of an example method to implement event based handling of an IMVR system. For example, an IMVR system can include a local machine and a server. The local machine can be a user device (e.g., user device 201) and the server can be an IMVR renderer (e.g., IMVR Renderer 305). The user device can be configured to read events, produce events, process events, check for recording functionality of events, and record events. The user device can communicate with the IMVR renderer to send events (events that are read, produced, processed, and/or recorded at a user device) to other users associated with other user devices and to receive events from other user devices. FIG. 45 illustrates an example flowchart describing a set of events defined related to portions of an IMVR experience and management of the defined events including event production, and event processing. For example, at every period of a predetermined or user determined value p, an IMVR system can create a user pose and process that information along with user poses from other users to interpolate positions and rotations of user objects within the IMVR environment and over that time period. The user device can create an object interpolation event and send it to other users, via the server, to interpolate position and rotation about a pivot point of the object over time period p. As another example, when a user grabs an object or releases an object within the IMVR environment, the events can be processed accordingly and relayed to other user devices. While the above events are described to be relayed to other devices via a server (e.g., via IMVR renderer 305) in some embodiments the events from one user device can be relayed to another user device without a server.

As described previously, in some embodiments an IMVR system (e.g., IMVR system 100' of FIG. 1B, or hybrid IMVR systems that include a server that is configured to only perform limited functions, such as storing data associated with an IMVR system when not in real-time use) can be configured such that user devices are connected to each other in a peer-to-peer manner, without an IMVR renderer. In such embodiments, methods and/or functions described herein as being carried out by an IMVR renderer (e.g. methods or functions associated with or described in FIGS. 7-50) can be performed or carried out by one or more components of the user devices (e.g., user devices 101'-103' of IMVR system 100'). That is, while some embodiments and implementations described in this application include functions shown to be performed by a IMVR renderer, in some other embodiments these functions and operations can be performed by one or more components in a user device (e.g., by the user specific VR renderer 216, or the user state updater 217, or the VR recorder 221 of the user device 201) in a distributed manner. In such embodiments, events produced and processed in user devices can be transmitted directly to other user devices to be locally processed, via a peer-to-peer connection without a centralized server.

In some implementations, network recording can be used in the IMVR system described herein to utilize the low data cost of the multi-user platform offered by the IMVR system to provide a low-cost alternative to a real-time multiuser experience. For example, the IMVR system can be used to record, by a first user(s) and at a first time point, "modules" by saving the data that may be typically sent in real-time in internet protocol (IP) packets to multiple user devices. The saved data can then be played back in a future time point at a second user device. During playback the user of the second user device can have an IMVR experience that is similar to an IMVR experience of being in the same IMVR environment as the first user (s), or "ghosts" (e.g., a virtual representation of a user in the IMVR environment) of the first user(s). Audio can also be recoded in addition to video of objects rendered in the IMVR environment, and played-back simultaneously with the ghost of the first user(s). Audio can be associated with a spatial position of the first user(s) such that at playback the IMVR system can recreate a three-dimensional audio source, making the simulation even more realistic. A pause, play, fast forward and jump back user interface can be available to the user.

Figure 10:
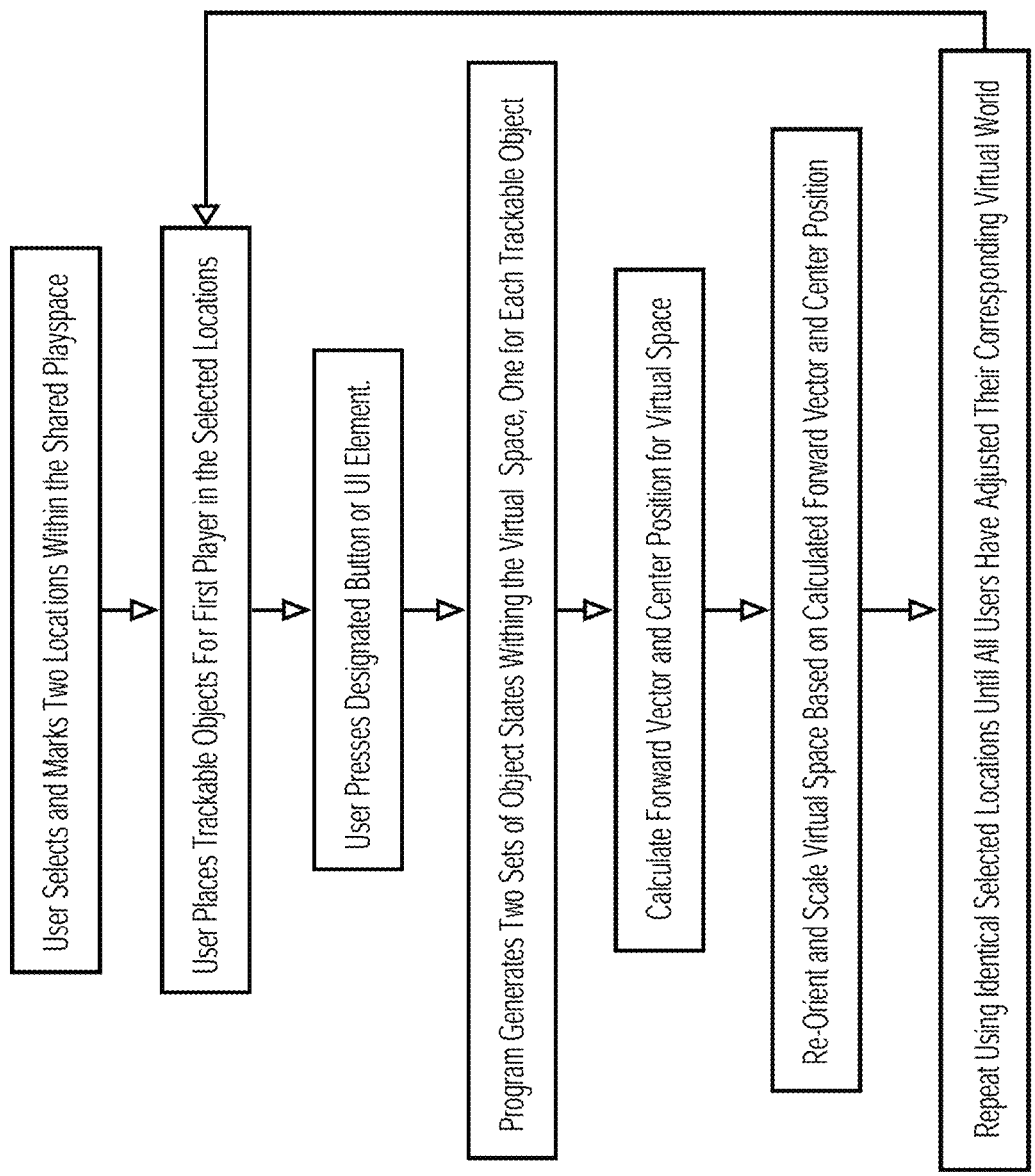
FIG. 10 is a flowchart describing an example method of synchronizing the IMVR experienced by two or more users of an IMVR system by establishing a unified IMVR environment, according to an embodiment.

In some embodiments, as described previously, an IMVR system can be configured such that two or more users can share a synchronized experience of an IMVR environment. FIG. 10 illustrates flowchart 1000 that describes an example method to establish a unified IMVR environment to achieve a synchronized experience among multiple users. The example method 1000 involves a first user identifying and marking two locations in a shared IMVR environment. For example, a first mark can include a center of the shared IMVR environment and a second mark can include a spatial location fixed with respect to the user (e.g., a point at a northeast corner of the shared space). The IMVR system can generate trackable objects and object states associated with the marked locations within the shared IMVR environment. Based on the objects and the object states, the IMVR system can calculate a forward vector and a center position associated with the shared IMVR environment and each of the multiple users sharing the IMVR environment such that each user can recalculate their relative position and orientation with respect to the IMVR environment and accordingly reorient such that their perspectives of the IMVR environment matches their locations.

In use, an IMVR renderer (e.g. IMVR renderer 305) or a user device (e.g. user device 201) described herein can receive a data package associated with a three-dimensional volume object and receive a set of user inputs including spatial information of the user and, based on the data package and user inputs, render an instance of the volume object from the perspective of the user. In some embodiments, the data package can include a spatial data series or three-dimensional volume data obtained, for example, via serial sectioning or serial imaging of a three dimensional object. In some instances the data package can include three-dimensional point cloud information associated with an object (e.g., MEG data). The data can include more than one channel of values, each channel being associated with an array of intensity values. For example, in some instances the data can be obtained from confocal imaging of an object and including multiple channels of data with each channel corresponding to intensity values obtained from imaging a fluorophore (e.g., a channel 1 including data obtained from imaging Green Fluorescent Proteins (GFP) and channel 2 including data obtained from imaging Red Fluorescent Proteins (RFP)). The data package can include look-up-tables (LUTs) for each channel and a sample number associated with the data set to be used for rendering the object. The sample number can be a number of samples associated with the data. The renderer (e.g. a user specific VR renderer 216 of the user device 201 or the renderer 356 of the IMVR renderer 356) can then obtain user information including user position within the IMVR environment, for example a head position and orientation from a head mounted display coupled to the renderer and part of a user device (UD), hand position from a hand controller coupled to the renderer and also part of the user device UD and/or the like.

Based on the data package and user information, the renderer casts rays in the IMVR environment, the rays simulated to be originating from a position of a user in an IMVR environment and traversing along paths in the direction that the user is oriented in the IMVR environment. In some instances, the position of a user can be based on the position of the head mounted display coupled to the user device. The renderer then samples the data set with spatial data for intensity values along the path of the simulated cast rays. In some implementations, the renderer can use predetermined values associated with a front face depth and a back face depth of an object to be rendered and determine a depth of sampling to be either forward of the front face depth or farther behind the back face depth, in which case the renderer may discard the sample and continue to sample iteratively until a region in space within the front face depth and back face depth is reached. In some instances, a renderer can use a near clipping plane to avoid rendering portions of objects that are nearer than the near clipping plane. When a sample is indicative of a ray intersecting with a surface of the object, the renderer, based on a determination of the portion of the object that intersects with each ray, renders an instance of the portion from the user's perspective. The renderer, according to some embodiments, is configured to sample at increasing distances with increasing depth. Sampling distance can be linearly or non-linearly increasing with depth. In some instances a predetermined object boundary location can be calculated and sampling can use this boundary location to render only when the sampled location is within the boundary.

In some implementations a renderer can implement a skipping procedure to increase frame rate (i.e., a rate at which frames are being updated) to increase quality of user experience. A render implementing a skipping procedure can receive user input associated with a skip rate and sample a point in space. If the returned value is a null value indicated by being outside an interested area, the renderer is instructed to obtain a next sample. If the next sample is also determined to be a null value, based on this determination the renderer is instructed to skip the next n samples, n being determined based on the skip rate, and sample the n+1th value. If the n+1th value is also a null value the renderer is instructed to continue sampling along the ray at 2n+1th value and so on. If the returned value at the n+1th sample is not a null value the renderer is instructed to step back to a n-mth value and resample, m being a step-back input provided by the user. In some implementations a user can provide inputs to set the values of n and m based on rendering requirements, nature of object being rendered, and/or processor capabilities of a user device.

In some implementations, a renderer can use a level-of-detail (LOD) property associated with an IMVR environment rendered. The LOD property can be set by a user. In some implementations, when a renderer is sampling values within a large data set that may be time and processor intensive, the render may use the setting associated with the LOD property to sample not the raw data points in the data set but data points in an intermediate data set generated by binning the data set. For example, instead of sampling a 16×16×16 matrix of data points that may be time and/or processor intensive, the render may generate a series of intermediate data sets of decreasing size and order. In this example the renderer may generate intermediate data sets including a 8×8×8, a 4×4×4 and a 2×2×2 data set, each lower order intermediate data sets being generated by averaging over data points and binning the values in the immediately higher data set. The renderer uses a suitably low order intermediate data set to render regions where a high level of detail is not necessary. For example, in some instances, a low order data set can be used when rendering objects at an increased distance from a position of a user in an IMVR environment, or when rendering details in a background, or when rendering details of objects that are not in the focus of a user (when foveation of the user is tracked). As another example, when a sample is suspected to be returned as a null value, a low order data set can be sampled first and, if the returned values are not null, a renderer can be instructed to iteratively sample in a higher order intermediate data set for more level of detail until a suitable LOD is reached. In some instances, a renderer may use a suitable LOD in one user device to match the appearance of a rendered object with that of an object rendered in another user device. For example, a user device with higher display resolution may use a lower LOD to match a user device with lower display resolution and vice versa.

In some implementations, sampling at further distances in depth using a higher order data set with high LOD can give rise to noise in rendering an IMVR environment. In such instances a renderer can be instructed to stop sampling at a particular level of detail (and switch to a lower level of detail if sampling is beyond a predetermined depth). In some implementations this may allow a user to increase sampling rate before the frame rate drops due to processor capacity, increasing user experience. Such a procedure (e.g., sampling a first third of samples at a highest LOD 0 (i.e., no averaging), sampling a second third of samples at LOD 1 (i.e., one level of averaging including averages of samples), and sampling a last third of samples at LOD 2 (i.e. 2 levels of averaging, including averages of average of pixels) can allow a user to receive more detail up-front, good detail in the intermediate distance and lesser detail at farthest distances with a fast rendering. In some implementations, as sampling distance (i.e., distance between adjacent samples in space) can be increasing with increasing depth, if a sampling distance is comparable to the distances associated with pixel values of an intermediate data set with an intermediate LOD, the averaged pixel value from the intermediate data set can be a better representative and quicker to sample from.

In some implementations, a renderer can be instructed to terminate sampling at an earlier point based on opacity or transparency of an object based on an alpha value. In some implementations the sampling can be dynamically set to match a desired frame rate of rendering (e.g., a desired frame rate of 60 fps to increase user comfort). In some implementations the renderer can implement foveated rendering where only the foveated area of focus of a user is rendered with high quality, reducing processing load while minimally or not changing user experience.

In some implementations, sampling can be offset to reduce wood graining effect, This is achieved by sampling from a texture composed of "random noise" to get an offset value. These randomized ray sample positions between distinct bands within the volume allow for a more distributed sampling of the data. For example, a renderer can implement a procedure to randomly offset a start position of sampling and/or casting rays. When sampling along radially increasing distances, a second ray is slightly offset from a first ray and samples are at particular radial distances. Implementing offsetting a renderer can sample at odd distances instead of at fixed incremental shells of sampling distances in relation to the user. Such a sampling at random positions with respect to fixed radial shells, also known as splattering, can avoid a so called "wood graining effect". The calculations can be made with respect to a head position of a user and at a volume scale relative to the user. In some implementations, splattering can also be dynamically set with respect to the variable distance of sampling, and/or a scale of the object sampled. The scale of an object can be defined by a scaling factor.

Figures 41A, 41B:
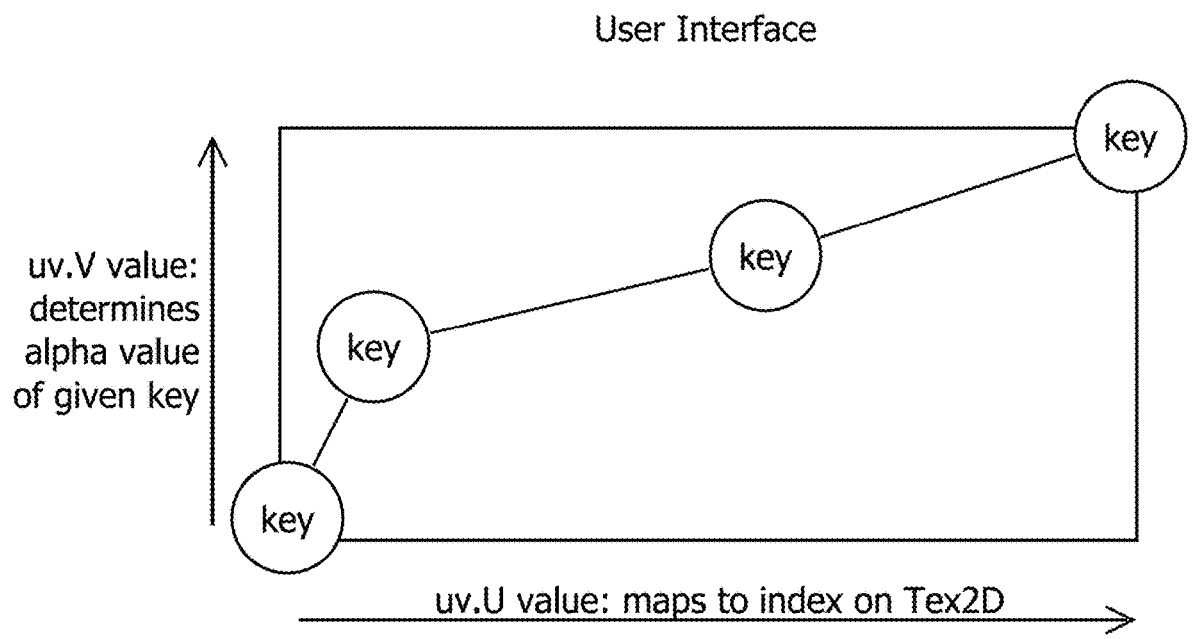
FIG. 41A is a schematic illustration of an example user interface with a set of object properties represented by a set of keys operable by a user via the user interface, according to an embodiment.
FIG. 41B is a schematic illustration of an example key associated with the user interface of FIG. 41A, as used by an IMVR system to render a volume object, according to an embodiment.

In some instances, the three dimensional points in space when sampled and determined to be within the boundary can return an intensity value, which can be mapped to one or more LUTs associated with properties of the object. For example, the user may have selected a combination of keys (e.g., 2 keys) to represent that portion of the object. Each key can include a position value with respect to the object, a color value, and a transparency value and the keys being associated with a LUT. A renderer can use the LUT(s) to return a mapped value that can be used to render a pixel corresponding to an instance of a portion of the object (e.g., a surface texture associated with the object). FIG. 41A is a schematic illustration of a user interface showing an example set of object properties represented by a set of keys, and FIG. 41B is a schematic illustration of an example key, as used by a renderer to render a volume object, according to an embodiment.

As an example, a user can select and set values associated with keys via the user interface of FIG. 41A. The definition of color keys can be based on their position on the mapping shown in FIG. 41A based on which a LUT is generated. The axis including scaled uv.V values represents transparency value (high opaque, low transparent) of a key and the axis including scaled uv.U values represents index value of the key. For example if a key represented a white color key, a user can slide the key on the space and increase to a high white value with high opacity or a low white value. A renderer can interpolate values between multiple keys to generate a LUT. A user can sample through a volume and assign a value to an object using any suitable number of keys (e.g., a user can select a representation of bone using 3 keys and muscle using 10 keys). The number of keys can be any suitable integer value.

A user can adjust keys associated with an object and the IMVR system can be configured to propagate the adjustment to other user devices such that the change in appearance of the instance of the object rendered in the user device of the user adjusting the keys is mimicked in the instances of the object rendered in the other user devices, as described herein. For example, in some implementations, as one user moves keys, muscle data disappears and the IMVR system can send the information of location of the key and color, position and transparency values to the other user devices in the IMVR system, such that the renderers associated with each of the user devices can calculate the LUT locally to mimic the appearance of the instance of the object in the first user device. In some instances a data set can be associated with a preset LUT save d with the data set. Adjusting keys can be configured to generate effects in the LUTs over the sampling time of a renderer (e.g., 200 msec). Every user device can be configured to calculate the LUT in the same way to get a unified data representation for users in an IMVR session, sharing an IMVR environment. Calculating a LUT can be agnostic to hardware associated with each user device.

In some implementations, a user can be provided a set of control tools or data adjustment tools (e.g., sliders) to fine tune and update, in substantially real time, the instance of the object without modifying a LUT such that any manipulations and/or modifications made by one user can be propagated to other users in substantially real-time. A manipulation at one user device can be associated with a generation of a manipulated data package that can include the manipulation information. The user device can be configured to transmit the manipulated data package to the other user device to propagate the manipulations made by the user to other user devices. As an example, the user can be presented with a color key slider to manipulate key selection and key positioning to affect the appearance of the object rendered, as described below. For example the user interface (similar to user interface of FIG. 41A) of an IMVR system in a user device (e.g. user device 201 in FIG. 2) can include a Max-Min slider configured to stretch a histogram of intensity values associated with the data set underlying a rendered object such that the full LUT can be used to visualize a portion of the object that includes intensity values that map onto a smaller portion of the intensity histogram associated with the data set. In some instances, the user interface can include a threshold slider used to receive user input related to a cut-off for visualization.

As described above, the user interface imparts a user the ability to manipulate the range of data shown for a given data set and associated with an object rendered in an IMVR environment and have the manipulation reflected across instances of user devices in the session. In some implementations, the IMVR system can be configured to include user interfaces that enable the users to manipulate properties associated with a rendered object over a set of value ranges found within the data.

For example, a user can highlight bone in a CT scan to accent cracks in a geode. As an example implementation, at the user interaction level, the IMVR system can provide a user with a simple user interface, through which a user can adjust the data shown by moving sliders. One slider can be configured to allow for the adjustment of transparency (alpha value). For example, in a user interface similar to that shown in FIG. 41A, a slider can be configured to adjust a key in the uv.V axis. A series of sliders can be configured to allow the user to choose a smaller data range to view within the full data range. Several preset color gradients can be applied with a single click, to better visualize the data set. Alternatively, in an implementation, an advanced menu can be used to create a color gradient of a user's own design. A user in an IMVR session can, for example, color muscle red and bone white and omit other data, within a given CT.

The IMVR system is configured such that adjustments made to the sliders, the color key positions, and/or the color of the keys are propagated to other users of the IMVR session. The IMVR system can then invoke the user devices associated with the other users to render updated instances of the object such that the same color mapping is generated to result in a comparable visualization across users.

Figure 42B:
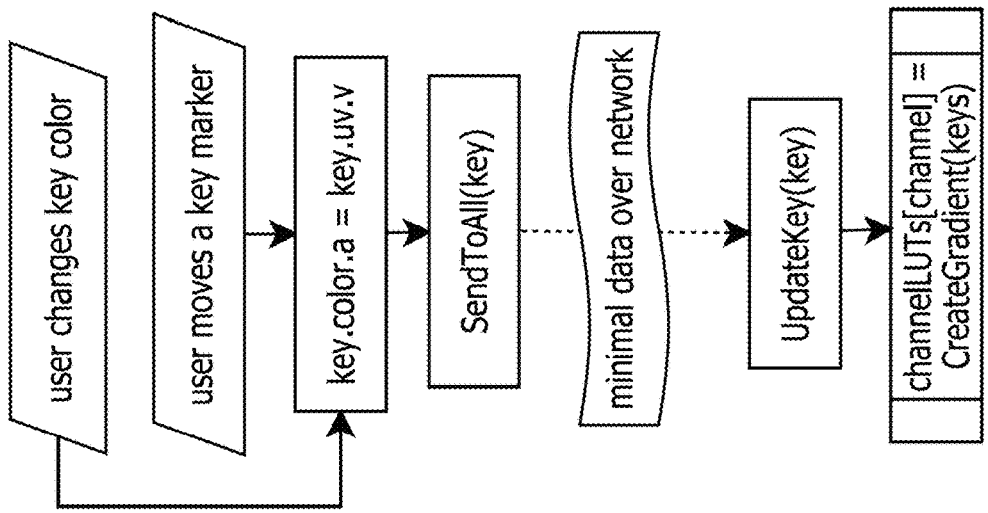
FIG. 42B is a flowchart describing an example method of implementing a user manipulation of an IMVR environment via adjustments of keys and propagating to the user devices the adjustments of keys, using a strategy of minimal data transfer over a network, to in an IMVR system according to an embodiment.
Figure 42A:
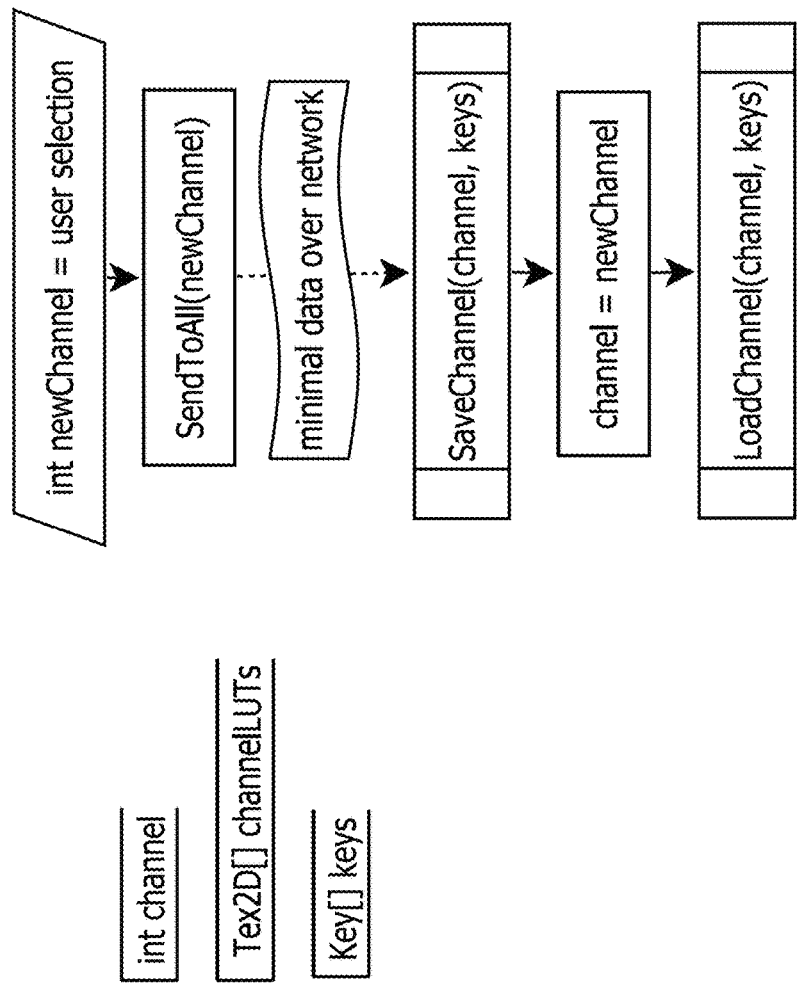
FIG. 42A is a flowchart describing an example method of user selection and sending, to user devices, a new channel of data over a network.

FIG. 42A is a flowchart describing an example method (e.g., executed by a renderer or a user device) implementing a user selection of a new channel of data, sending of the new channel of data to other user devices, including a second user device, using a strategy involving sending minimal data over a network, and saving of the new channel of data. This new channel of data can be loaded in a second user device that received the data.

FIG. 42B is a flowchart describing an example method (e.g., executed by a renderer or a user device) implemented when a user associated with a first user device changes a key color to manipulate a rendering of an object. When the user moves a key marker (for example a key marker as shown in FIG. 41A) the values associated with the new position of the key marker are registered by the renderer and data related to the new positions of the keys is transmitted over a network to the other user devices in the IMVR session that the first user may be part of. The data related to key positions is transmitted in a strategy involving minimal data transferred over the network. The user devices that receive this data transmitted by the first user can then update the set of keys associated with their respective renderers using a procedure to create gradients, an example of which his shown in FIG. 42C.

Figure 42C:
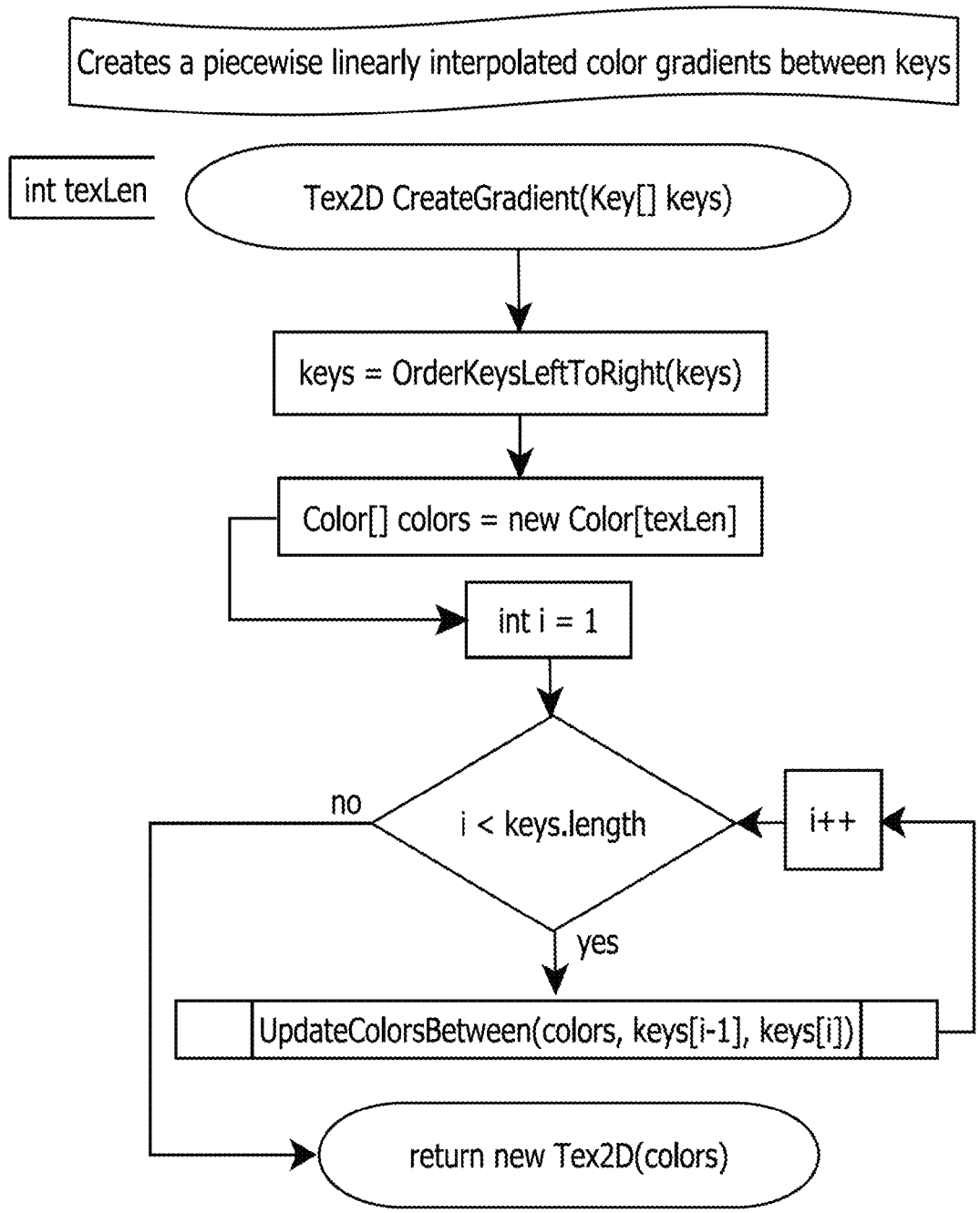
FIG. 42C is a flowchart illustrating an example method to generate a colorized rendering of a volume object using a set of keys in an IMVR system, according to an embodiment.

FIG. 42C is a flowchart illustrating an example method (e.g., executed by a renderer) to create a color gradient to render a colorized instance of a volume object using a set of keys, in an IMVR system. When more than one key is set by the user or received by a user device in the IMVR system, the renderer can be configured to interpolate between the keys (e.g. linearly interpolate or non-linearly interpolate) to generate a color gradient between the keys as described in FIG. 42C. For example, the keys can be ordered from left to right, and the color value of each key can be used to generate a list of colors in-between pairs of keys generating an updated colors listing. The updated colors listing can be used to invoke a procedure configured to generate an updated color gradient definition, an example of which is shown in FIG. 43.

Figure 43:
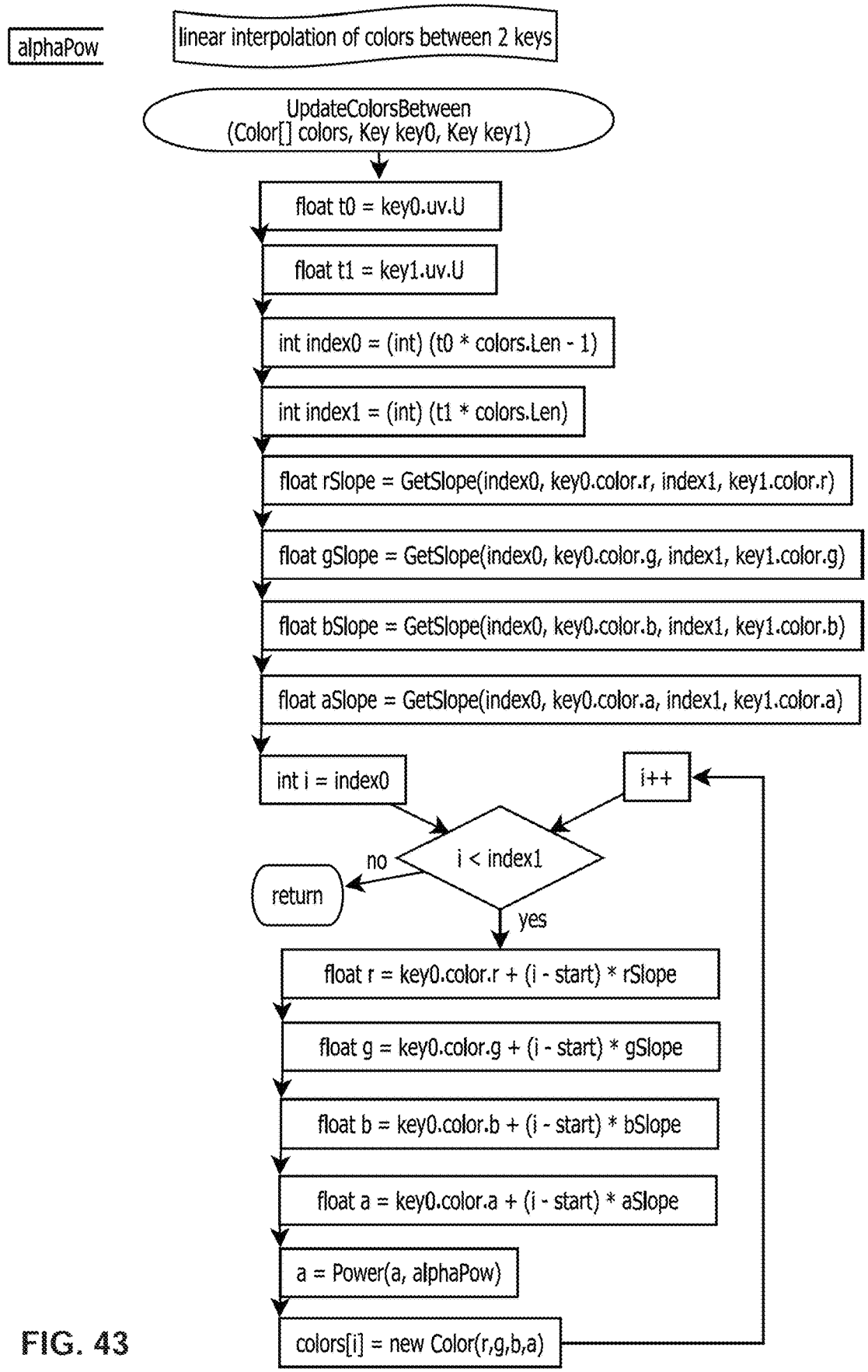
FIG. 43 is a flowchart illustrating an example method to generate a colorized rendering of a volume object by interpolating information associated with a set of keys, according to an embodiment.

FIG. 43 is a flowchart describing an example method to generate a new color gradient definition by interpolating information between a pair of keys (key 0 and key 1) to generate an LUT. For example, a renderer can receive information associated with the pair of keys. The keys include a color, position, and transparency value, and each key has a red (e.g., key0.color.r), green (e.g., key0.color.g), blue (e.g., key0.color.b), and alpha color (e.g., key0.color.a) component. The renderer can generate a slope value between pairs of keys (e.g., a rSlope associated with the red color component of key0 and key1, a gSlope associated with the green color components of key0 and key1, etc.) The renderer can update the red, green, blue and alpha (a) color components of key 0 with updated values based on the rSlope, gSlope, bSlope and aSlope to generate a new color using the updated values.

Figure 11:
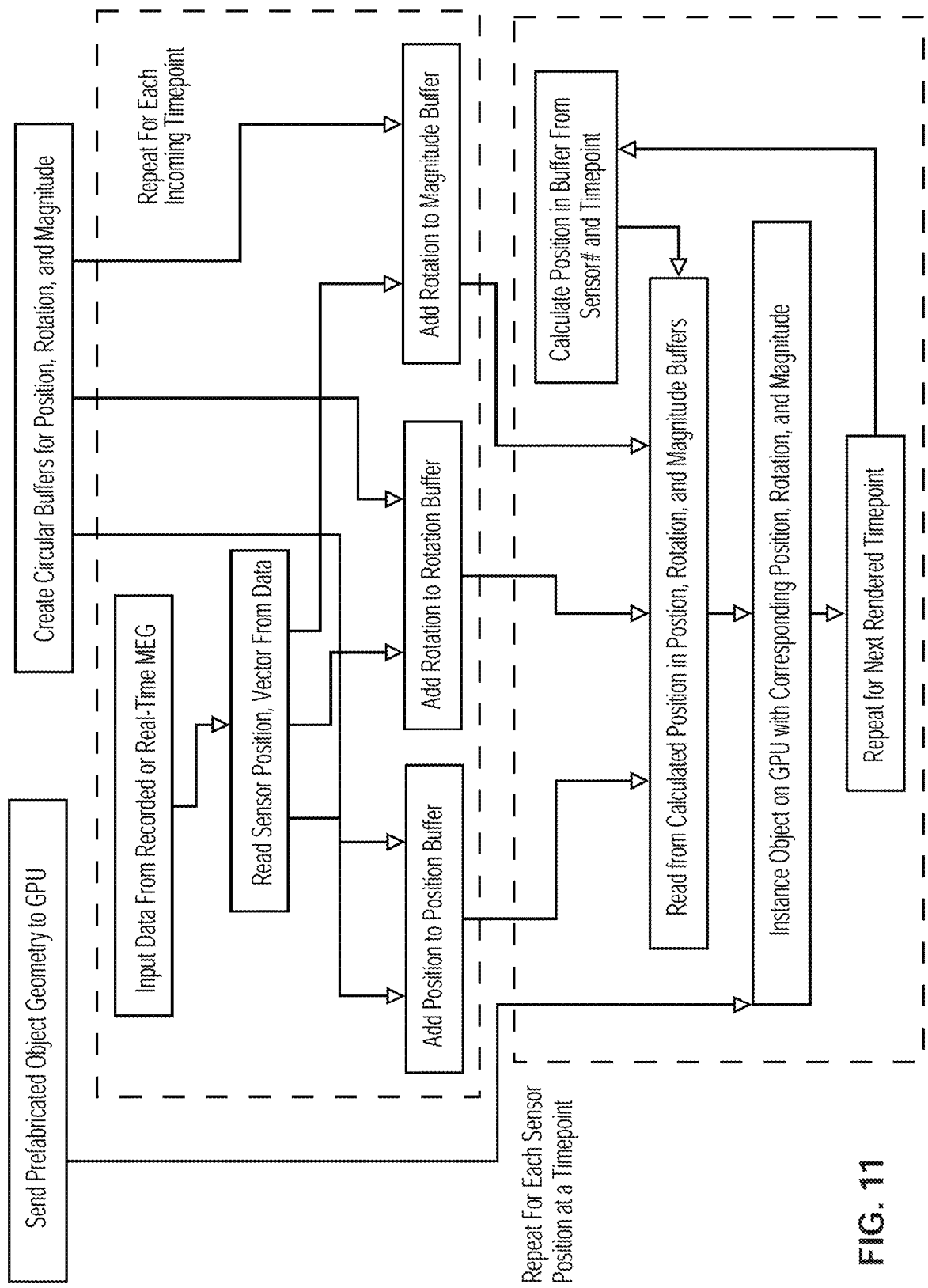
FIG. 11 is a flowchart describing an example method of using MEG data to generate an IMVR experience using an IMVR system, according to an embodiment.

In some instances, an IMVR system can be configured to read imagery generated from magnetoencephalography (MEG) and use the data to generate rich IMVR environments that can be used to visualize and/or probe data for several diagnostic, research, educational, and/or training purposes. FIG. 11 illustrates an example method 1100 that can be used to generate a rich, interactable IMVR environments for visualizing MEG data using IMVR systems of some embodiments.

Figure 47A:
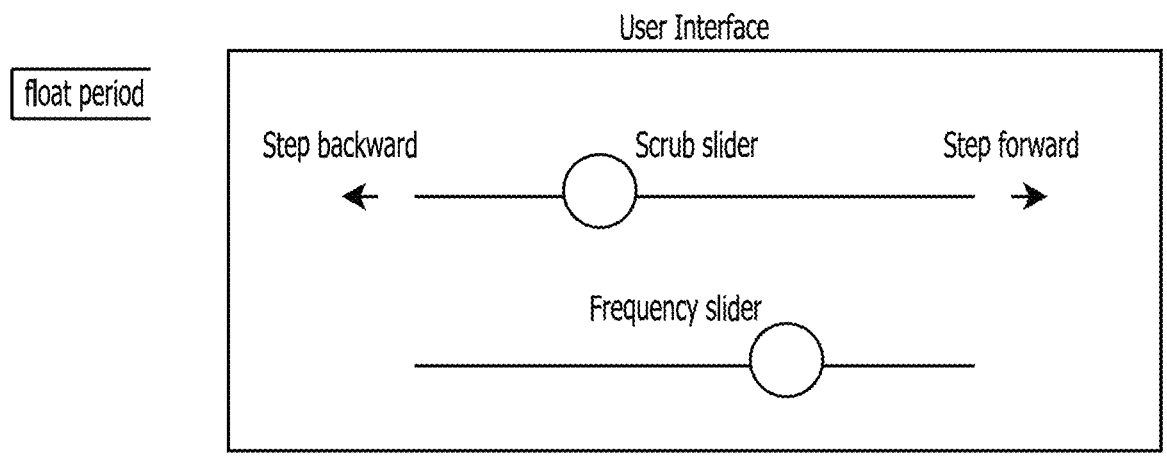
FIG. 47A is a schematic representation of an example user interface of an IMVR system configured to allow a user to navigate through a data set associated with MEG data and the rendering of an object included in the MEG data, according to an embodiment.
Figure 47B:
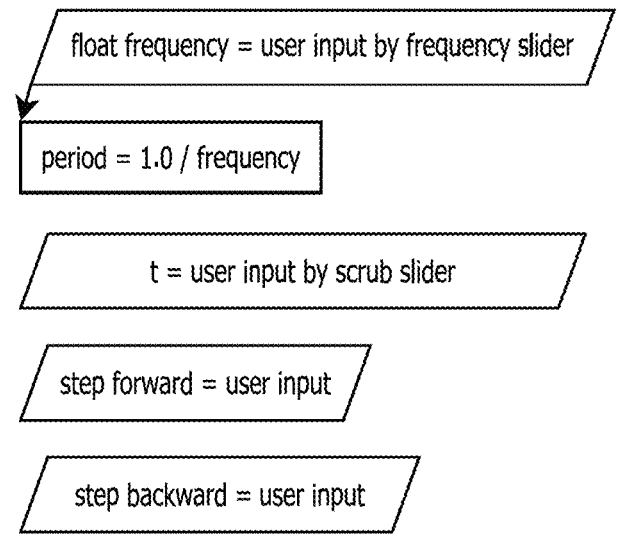
FIG. 47B is a flowchart describing an example method of implementing the features in the user interface of FIG. 47A.

A user can manipulate the data in 3D space i.e. rotation and scale, as well as traverse through time points using a set of features such as a playback feature, step feature or a scrub bar. FIG. 47A, shows an example user interface that can be used to navigate through an instance of a rendering of MEG data. As shown in the example, a user interface can include forward and backward navigation controls to step forward and step backward through distance in the rendered IMVR environment. The user interface can include a scrub slider and a frequency slider that a user can adjust to set a scrub property (clean the rendered instance to remove undesired portions of an object in the IMVR environment) and a frequency of updates to the rendering associated with the data, FIG. 47B is a flowchart describing an example method to implement the inputs provided by the user via the user interface of FIG. 47A.

In some embodiments, IMVR systems can be configured to receive datasets obtained through Magnetoencephalography imaging and generate visualizations of the data in three dimensional space and time. Magnetoencephalography scans (MEG) can be used to visualize electrical activity in the brain by measuring the dipole moment direction and magnitude (vector) at the cortical surface. This data can then be viewed in an IMVR environment giving a three dimensional perspective of this electrical activity. For example, a MEG data set captured while responding to an auditory stimulus can be viewed in VR, tracing the pathway of auditory information through the brain. Vector information can be represented by a model object, e.g., as a "tear drop" shape that changes length and color with magnitude, i.e., increase brain activity in a certain area will appear as a hotter colored, longer tear drop. Point cloud data can be represented as any shape and color.

Figure 48:
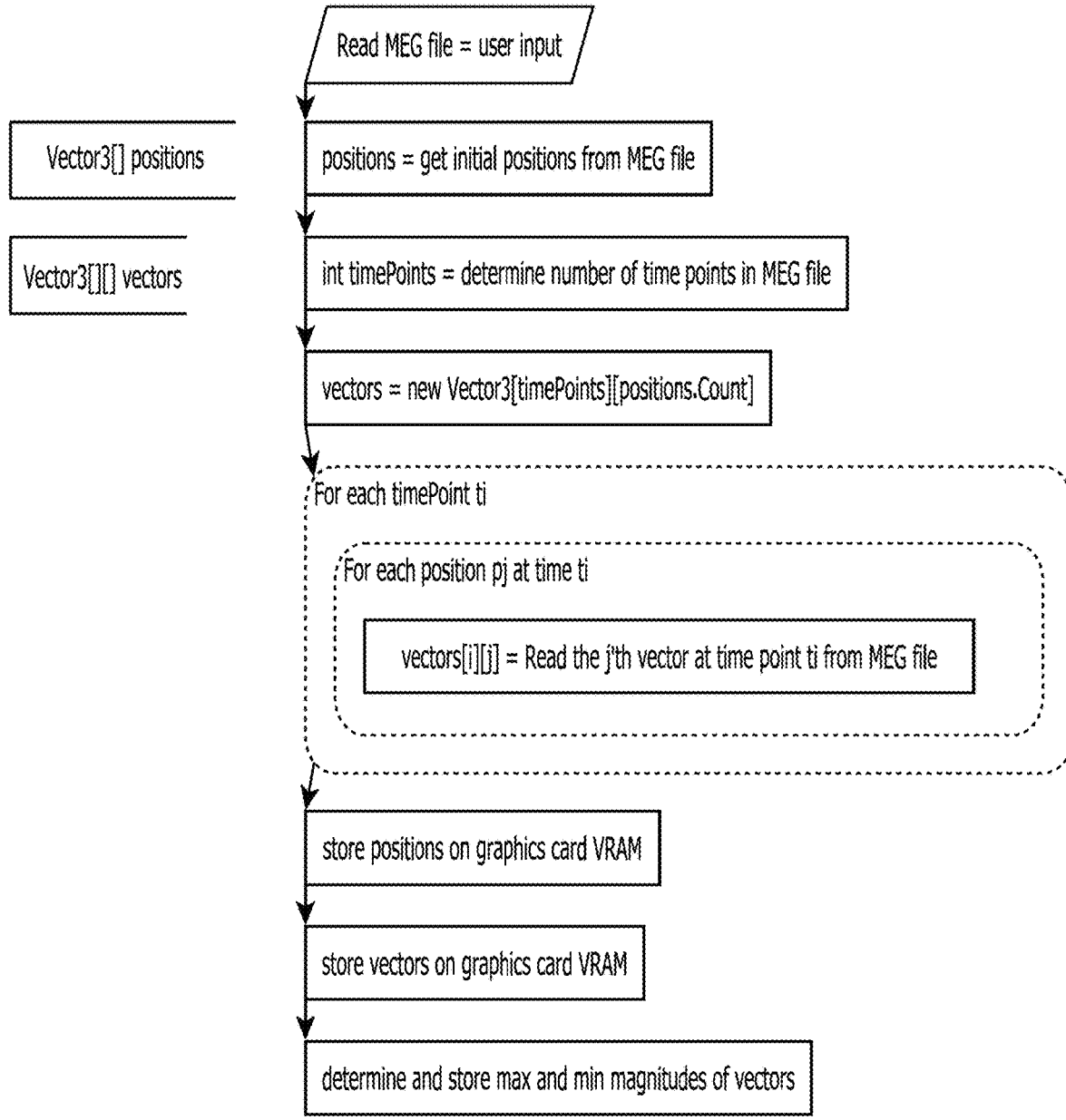
FIG. 48 is a flowchart describing an example method of implementing procedures related to reading a MEG data set and extracting information from the MEG data set to render an instance of an object included in the MEG data set, according to an embodiment.

FIG. 48 is an example method describing reading and rendering spatial data obtained from MEG using an IMVR system as described herein. As shown, for example, in some implementations, a user device in an IMVR system can receive data associated with MEG from external sources and extract vector data corresponding to a predetermined set of points. The vector data can include initial positions of the predetermined set of points and a set of time points and changes in positions as a function of time. The predetermined set of points (e.g., 7000 points in space, each point associated with a three dimensional vector) can be related to magnetic dipole moments associated with localized neural activity. Each point in the set of points can be associated with properties including a position (or origin) property, a rotation property, a magnitude property, and a time property. Each point can include a set of values corresponding to each property. For example each point can be associated with a series of time points, and a set of origin, rotation and magnitude values associated with each time point. The vector can be read and stored in a volatile memory (e.g., VRAM) associated with the user device along with a maximum value and a minimum value associated with the vectors, as shown in FIG. 48. The renderer of the user device can include a set of buffers including a position buffer, a magnitude buffer and a rotation buffer, such that a set of points with the associated properties and values can be read from the extracted vector data, added to the corresponding buffers, and rendered in association with an instance of a volume object in an IMVR environment, as shown in FIG. 11.

Figure 46B:
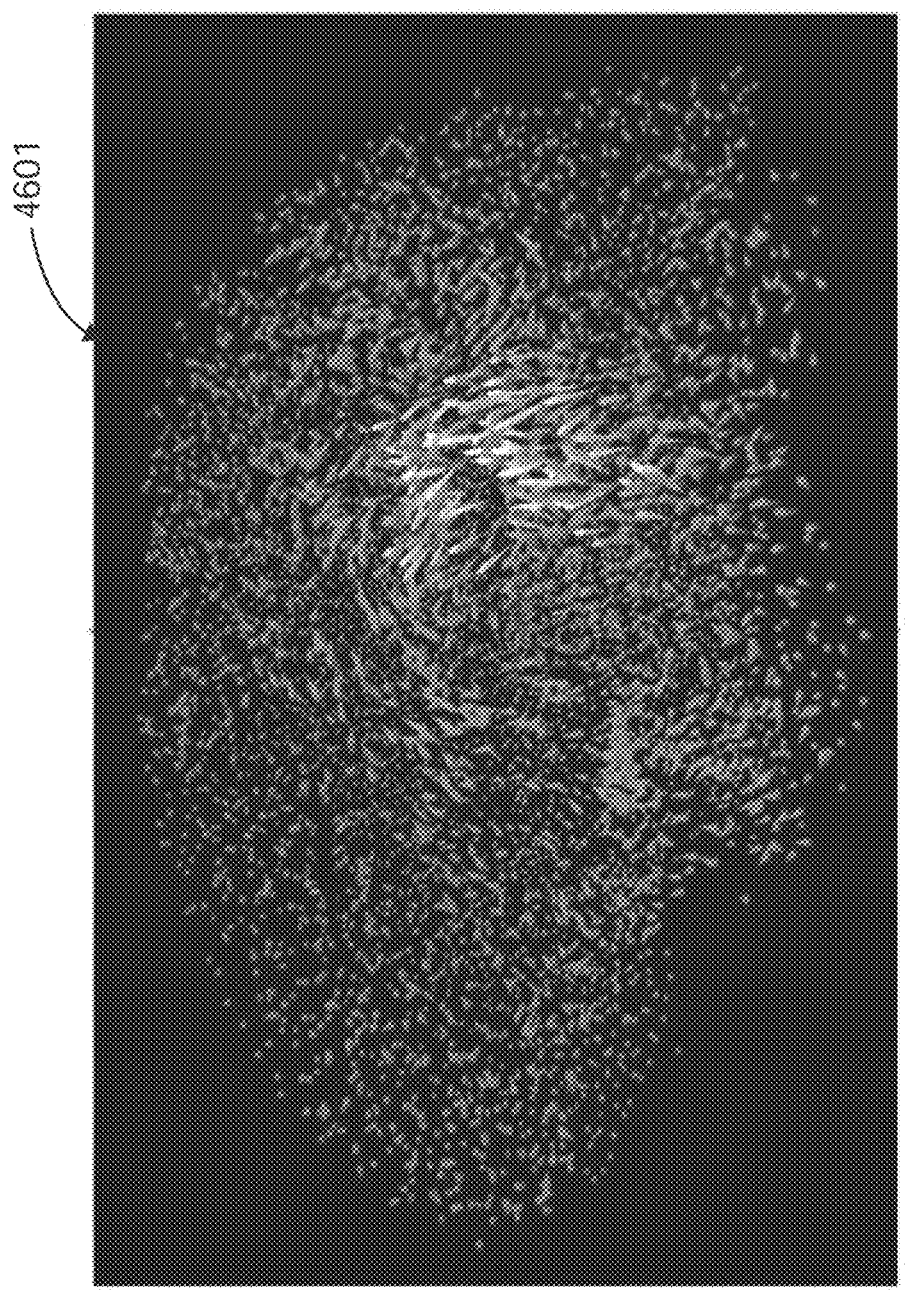
FIG. 46B is an illustration of a perspective view of an IMVR environment including a representation of data obtained via magnetoencephalography using several instances of the model representation object shown in FIG. 46A, according to an embodiment.
Figure 46A:
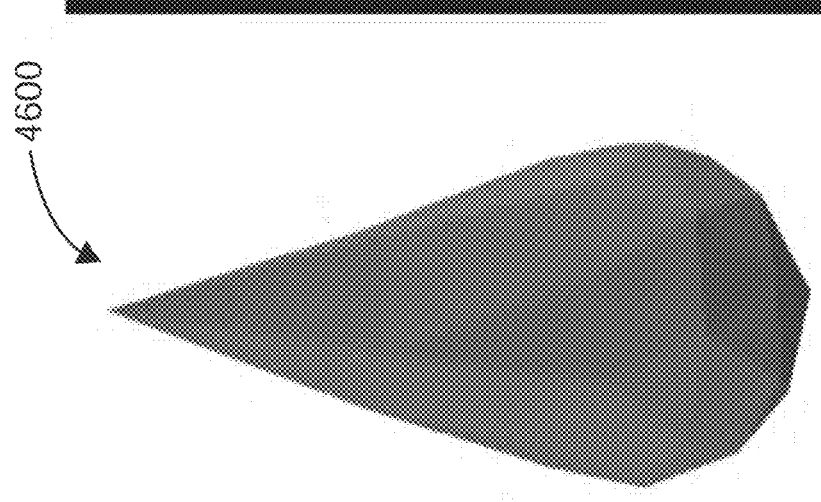
FIG. 46A is an illustration of a model representation object shaped as a tear-drop.

In some embodiments, the points can be rendered by being represented by a model object. In some implementations the model object can be an artist rendered mesh object with predetermined attributes or properties including color, appearance, texture, shape, size, and/or structure. Properties can be mapped to values associated with the points using a look-up-table. FIG. 46A illustrates an example model object 4600 which is a mesh object shaped as a teardrop. FIG. 46B illustrates a perspective view of an example visualization 4601 in an IMVR environment, of MEG data including several thousand points, the points being represented by several thousand instances of the model object 4600.

The visualization 4601 represents neural activity at a time point "t" obtained from vector data and associated with the instances of the model object, each vector including a position, direction, magnitude, and time, and being associated with one instance of the model object with corresponding properties including position, orientation, length, and color. The position or origin property of the several thousand instances of the model object 4600 can remain fixed over varying time and the properties of orientation, length and color can be variable over time depending on information obtained from the corresponding vector magnitude and vector direction of the vector at the associated position in the vector data. The properties of color and length of each instance of the model tear-drop shaped object 4600 object are shown to be varied based on the vector magnitude of the associated vector in the vector data, with larger vector magnitude being associated with larger length of the instance of tear-drop shaped model object and a lighter color, each selected based on a suitable look-up-table.

Figure 49:
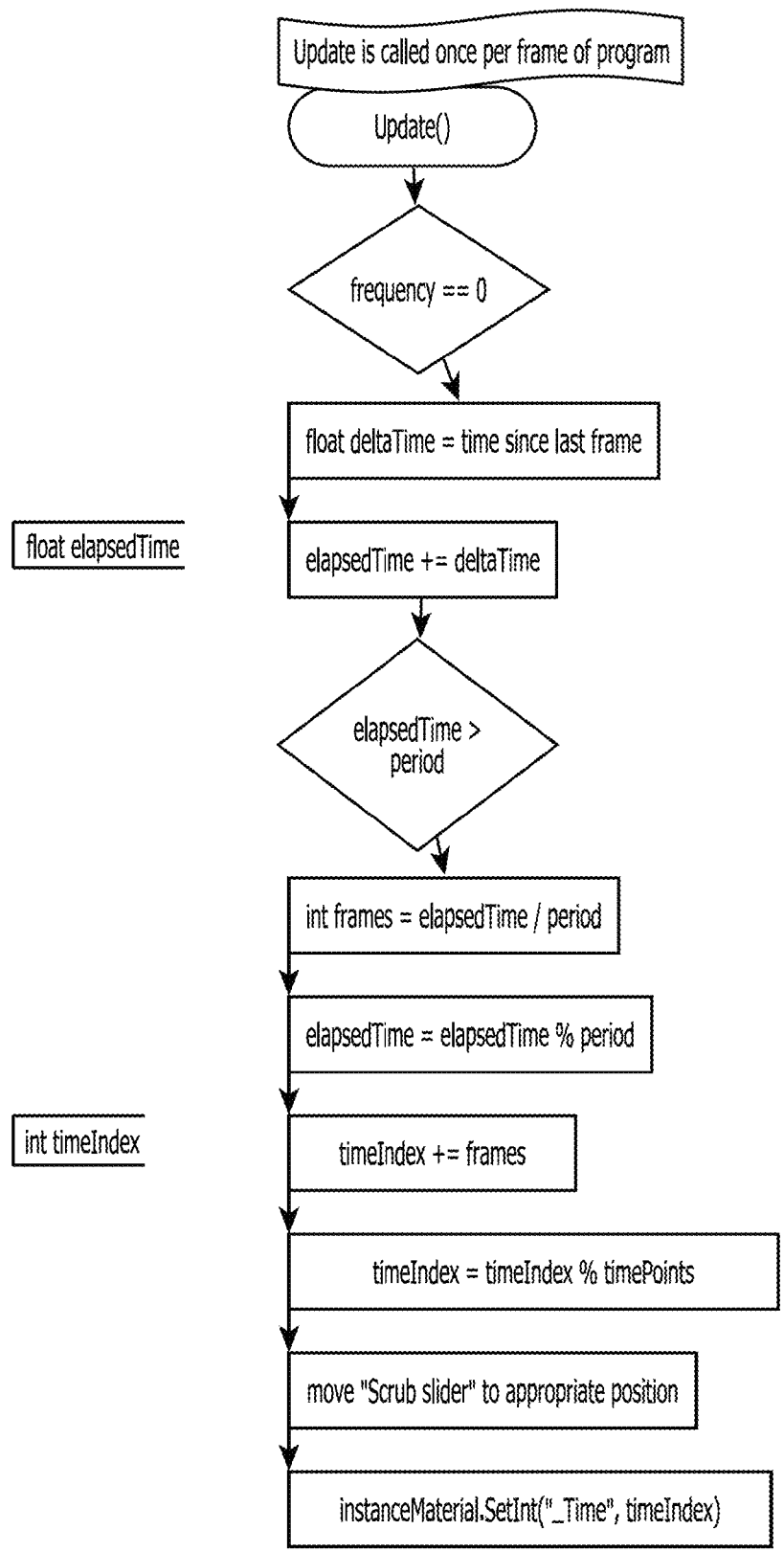
FIG. 49 is a flowchart describing an example method of implementing frame wise updates on a rendering of an object based on a MEG data set, using an IMVR system, according to an embodiment.
Figure 50:
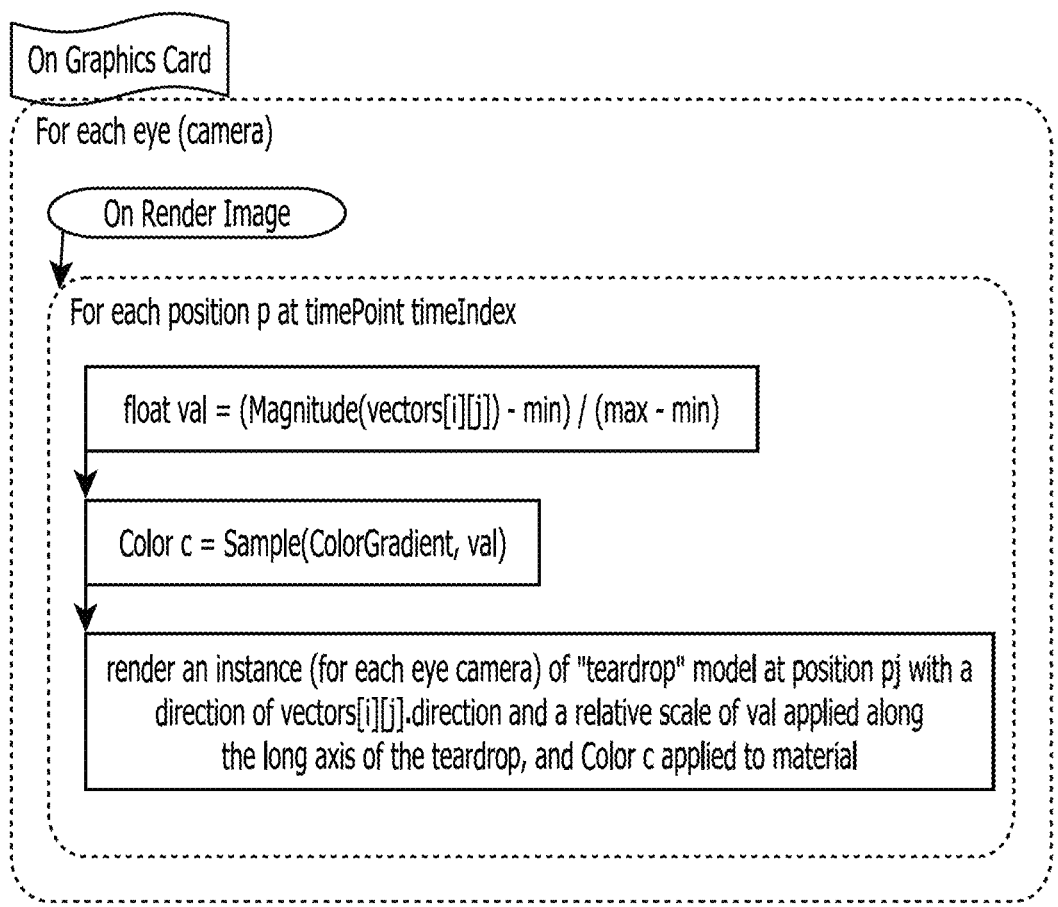
FIG. 50 is flowchart describing an example method of implementing a rendering of an object based on MEG data, using an IMVR system, according to an embodiment.

The example visualization 4601 is a frame at a single time point in a representation over time of vector data obtained from MEG imaging over several time points, of a subject's brain while listening to a predetermined sound. The representation illustrates neural activity increase in the area associated with the auditory cortex in the temporal lobe of the subjects brain. The changing neural activity over time points is represented by changes in the properties like color, length, and orientation of the instances of the model object over time points. FIG. 49 is a flowchart describing an example method of updating user inputs associated with a rendering of MEG data at a user device. FIG. 50 is a flowchart describing an example method of implementing a rendering of an example MEG data set. A representation of the MEG data as described above can help clinicians easily identify changing trends of neural activity. For example, a visualization of MEG data over time, as described above, can be used to easily and quickly identify a locus of seizure activity or a locus of desired activity in response to a predefined stimulus that can aid in surgery.

Other data sets may include EEG, geological data, molecular data, or any other point cloud data with or without a time component. In some implementations, data can be collected through a network socket and displayed to a user in substantially real time.

As described herein, a renderer of an IMVR system can obtain a data set associated with a three dimensional object, in some instances the data set including serial two dimensional images of the object taken using an imaging technique, and render the object in an IMVR environment such that multiple users can visualize and manipulate the object concurrently. The rendering of the object in an IMVR environment can be done using any suitable set of predetermined properties that can determine the level of visualization and/or manipulation that may be available to the users. Some of the predetermined properties associated with the rendering of the object can be set using inputs from a user (e.g., a host user or a first user defined to have increased control over an IMVR session, an IMVR session being a discreet IMVR experience including one or more users). In some implementations, the properties can be defined to be set by any participating user. FIG. 12 illustrates a list of user inputs. For example, the IMVR system can receive inputs associated with "nearClip" that set the users' ability to clip near portions of a rendered object from visualization, using a predefined near clipping plane.

Input "alphaThreshold" can be used to set a transparency threshold property of visualization of an object or a portion of an object. Inputs associated with samples can be used to set the number of samples to be used to render an object with reference to a user device (that is used by a user to visualize the rendering). Some inputs can determine the quality of rendering and the efficiency of rendering. For example, "skip" and/or "MIP mapping" when enabled can command the IMVR system to render objects in consideration of null spaces that do not include the object. Skipping portions of null spaces when detected, and only returning to sample regions based on identifying not null spaces can increase efficiency of rendering while maintaining quality of visualization. Additional inputs from user(s) can be set to determine a skip rate (based on processor speed and function of a user device, and the nature of the data set visualized). Binning and/or foveated rendering can also be employed to further increase efficiency of rendering.

As additional examples, inputs associated with cross-section tool can enable cross-sectioning functionality in an IMVR environment, inputs associated with setting parameters associated with inclusion and exclusion objects during rendering can enable isolated rendering of objects by including and/or excluding other surrounding objects. Inclusion and exclusion based definitions can be with respect to other objects in the immediate neighborhood of the object of interest in the IMVR environment. As additional example, inputs associated with a set of annotation tools (e.g. a paint tool, Voxel painter, measurement tool, annotation tool, etc.) can be used to enable ability of a user to annotate, or manipulate rendered objects using a paint tool (e.g., paint or change appearance properties by for example adding color or reducing transparency). Some examples of such inputs can include measurement inputs, annotation inputs, paint inputs, highlight inputs, mark-up inputs, etc.

FIG. 13 is a flowchart 1300 of an example method of generating an IMVR environment and recording media associated with the IMVR environment by a renderer (e.g. IMVR renderer 305 or the user specific VR renderer 216 of user device 201) in an IMVR system, according to an embodiment. At 1371 the method 1300 includes receiving data including medical images associated with an object. As described previously, the medical images can include DICOM images such as images obtained via computed tomography (CT), magnetic resonance imaging (MRI), Positron emission tomography-computed tomography (PET-CT), and/or initiation of Magnetoencephalography (MEG) data, as well as one or more other data sources that include serial optical sectioning and imaging of three dimensional objects such as confocal microscopy, electron microscopy, any light microscopy with data acquisition over multiple planes.

Figure 24:
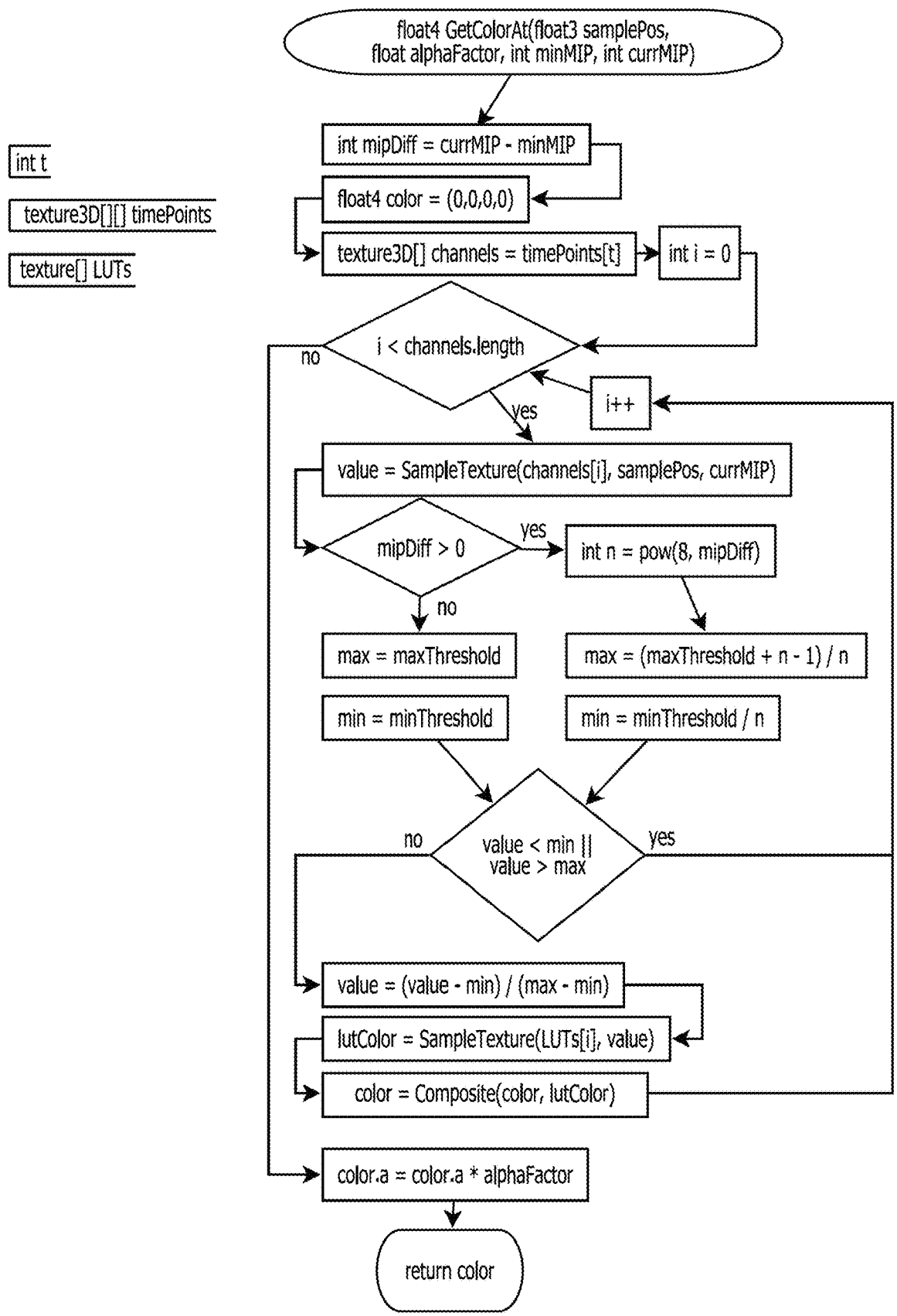
FIG. 24 is a flowchart describing an example method of rendering a colorized view of objects in an IMVR environment by an IMVR system, according to an embodiment.
Figure 25:
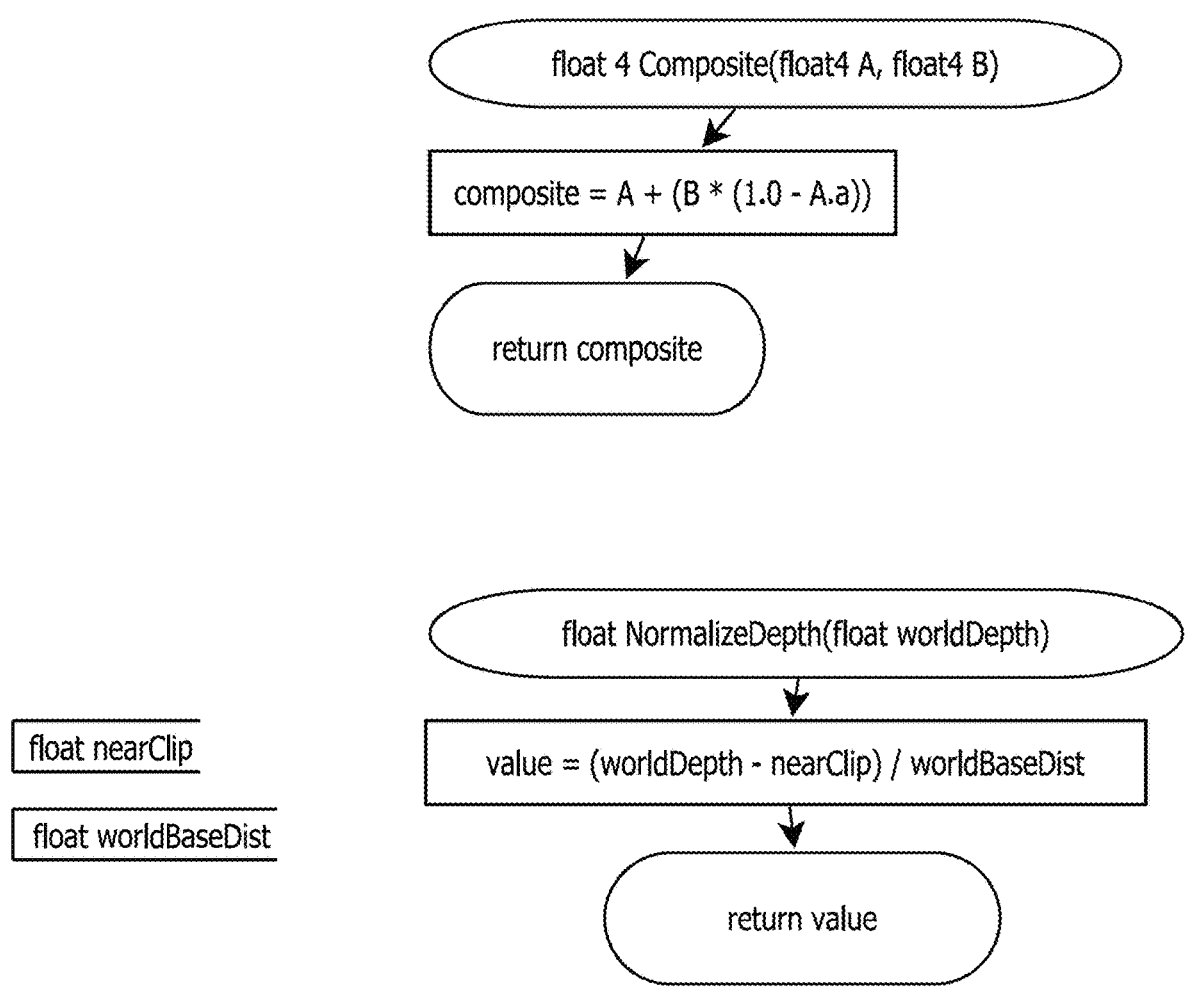
FIG. 25 is a flowchart describing an example method of generating a composite view of objects in an IMVR environment, obtained from two or more sources, by an IMVR system, according to an embodiment.

At 1372, the renderer extracts, from the data, a data set associated with a structure of the object and user information associated with a spatial position of a user with reference to the object in a virtual environment (also referred to herein as an "IMVR environment"). The data can include additional information associated with the data set that can be also extracted and used to set one or more parameters of the IMVR environment. For example the data can include a sample number associated with the object, a channel specification including a number of channels of data, and look-up-tables (LUTs) associated with each channel of data. The data set can include one or more channels of information associated with volume data associated with the object. Each channel can be defined such that the object can be rendered using one or more channels that can be optionally visualized separately by a user. For example, each channel can be rendered using a look-up-table (LUT), each LUT being separable from other look-up-tables (e.g., spectrally separable), such that the LUTs can be individually manipulated to change the visualization of the rendered object in that channel of data. Channels can be configured such that rendered objects using each channel can be composited to form a composite object. FIGS. 24 and 25 are flowcharts describing example methods to generate a composited instance of a rendered object using multiple channels of data, in an IMVR system according to an embodiment. For example, as shown in FIG. 24, a renderer can implement procedures involving Maximum Intensity Projection (MIP) to render an object in an IMVR environment. The renderer can get information associated with position, color and MIP values. The renderer can compute a MIP difference value indicating a difference between a MIP values of a sample of a channel of data at a position and compare the value to a threshold set by a user. Based on the comparison the renderer can generate a LUT including a composite of color and transparency information. FIG. 25 also illustrates an example method of returning a composite color given a pair of colors. FIG. 25B is a flowchart of an example method to normalize depth visualization, using information related to a nearclip setting and a world depth setting (e.g. by a user) in a rendering of an object in an IMVR environment.

In some implementations, the data can include instructions and a set of keys, but not the LUTs for a channel, and the LUT can be locally generated using the keys. Each key can include properties associated with color, transparency such that combinations of keys can be used to generate the LUTs. The user information can include a relative spatial location, and a relative orientation of the user with respect to a rendered object. In some implementations, one or more user devices in an IMVR system can include headsets, head mounted display, and/or one or more manipulating controllers. The renderer can receive a head position and/or a hand position and a pose or pointing direction within the IMVR environment from the head set and the hand controller and use that information to render the object.

Referring back to FIG. 13, at 1373 the renderer receives a set of inputs from the user, the set of inputs being associated with a set of predetermined properties associated with a portion of the object in the IMVR environment. The set of inputs can include inputs defined above with reference to FIG. 12. The properties can include a set of visualization properties. In some implementations the user inputs can include changes applied to the LUTs to render the object.

At 1374, the renderer renders, based on the set of inputs and the user information, an instance of the portion of the object in the virtual environment. At 1375, the renderer receives manipulation information related to a manipulation of the rendered instance of the portion of the object by the user and in the virtual environment. In some implementations the manipulation information can be received through a set of inputs received from the user via a headset or one or more hand controllers. Manipulations can include user actions configured to induce effects on the IMVR environment that manifest as changes to the visualization of the rendered object. For example, manipulations can be configured to change appearance properties of one or more portions of the rendered object. For example, changes to color or transparency of one or more portions of a rendered object, orientation, scale, or view of a rendered object. Manipulation can also be configured to induce a change in the relative position and/or orientation of the user with respect to the rendered object.

At 1376, the renderer renders, based on the manipulation information, an updated instance of the portion of the object that manifests an effect of the manipulation in the virtual environment.

At 1377, the user device records media associated with the manipulation and the rendering of the updated instance of the portion of the object, the media including a video of the rendering of the updated instance of the portion of the object, from a perspective of the user within the IMVR environment, and the perspective being based on the spatial position of the user within the IMVR environment. In some implementations, a recording of an IMVR session or an IMVR experience can be configured to capture position, host information, timestamp and audio. In some implementations, the media can include an audio recording of the sounds associated with the rendering of the object, including sounds generated by one or more users in an IMVR session. In some instances the recorded audio can be associated with the recorded spatial location within the IMVR environment such that a playback of the media can enable a second user experiencing the video to also experience the audio in consideration of location of the source of sounds within the IMVR environment. For example, audio from a source at a spatial location forward and to the right of a user's position can be configured to manifest as audio louder at the front and right side of the user. As another example, recording and/or playback can include dynamic location of source of the audio. In other words, audio generated by a user moving through the virtual space and/or interacting with objects in the virtual space can be recorded such that the movement and/or changes in the visualization of both the user and the object interacted with is captured in both video and audio with suitable time stamps, and can be recreated at playback to be experienced by another user. In some implementations, the second user implementing the playback can chose between just plain audio playback and an audio including spatial information such that audio is dynamically adjusting to the second user's location as well the dynamic nature of the source.

In some implementations, playback can be initiated by more than one user and the audio including spatial information can be presented to each user according to the user's spatial location, in the multiuser session. In some implementations, a host user may automatically record video and/or audio associated with an IMVR session. In some instances the recorded audio may be associated with the host user. In some implementations, each user in a multiuser IMVR session can be associated with audio and audio recording can be managed to obtain one audio per user in that IMVR session. In some implementations, the IMVR system can sense that a particular user is generating sounds (e.g., talking) and the IMVR system can silence that user's audio to generate better quality of sound production and relay to the other users in that session (e.g., to avoid echo effects, or interference effects). In some implementations, the IMVR system can manipulate the set of audio associated with the users including starting and stopping to capture interaction between users (e.g., discussion between tutors and students in a virtual classroom session). In some instances, subsets of an IMVR session can be recorded (e.g., a subgroup of students in a larger classroom). In some implementations, one instance of a IMVR environment from one session (e.g., a subgroup of students in a virtual class) can be exported to another IMVR environment associated with another session (e.g., another subgroup of students, or a class of students).

A user device in an IMVR system can be configured to support playback by a second user with a set of control functions. The second user can select a set of properties of playback and/or select values associated with the properties at the user device. For example the playback can be started, paused and/or stopped at user discretion. The playback can be rewound, replayed or modified in other suitable ways. In some implementations, a second user can select at the user device properties like transparency, color to modify and/or manipulate the instance of portions of the object rendered in the playback.

As described herein, an IMVR system can be configured to support multiple users interacting with an object in the IMVR environment. The IMVR system can be configured such that the shared IMVR environment is unified in presentation across the multiple user devices, irrespective of the method by which each user device may be connected (e.g., via wired connection, wireless connected, via communication networks of varying parameters, etc.), regardless of the specific hardware configuration of each of the user devices. In some instances, the IMVR system can be configured to perform a weighted rendering in consideration of a hardware configuration of a user device such that the appearance of the instance of the rendered object at that user device is similar to or matches with the appearance of the instances on other devices. For example, if a user device is more powerful and capable of higher sampling rates or frame refresh rates than other user devices in a shared IMVR session, the renderer associated with that user device can calibrate rendering properties like color and/or transparency associated with a portion of the object to accommodate the difference in hardware configuration. As an example a user device capable of 500× samples can uses sample values weighted to a smaller fraction (e.g., 1/500× value) compared to a user device capable of 300× the samples (which might use a sample weighting of 1/300).

Figure 36A:
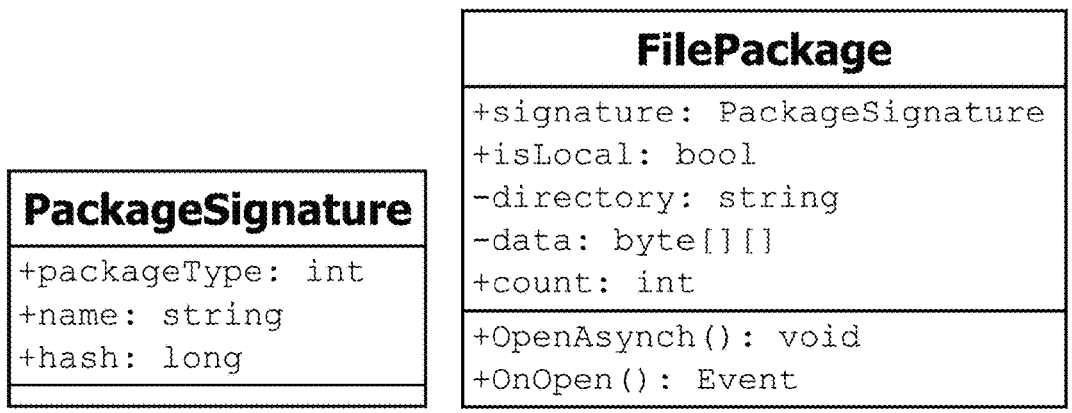
FIG. 36A is a schematic representation of an example data package that can be transferred to a device to enable a user associated with the device to join in an IMVR environment using an IMVR system, according to an embodiment.

New user devices can be added to an on-going IMVR session to join the session seamlessly and experience the unified presentation of the IMVR. In some implementations, if the new user device does not already have the data package associated with the ongoing IMVR session, the new user device can receive a data package. In some instances, the new user device can receive all the data in a library of data packages. In some instances the new user can receive the data associated with the portion of the IMVR session in progress (e.g., medical data associated with one patient, or medical data associated with instruction for one class) and not a full complete library. FIG. 36A is a schematic representation of an example data package.

Figure 26:
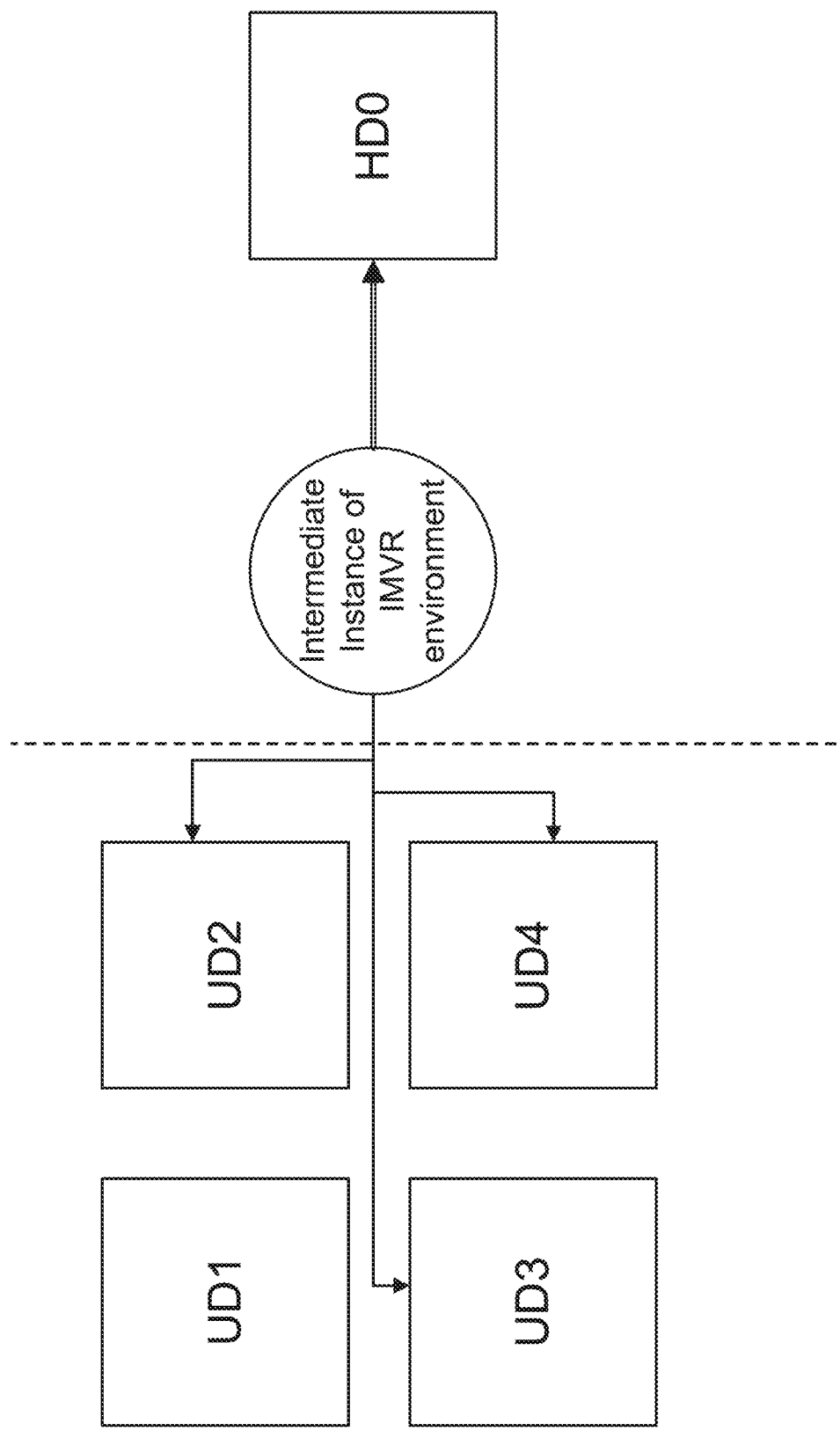
FIG. 26 is a schematic representation of an IMVR system configured to manage multiple instances of an object rendered in an IMVR environment such that an instructor may flexibly join or leave a set of shared IMVR sessions between students implementing the IMVR system, according to an embodiment.

In some implementations, for example, the data package can be raw imaging data sent to a user device's graphics card. In some implementations, a palette of images can be selected by a sending user and the selected data set can be sent to the new user device. As described above, an IMVR session can include several users and, in some implementations, the IMVR system can institute a hierarchy of users with increasing or decreasing privileges. For example, FIG. 26 illustrates an example set-up where an IMVR session can be initiated by a first user or a host user associated with host device HD0 and with maximum privileges. The host user can invite other users with user devices UD 1-4 and provide the data package to the user devices, over a network (e.g. TCP/IP connection network) to join the IMVR session. FIG. 26 illustrates an example set-up with a host user associated with a host device HD0 and a set of user devices UD1-4.

Figure 36B:
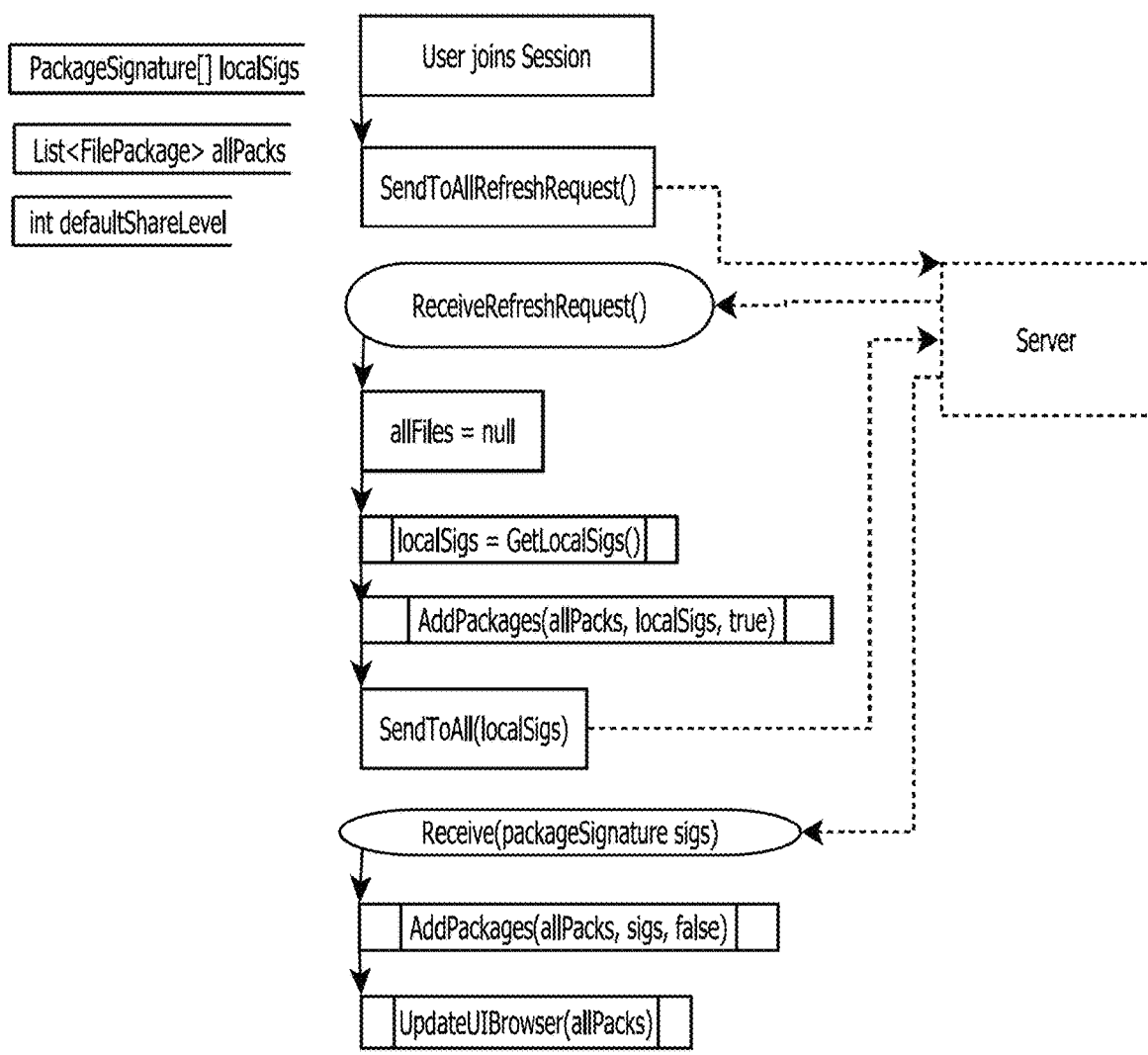
FIG. 36B is a flowchart illustrating a sequence of events involved in a user joining an ongoing IMVR session, according to an embodiment.

The IMVR system can be configured such that the new user device can be programmatically instructed to check for completeness of the received data package, and to synchronize the data package with respect to the other users. FIG. 36B is a flowchart describing an example method of data package handling to permit a user to join an IMVR session. In some instances, the data package can be stored in a non-volatile memory (e.g., memory associated with a Central Processing Unit (CPU)) locally in the receiving user device in addition to being stored in a volatile memory (e.g., a memory associated with a Graphics Processor Unit (GPU), VRAM, etc.). In some implementations, the sending user or the host user can authorize the receiving user to allow local storage in a non-volatile memory in the receiving device. In some implementations, a data package can be associated with permission information indicating the authorization available for handling, using, and/or storing the data set included in the data package.

In some implementations, the data may be bound by privacy protection and thus the receiving user device can be instructed by the sending user device or the host user device to not save the data in a non-volatile memory associated with the receiving user device but to only save the data to a volatile memory associated with the receiving user device (e.g. Graphics processing card). In such implementations, the data can be configured to be removed from any other volatile memory associated with the device (e.g. RAM) after saving the data to the video ram used by the renderer. In some instances, the IMVR system can be configured to transmit the data package in chunks, one chunk at a time, such that the receiving device does not have access to more than one chunk of data at a time.

Figure 27:
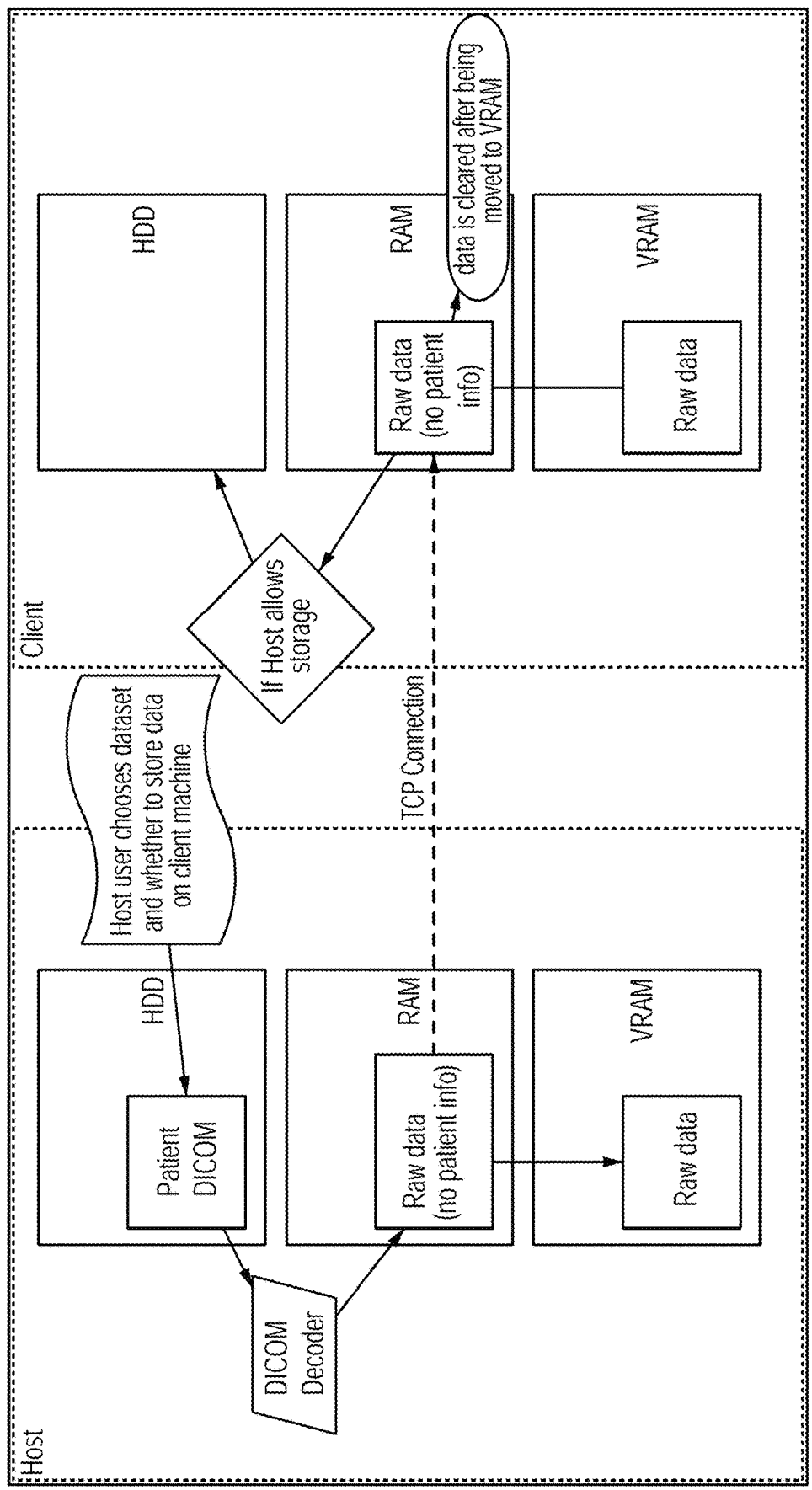
FIG. 27 is a schematic representation of a method of sharing data related to an IMVR environment between a host machine and a client machine, using an IMVR system, according to an embodiment.

In some instances, the data package can be modified before sending to the new user. For example, the data package can be scrubbed to remove patient identifying metadata and then sent to the receiving user device. The receiving user device can be instructed to extract the information used to render the object and join the IMVR session in progress with the other users. For example, the receiving data can extract data associated with the rendering (voxel data, voxel size, voxel width, voxel height, etc). FIG. 27 is a schematic representation of a method of sharing data related to an IMVR environment between a host machine and a client machine, using an IMVR system, according to an embodiment. In some implementations, the host machine can be a user device associated with a first user or a host user (e.g., user device 101 of FIG. 1A) and the client machine can be a user device associated with a subsequent user (e.g. user device 102). In some implementations the host machine can be an IMVR renderer (e.g. IMVR Renderer 105) and the client machine can be a user device (e.g. user device 102).

In some implementations of the user device portion of an IMVR system described herein, the system may be configured to indicate to a set of user devices in an ongoing IMVR session the upcoming addition of a new user to the session. In some implementations, the IMVR system can indicate the readiness of the new user with a level of completion of rendering with respect to the new user's device, as shown in an example method described by the flowchart in FIG. 37. Audio (e.g., voice) and position data of new users within the IMVR environment can be broadcasted to other user devices before the new user joins live and is permitted to manipulate the IMVR environment. The user interface associated with a user device in an IMVR system may provide a visual indicator to the other users that a new user is visualizing the same object as the host user while the new user joins the session. The host user (e.g. a first user in a shared IMVR session) can set limits on the controls of a new user while data packages associated with the user device of the new user are being loaded or while an instance of the object is being rendered at the user device of the new user. For example, the new user can have restricted access to manipulations on the IMVR environment while a first instance of one or more objects in the IMVR environment is being rendered at the user device of the new user.

In some implementations, a host user can have control over an intermediate instance of the IMVR environment shared by a set of users. FIG. 26 (described above) is a schematic representation of an IMVR system configured to manage multiple instances of an object rendered in an IMVR environment such that an instructor may flexibly join and leave a set of shared IMVR sessions between students implementing the IMVR system, according to an embodiment.

Figure 37:
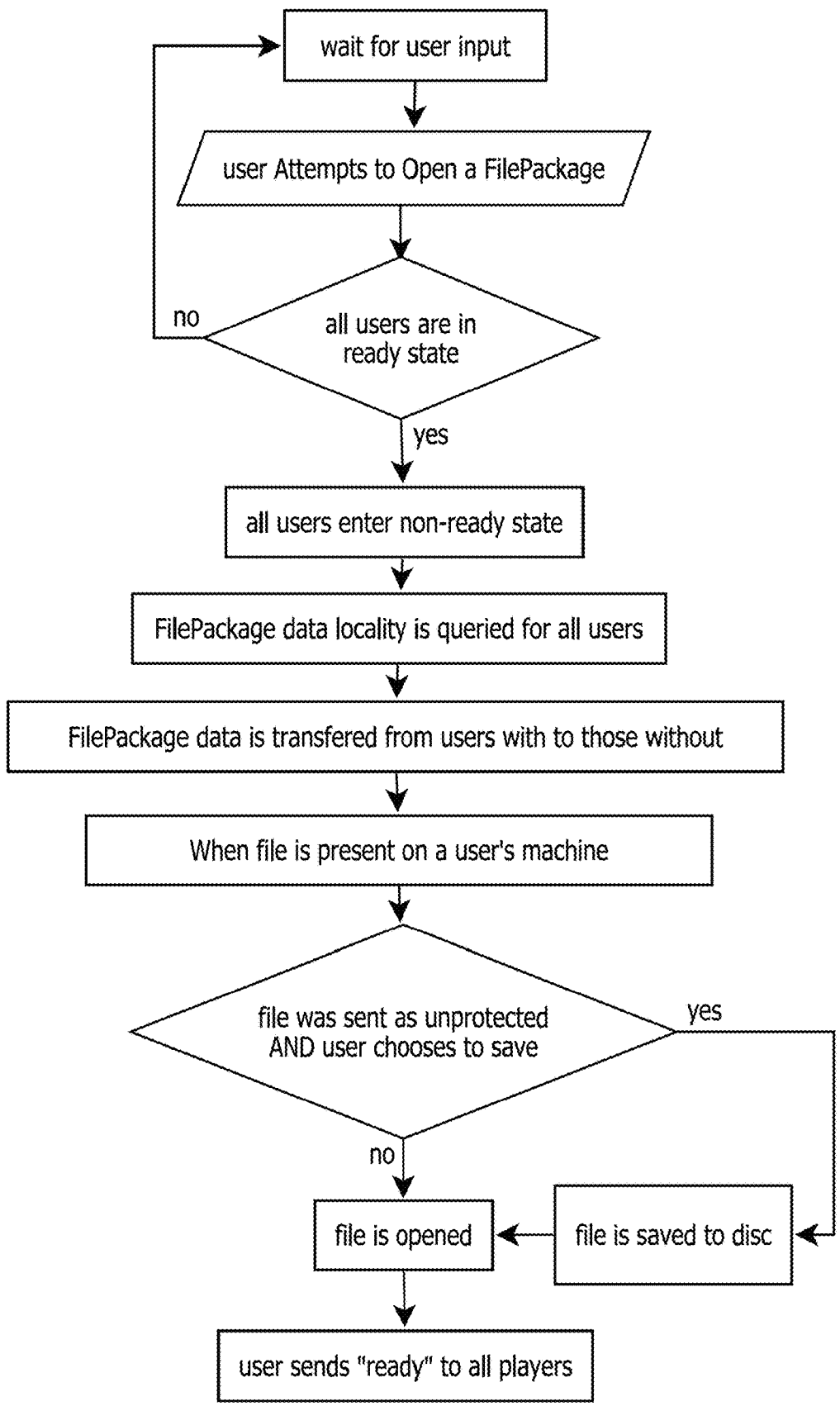
FIG. 37 is a flowchart describing an example implementation of a method to indicate a ready state of users when transferring data packages between users in an IMVR session using an IMVR system, according to an embodiment.
Figure 38:
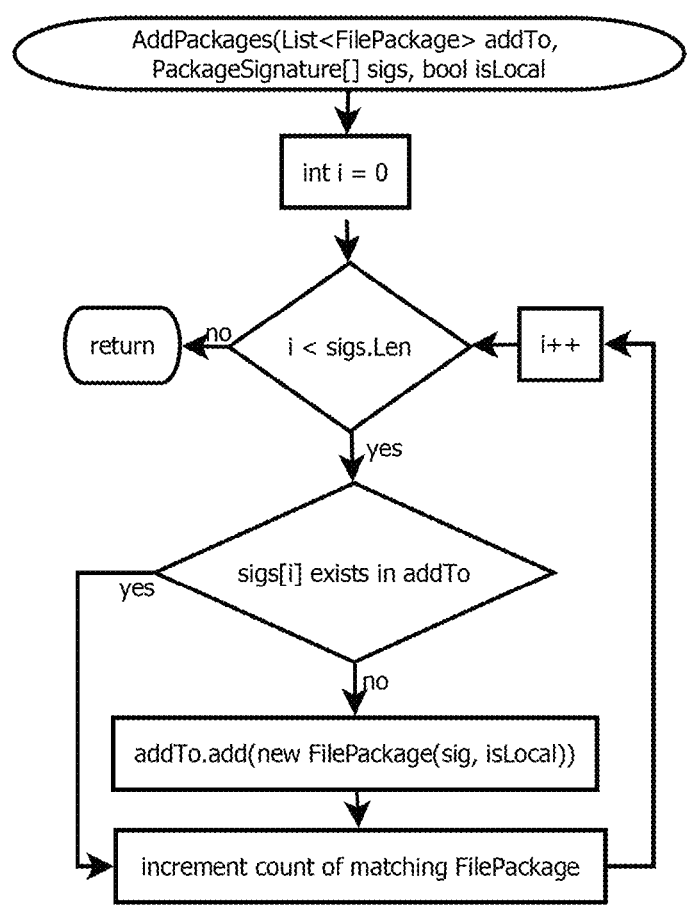
FIG. 38 is a flowchart describing an example method of managing data packages and merging information related to a new user with an ongoing session of an IMVR experience when a user is allowed to join the ongoing IMVR session using an IMVR system, according to an embodiment.
Figure 39:
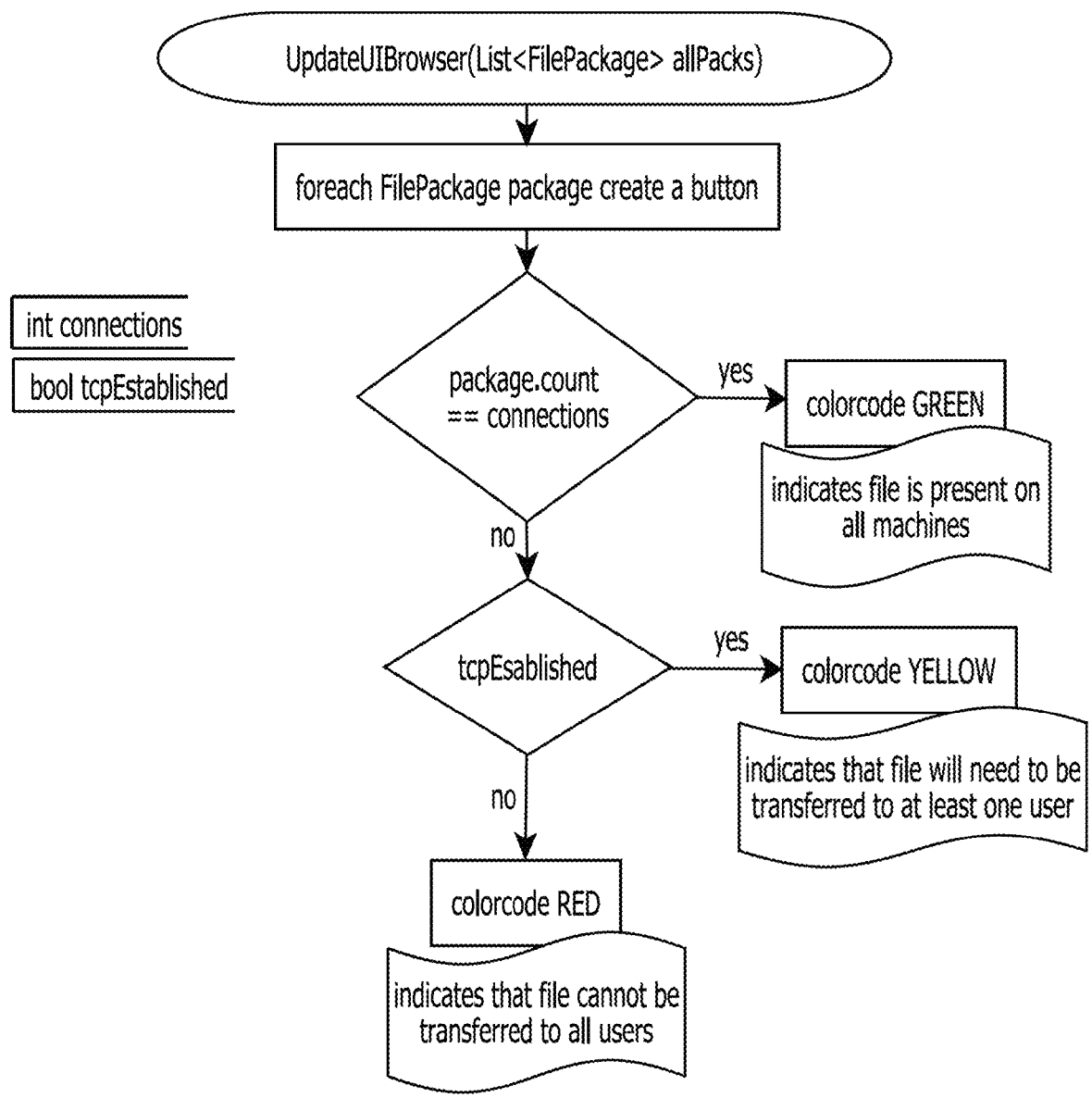
FIG. 39 a flowchart describing an example method of managing user interfaces associated with an IMVR session involving multiple concurrent users using an IMVR system, according to an embodiment.

FIG. 37 is a flowchart describing an example implementation of a method to allow a user to join an ongoing IMVR session, as described above, using an IMVR system according to an embodiment. FIG. 38 is a flowchart describing an example implementation of a method to add a data package to an existing library of data packages associated with a user device, the user device being associated with a new user joining an ongoing IMVR session. The flowchart in FIG. 38 can be used by a renderer (e.g., Renderer 305) or a user device (e.g., user device 201) to update the data packages associated with the new user and to synchronize the data packages associated with rendering an object, across all user devices in the ongoing IMVR session using an IMVR system according to an embodiment. FIG. 39 is a flowchart describing an example method of managing user interfaces, including providing visual indications of a new user to an existing set of users associated with an IMVR session, using an IMVR system according to an embodiment. The method described in FIG. 39 can be implemented by a renderer (e.g., renderer 305) or a user device (e.g., user device 201) described herein.

Figure 40:
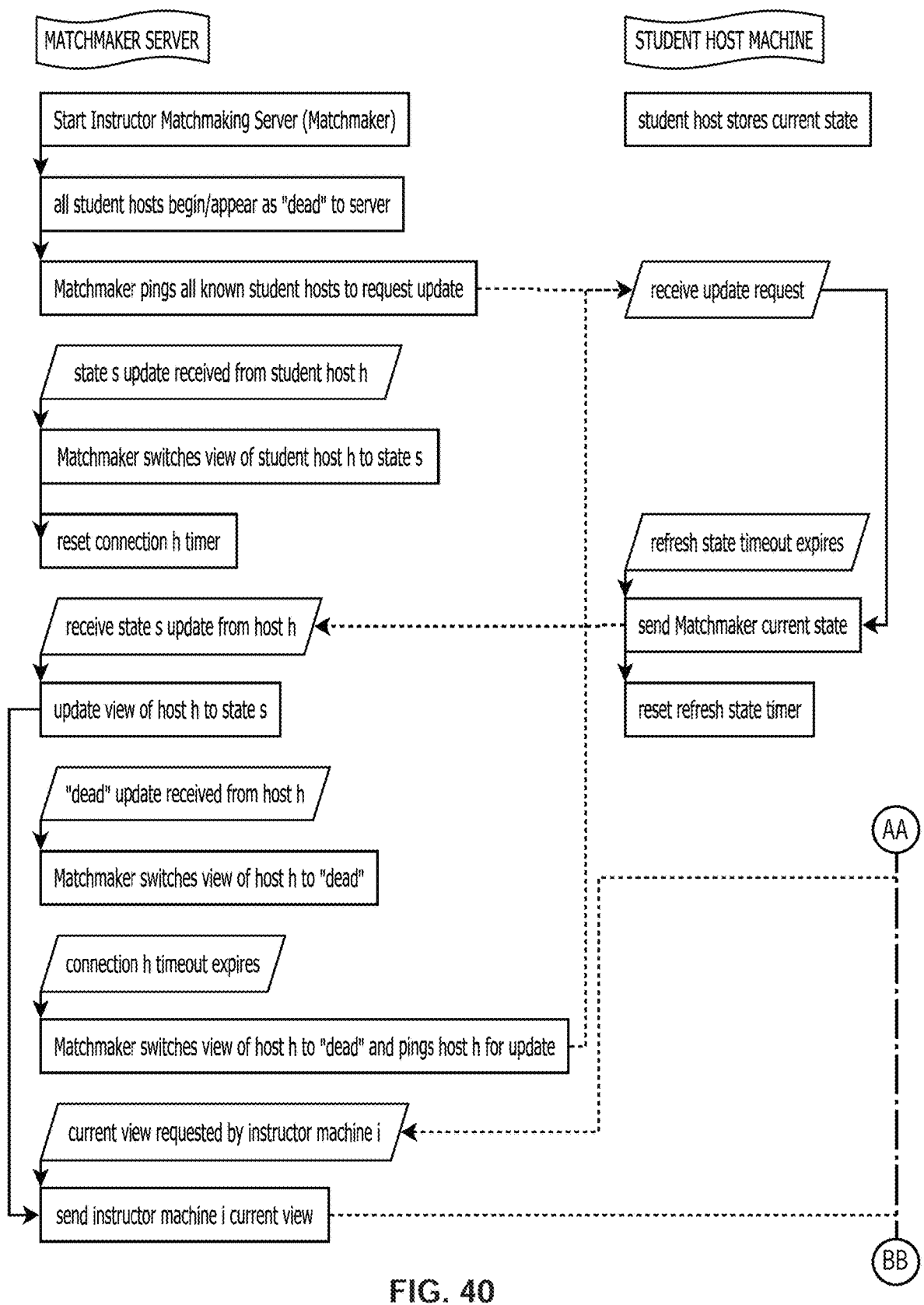
FIG. 40 a flowchart describing an example implementation of a method to allow a user to join one of any number of in-progress IMVR sessions, according to an embodiment.
Figure 40:
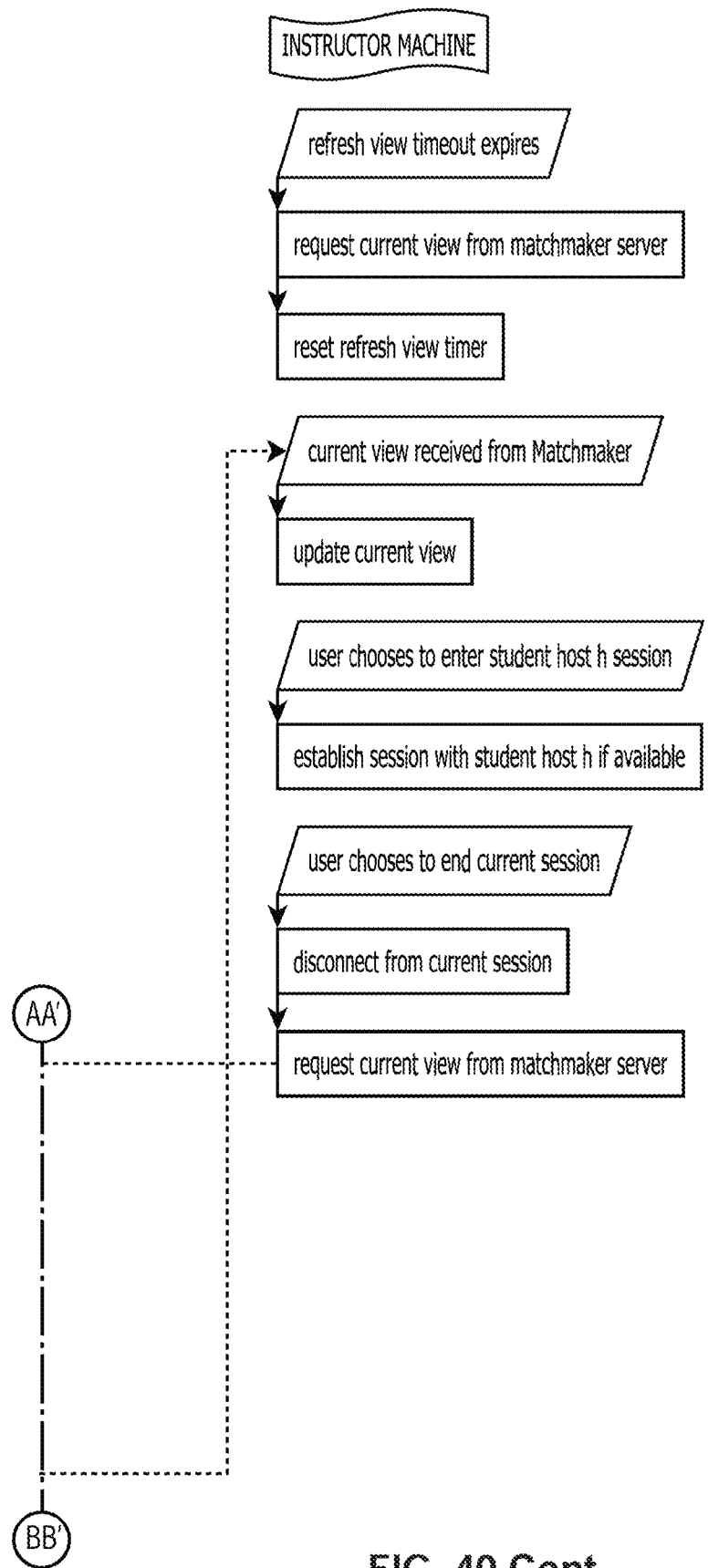

FIG. 40 is a flowchart describing an example method to match students with instructors, using a matchmaker server. For example, the matchmaker server can take into consideration the current states of student devices and instructor devices and match students with instructors in an IMVR session. In some implementations, the instructor devices can be similar to user devices (e.g. user device 201) described herein. The student devices can also be user devices (e.g. user device 201). In some implementations the student devices can be user devices defined to have restricted functionality. For example, one or more student devices can have restrictions related to access to or ability to accept data packages, ability to authorize transfer of data packages, ability to annotate or modify data packages, ability to perform certain manipulations of the data or of the instance of an object rendered in their user devices, ability to invoke, start or leave shared IMVR sessions, ability to record or playback recordings of an IMVR experience, etc.

In some implementations, an IMVR system can be configured to allow several IMVR sessions to operate in parallel using data packages that may be related. The several IMVR sessions can be organized and managed by the IMVR system to have one supervisory session with a supervisory user and several sub-sessions with smaller groups of users (e.g., a class with an instructor and a sub-session including smaller sub-groups of students working in groups). Users can be provided with tools to be able to flag for assistance or flag for the attention of a set of the other users within their IMVR session or between their IMVR session and another parallelly occurring IMVR session (e.g., parallel virtual rooms) and send and receive messages across other sessions to other users. For example, students in one sub-session can request assistance from the instructor who may be within another session. In some instances, the IMVR system can configure a hierarchy of IMVR sessions set-up such that a higher order session can be accessible to user in a lower order sub-session. The sub-sessions can be configured to use the same data package as the higher order session. In other instances the sub-sessions can be configured to use copies of the data package associated with the higher order session, each copy allocated to each of the sub-sessions. In some implementations, the IMVR system can be configured to project or export instances of the rendered object and/or the manipulations in a sub-session up or down a hierarchy to a higher session (e.g., from a sub-group to the whole class) or a lower session (e.g., from the sub-group to an even smaller group).

Figure 14:
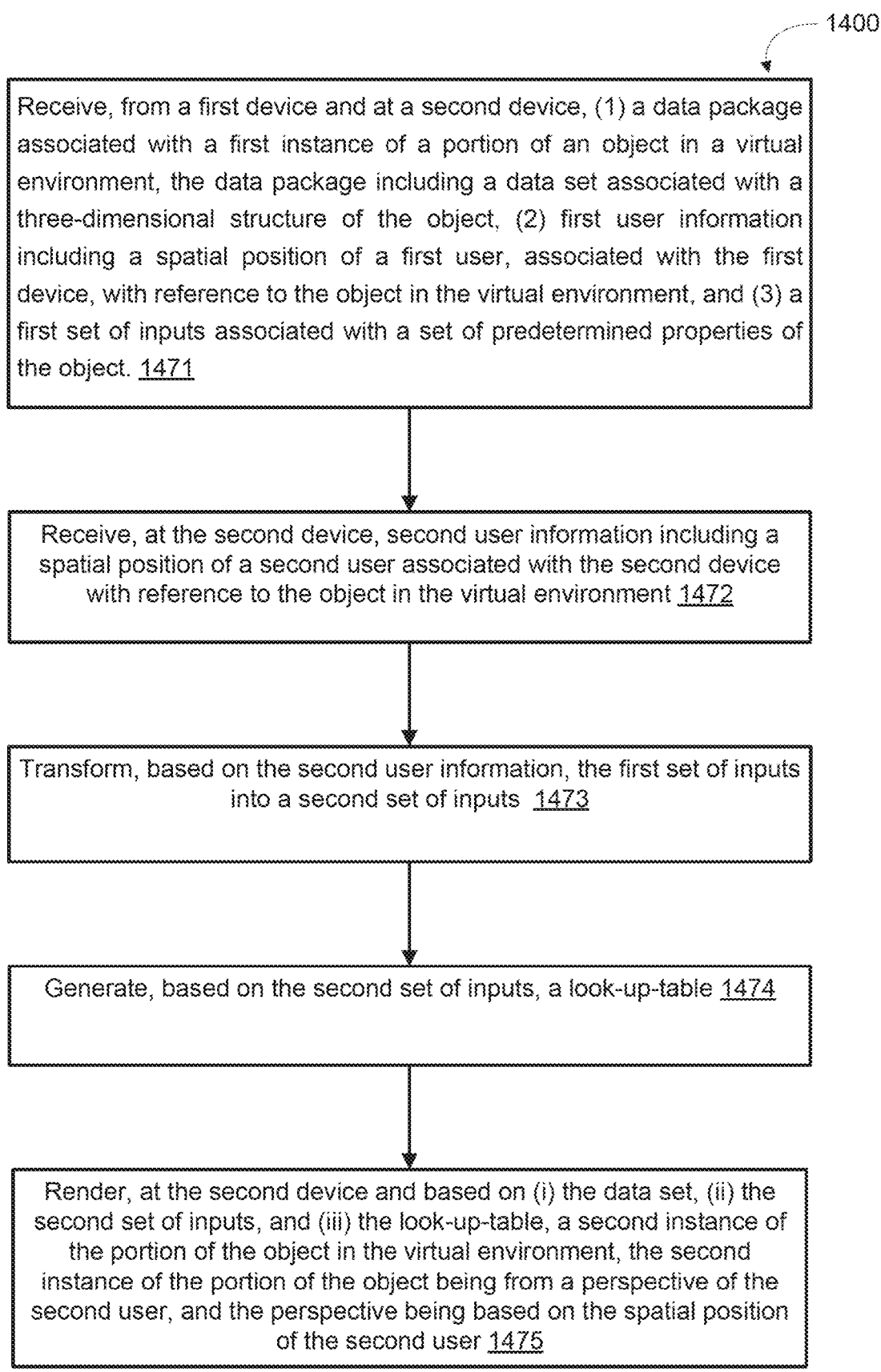
FIG. 14 is a flowchart describing an example method of receiving data associated with a first instance of an object in an IMVR environment and using the data to render a second instance of the object such that the first user can share the IMVR environment with the second user.

FIG. 14 is a flowchart describing an example method 1400 of receiving data associated with a first instance of an object in an IMVR environment and using the data to render a second instance of the object such that the first user can share the IMVR environment with the second user.

At 1471, a renderer receives, from a first device and at a second device, (1) a data package associated with a first instance of a portion of an object in a virtual environment, the data package including a data set associated with a three-dimensional structure of the object, (2) first user information including a spatial position within the virtual environment of a first user associated with the first device, with reference to the object in the virtual environment, and (3) a first set of inputs associated with a set of predetermined properties of the object.

At 1472, the renderer receives, at the second device, second user information including a spatial position of a second user associated with the second device with reference to the object in the virtual environment.

At 1473, the renderer transforms, based on the second user information, the first set of inputs into a second set of inputs. At 1474, the system generates, based on the second set of inputs, a look-up-table.

At 1475, the renderer renders, at the second device and based on (i) the data set, (ii) the second set of inputs, and (iii) the look-up-table, a second instance of the portion of the object in the virtual environment, the second instance of the portion of the object being from a perspective of the second user, and the perspective being based on the spatial position of the second user.

Figure 15:
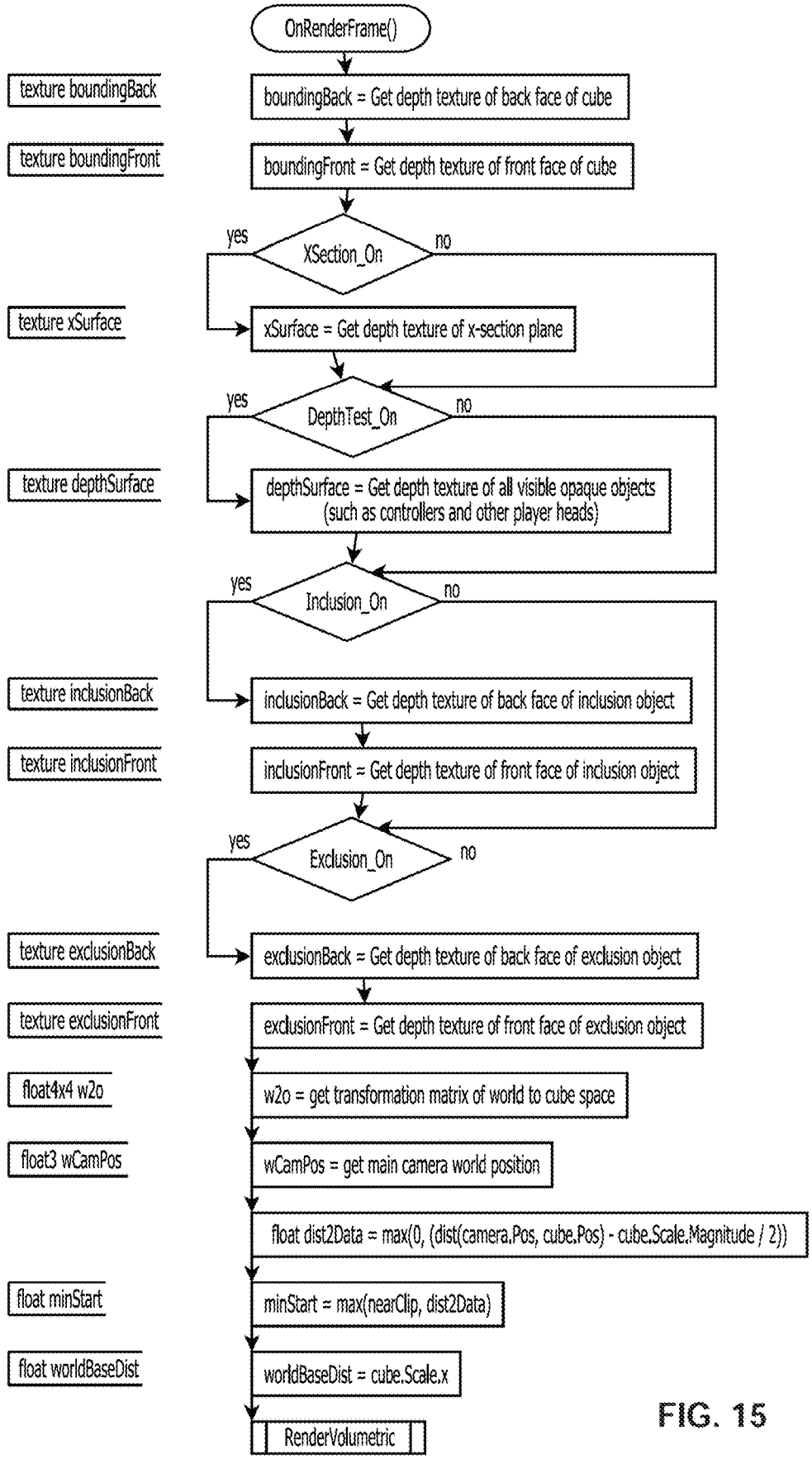
FIG. 15 is a flowchart describing an example method of rendering a volume object in an IMVR environment, by an IMVR system, according to an embodiment.

FIG. 15 is a flowchart describing an example method of rendering a volume of an object in an IMVR environment, by a renderer of an IMVR system (e.g. renderer 305), according to an embodiment. For example, a renderer can receive information related to depth texture of a back face of a cube and a depth texture of a front face of a cube. The renderer can check if a cross-section functionality of the renderer is selected. (e.g., XSection_On=1 can indicate a selection). If selected, the renderer can get depth texture of a cross-sectioning plane. If not selected, the renderer can check if a DepthTesting functionality is selected. If selected the renderer can get depth texture of all visible opaque objects. The renderer can check for selection of inclusion and exclusion property values and based on the selection get depth texture of the back and front face of an inclusion object or the back and front face of an exclusion object respectively. The renderer can get a transformation matrix to transform the real world space to cube space, get main camera position associated with a user device, scaled the world environment based on the cube scale, among other steps, and render the volumetric data.

Figure 16:
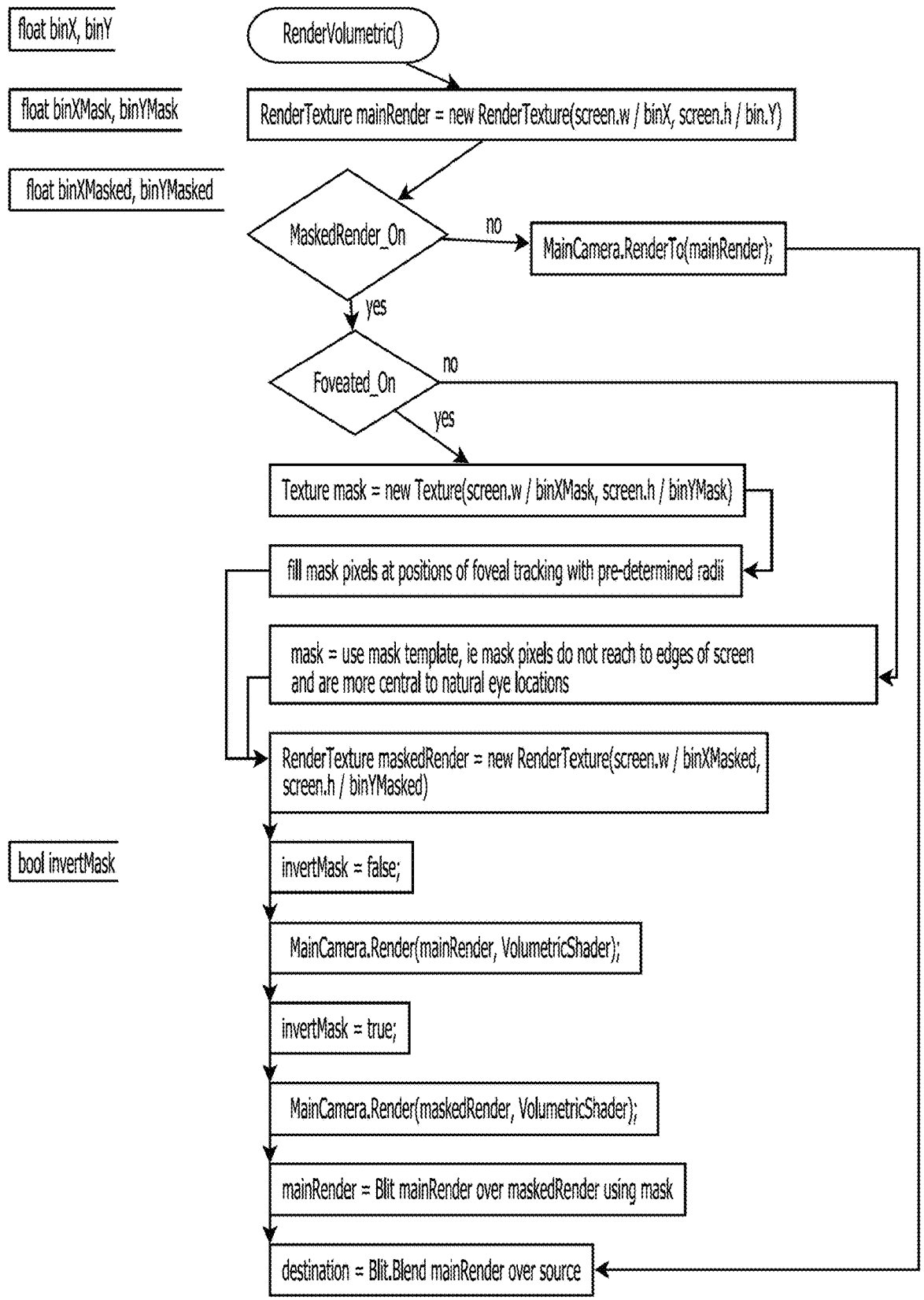
FIG. 16 is a flowchart describing an example method of rendering a volume object in an IMVR environment, according to an embodiment.
Figure 17A:
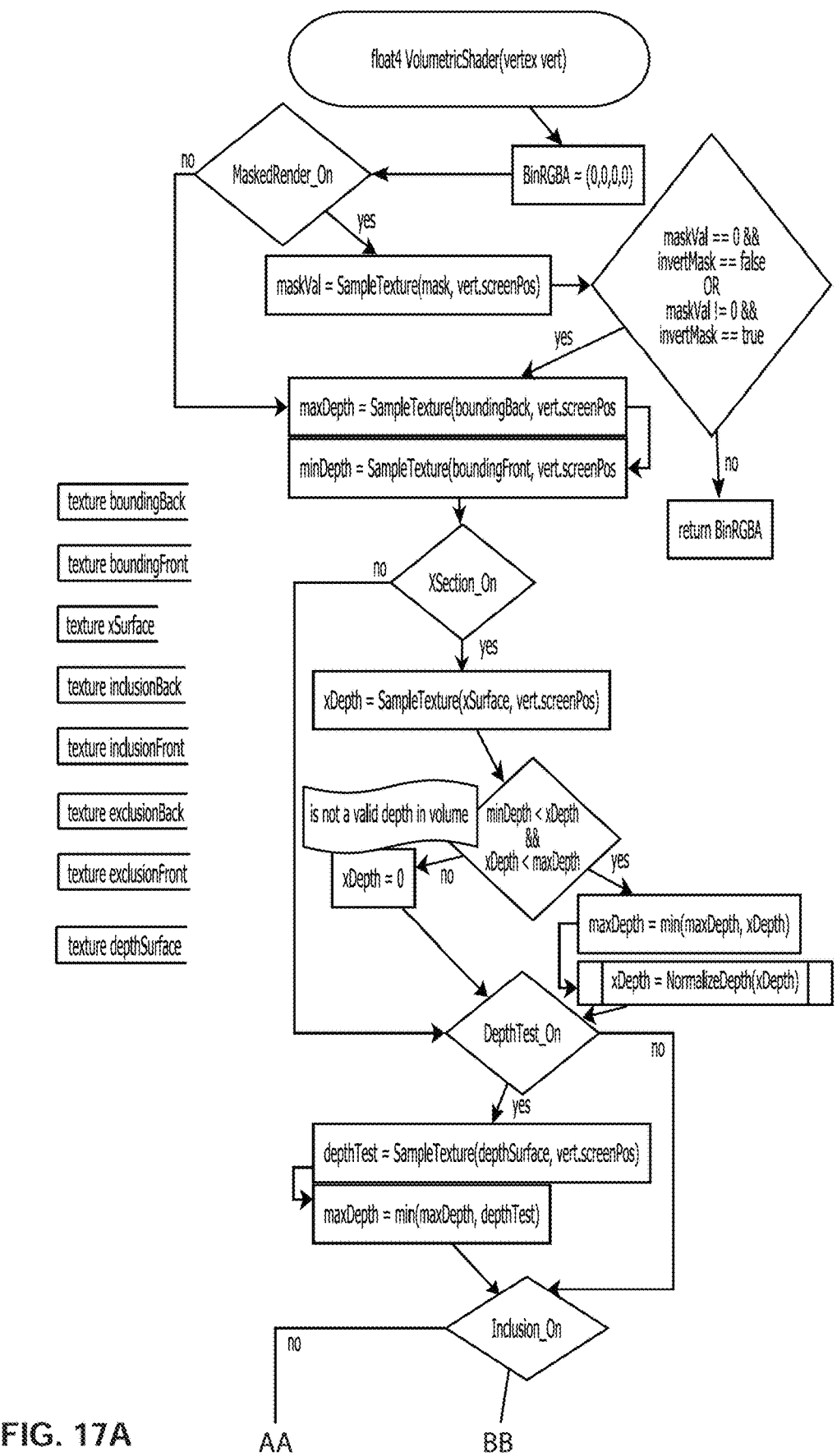
FIGS. 17A and 17B illustrate a flowchart describing an example method of shading a volume object rendered in an IMVR environment by an IMVR system, according to an embodiment.
Figure 17B:
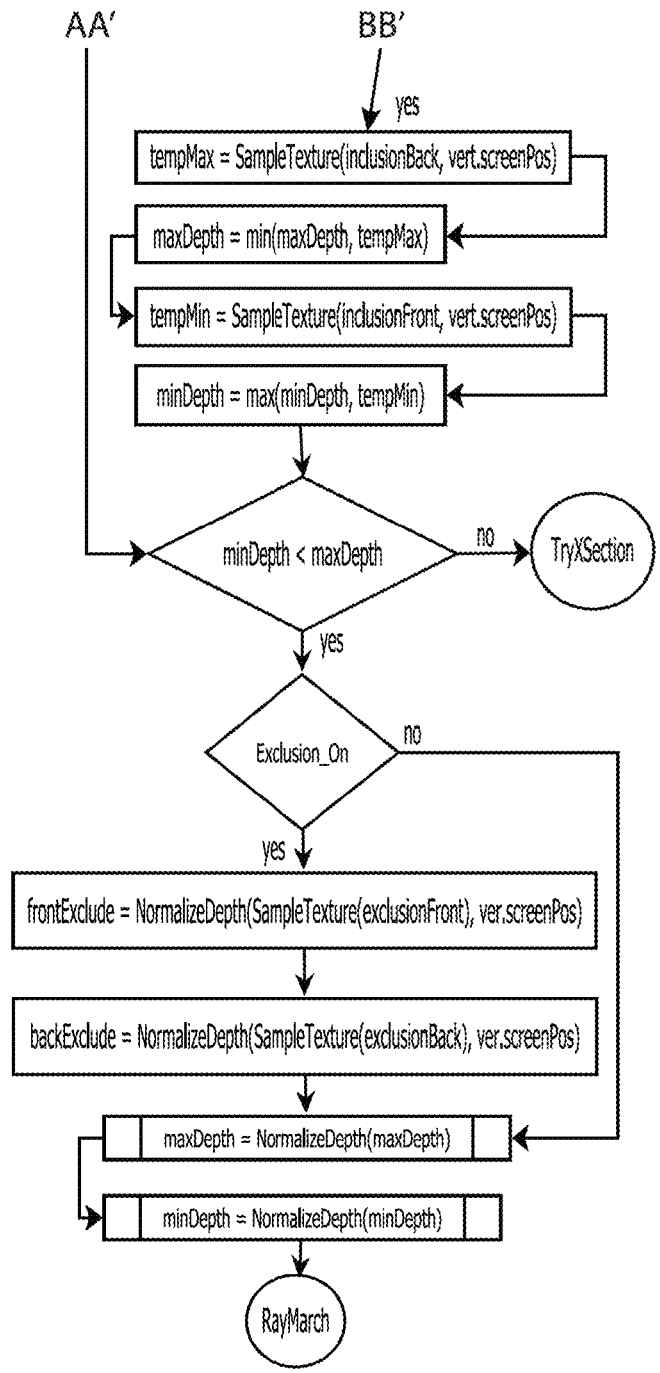
Figure 18:
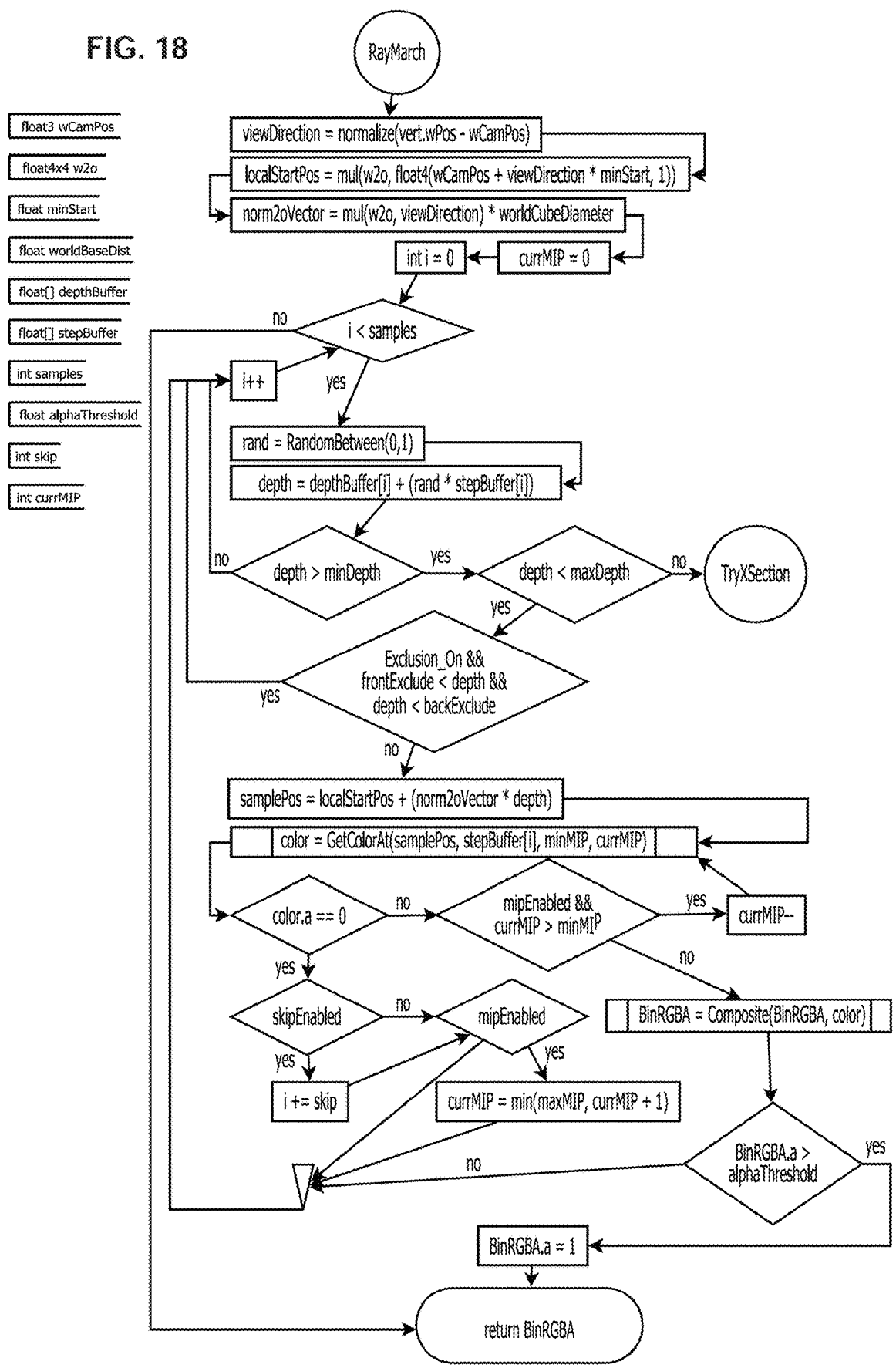
FIG. 18 is a flowchart describing an example method of rendering a volume object in an IMVR environment using a ray marching approach by an IMVR system, according to an embodiment.

FIG. 16 is a flowchart describing an example method of rendering a volume object, with sequence of events following the rendering described in FIG. 15, in an IMVR environment, according to an embodiment. FIGS. 17A and 17B illustrate portions of a method involving shading a texture associated with a volume object rendered in an IMVR environment, using a set of user inputs, using a renderer in an IMVR system according to an embodiment. The arrows AA and BB in FIG. 17A continue to arrows AA' and BB' in FIG. 17B. FIG. 18 is a flowchart describing an example method of rendering a volume object in an IMVR environment, using a ray marching approach, by a renderer in an IMVR system, according to an embodiment.

In some implementations an IMVR system can be configured to execute a foveated rendering or a masked rendering to better present a visualization of an instance of an object in an IMVR environment to a user. In some implementations the masked rendering can be implemented with binning. For example, such an approach can be used to enable a user to view a higher resolution in certain areas of the screen and decrease resolution in non-significant areas with the overall goal of increasing user experience. An example of this is to use eye tracking to render higher resolution where the user is looking (is foveated), this can permit increased frame rates of updating a rendering compared to attempting to render the entire screen at a high resolution. Binning is a method of treating multiple pixels as a single pixel while rendering, which achieves the lower resolution areas.

Figure 19A:
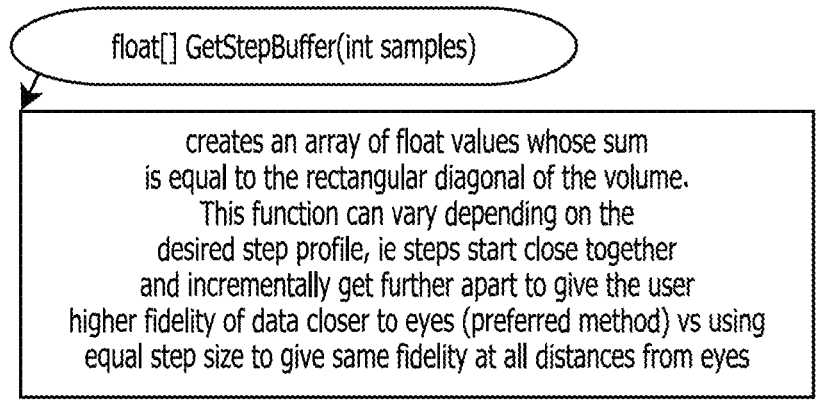
FIGS. 19A and 19B are flowcharts describing example methods of using a depth buffer to render an object in an IMVR environment based on a spatial position of a user, according to an embodiment.
Figure 19B:
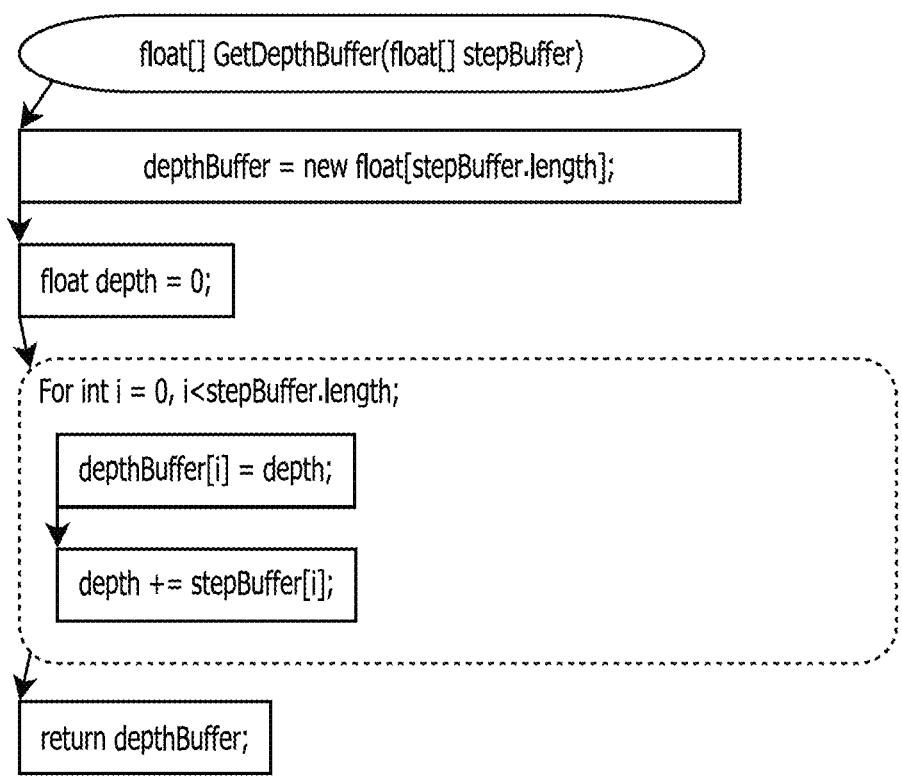

FIGS. 19A and 19B illustrate an example method of generating the sample distances and weights to be assigned to each of those samples used by the ray marching approach of FIG. 18.

Figure 20:
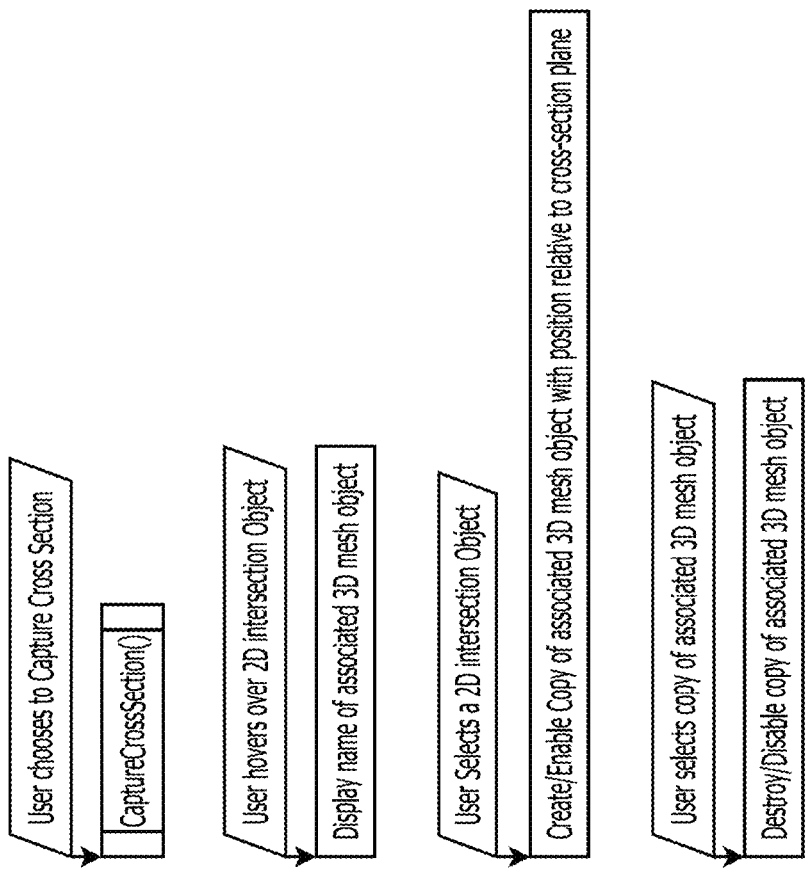
FIGS. 20 and 21 are schematic representations of a sequence of user actions related to a user's choice to capture a cross-sectional view of an IMVR environment, a user's access to a three dimensional mesh object associated with a volume object rendered in an IMVR environment, and the functions invoked in an IMVR system to implement the changes desired by the user's actions in the IMVR environment, according to an embodiment.

In some implementations, an IMVR system can be configured to use a data set that includes one or more artist rendered mesh objects. The IMVR system can be used to capture cross-sections of the mesh object using a set of tools including a cross-section tool provided to the user(s). FIG. 20 illustrates a set of user actions to invoke capturing a mesh object rendered in an IMVR environment. For example, in some implementations of an IMVR system, a user can select the functionality to enable capturing cross-sections via a user interface at a user device. The user can then hover over a two dimensional intersection object in the IMVR environment to display the name of an associated three dimensional mesh object. The user can select the two dimensional intersection object to create or enable a copy of the associated three dimensional mesh object with a position relative to a cross-section plane defined by the user. In some instances the user can select the three dimensional mesh object and destroy or disable the three dimensional mesh object/

Figure 21:
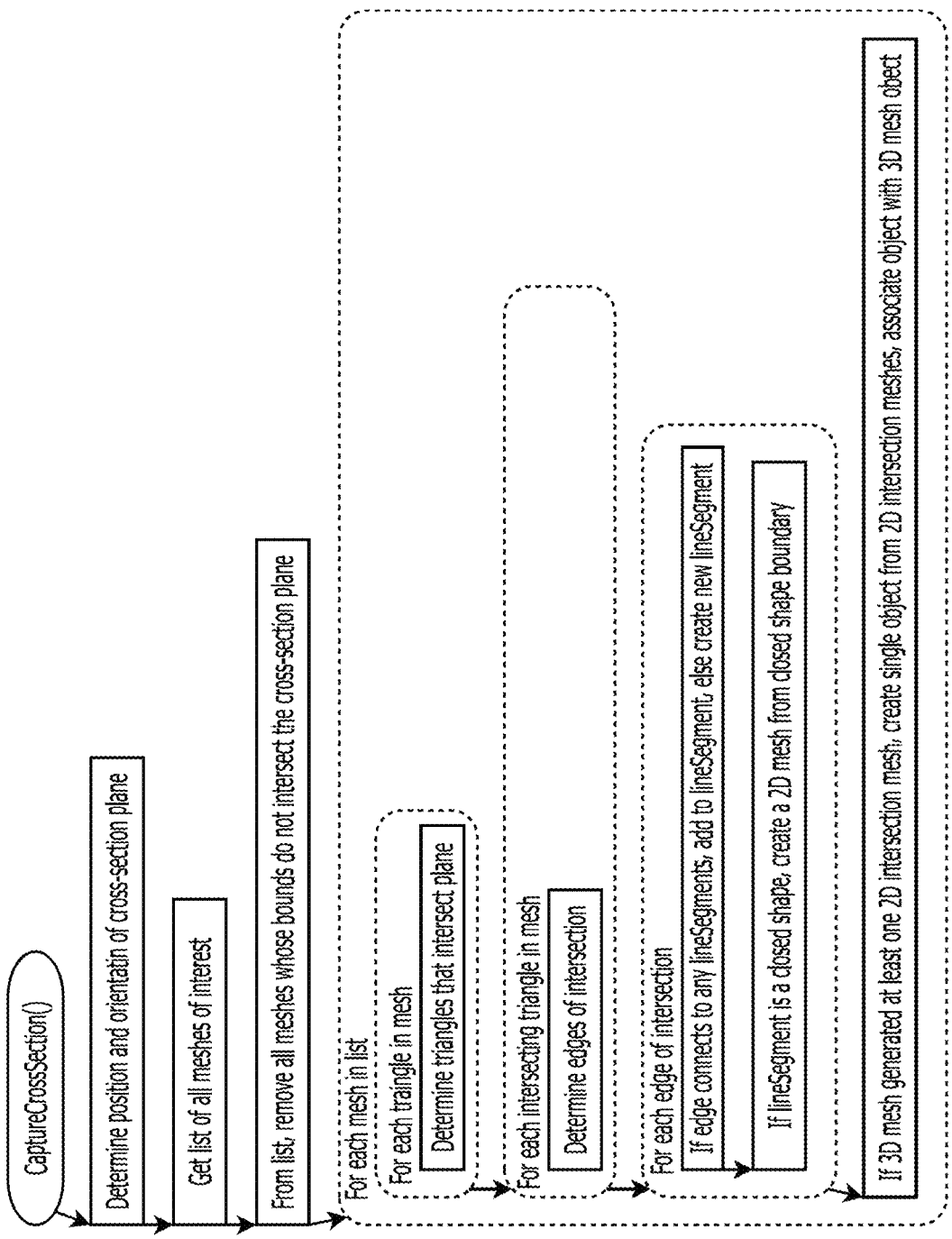

FIG. 21 is a flowchart describing an example method to capture a mesh object using a cross-section tool, according to an embodiment. For example, a renderer can be configured to determine a position and orientation of a cross-sectional plane. The renderer can generate a list of meshes of interest and from the list remove meshes whose bounds do not intersect with the sectional plane. For the remaining meshes in the list, the renderer can list triangles in a mesh and for each triangle determine whether that triangle intersects with the sectional plane. If it does, based on the determination, the renderer then determines the edges of intersection. For each edge of intersection, if the edge connects to any line segments the renderer adds to the line segment (if not it creates a new line segment). If the line segment is of a closed shape it creates a 2D mesh from the closed boundary. The renderer carries out this procedure iteratively for all edges and all meshes in the list until it creates a three dimensional mesh. It creates a single object from the 2D intersection meshes and associates the object with the three dimensional mesh object, which is retuned as the captured mesh cross-section.

Figure 22:
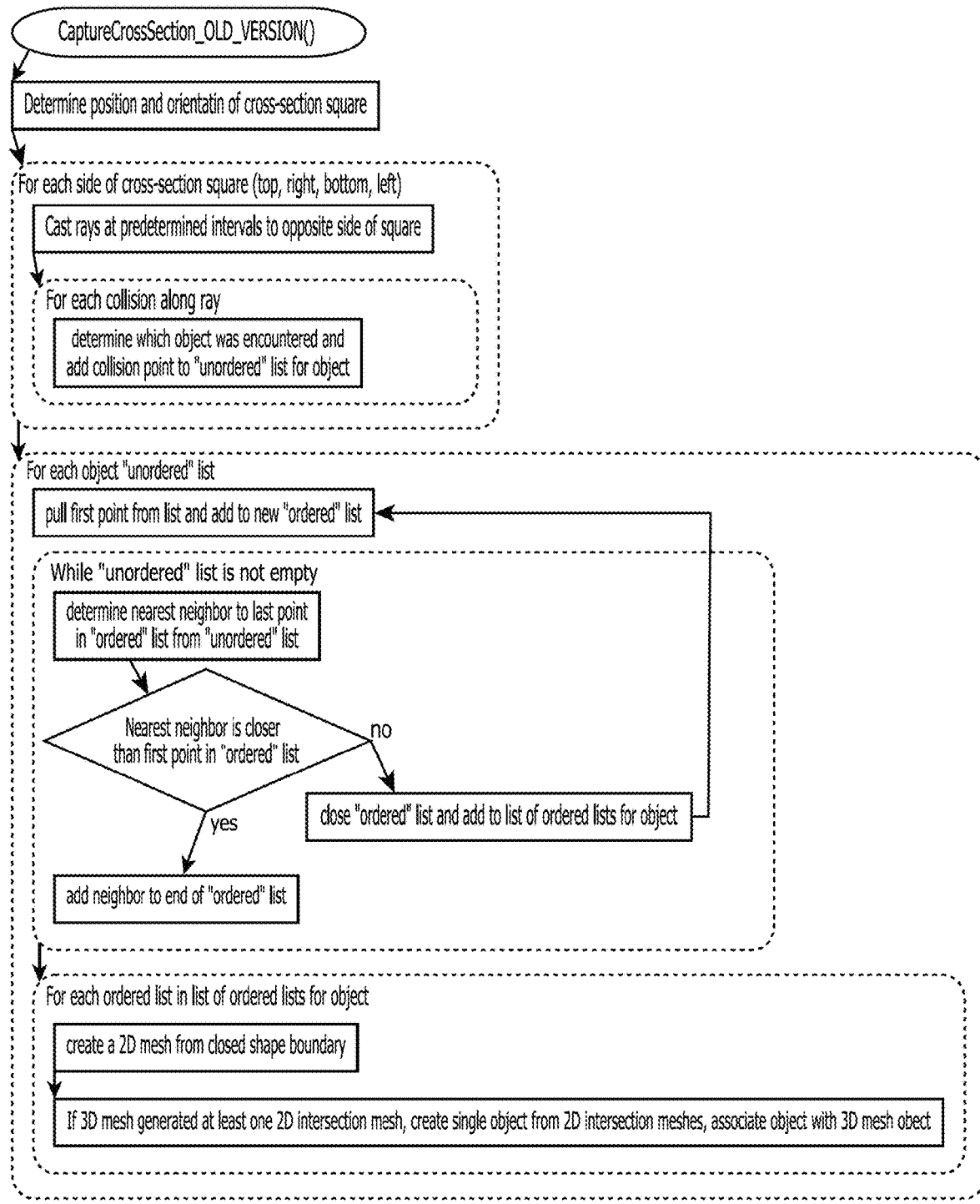
FIG. 22 is a flowchart describing an implementation of capturing a cross-sectional view of an object in an IMVR environment, according to another embodiment.

FIG. 22 illustrates another example method to capture a cross-section in a mesh-object rendered in an IMVR environment using another cross-section tool, according to another embodiment. According to this method, a resolution is chosen and position and orientation of a cross-sectional square are determined. For each side of the cross-section, square rays are cast at predetermined intervals to the opposite side. For each collision along a ray the object encountered is determined and collision point is added to a list to return a cloud of points. The renderer then generates an ordered list and calculated for each point a nearest neighbor is determined from the unordered list. If the nearest neighbor is closer than the first point in the ordered list the neighbor is added to the ordered list. For each ordered list a two dimensional mesh is generated from a closed shape boundary. If three-dimensional mesh generated at least one 2D intersection, the renderer creates a single object from the 2D intersection meshes and associates the object with the 3D mesh object. In some instances, a renderer can use a triangulator to generate a surface by creating triangles to make the surface.

In some implementations mesh objects can be used to create ghosts, also known as ghosting. For example, a renderer can make a copy of an object that a two dimensional mesh is made for. The renderer can put back a mesh in association with a three dimensional data set including volume objects but store the mesh in an off state. It can be configured to switch to being active and visible when turned on and the three dimensional object is turned off.

Figure 23:
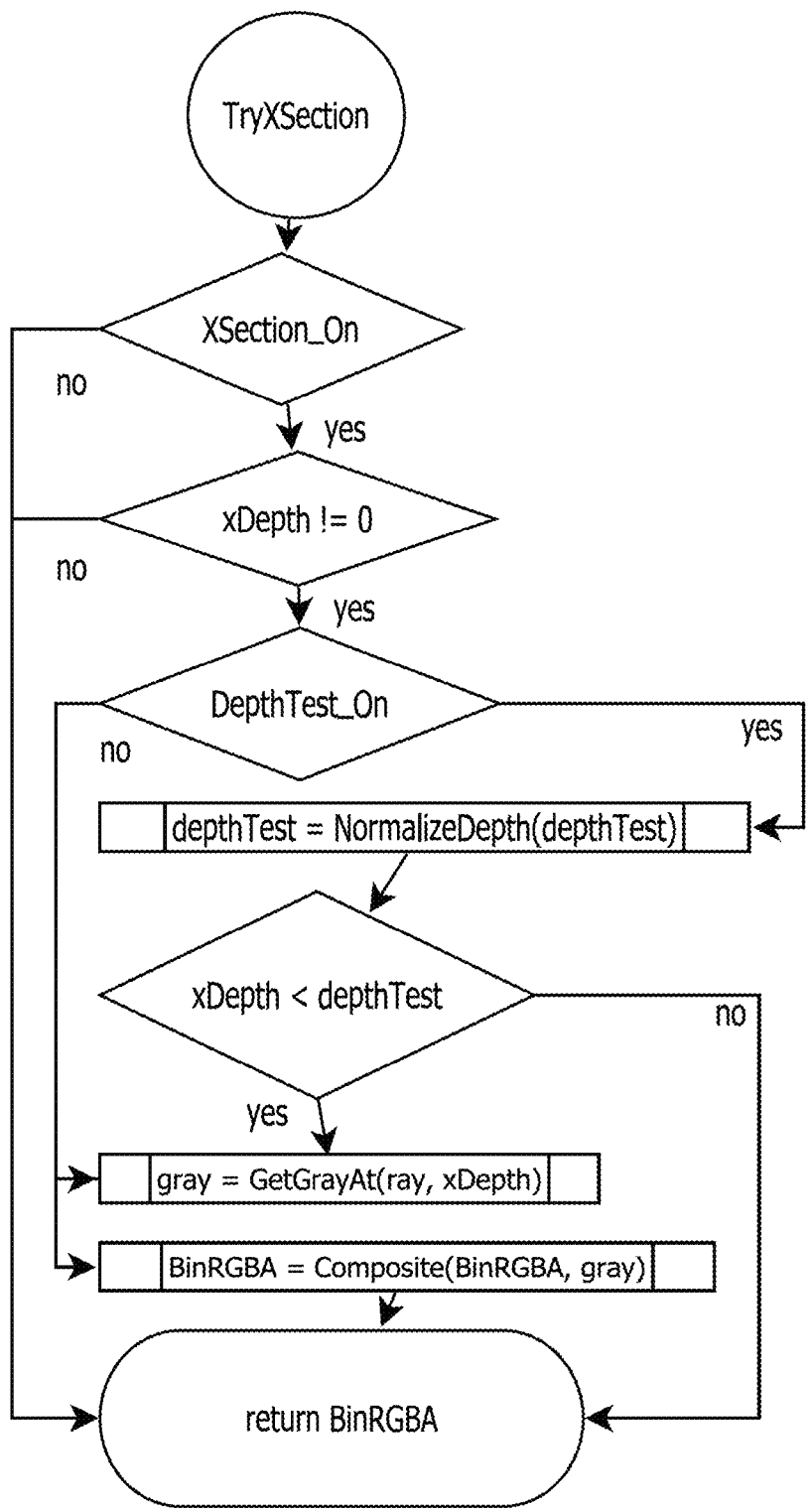
FIG. 23 is a flowchart describing an implementation of capturing a cross-sectional view of an object in an IMVR environment, according to another embodiment.

The cross-section tool can be used to take a cross-section, at any angle, through a mesh model data. This creates a 2D representation of the intersections. This cross-section is interactable. The user can point at structures and have a label appear, as well as click on the structures and have the full structure pop-out of the cross-section. For example, a cross-section can be taken through the chest and a user can pop-out the aorta to visualize how it courses superior in the thorax and then inferior to the abdomen. This usability gives the user detailed information on the course of structures above and below the given plane, which is valuable for studying medical imaging. FIG. 23 is a flowchart describing an example implementation of a cross-section tool in an IMVR system.

In some implementations of an IMVR system, the one or more users can be provided with an additional set of tools to manipulate the rendered instance of the object. Some example tools can include Volume Scaling, Exclusion and/or Inclusion tools configured to isolate a volume of interest by excluding or including portions of an instance of the object rendered, cross-section tool configured to section a volume object along any arbitrary plane intersecting with the object. Some other examples include Voxel painter and Voxel Eraser tools and Counting/Labeling tools configured to allow a user to annotate an instance of a render object, Mesh creating tools and measurement tools.

A measurement tool, as an example, can be configured to give a user the ability to take accurate measurements within volumetric data sets. The user can draw lines, either freehand or point-to-point, which can then be labeled with an accurate measurement. For example, the diameter of an aorta from an angiogram could be measured or the distance between two cells from confocal microscopy data. Additionally, in some implementations there can be a feature allowing the user to move individual line vertices from already created lines. In some implementations, the user can also add or delete vertices.

Figure 28:
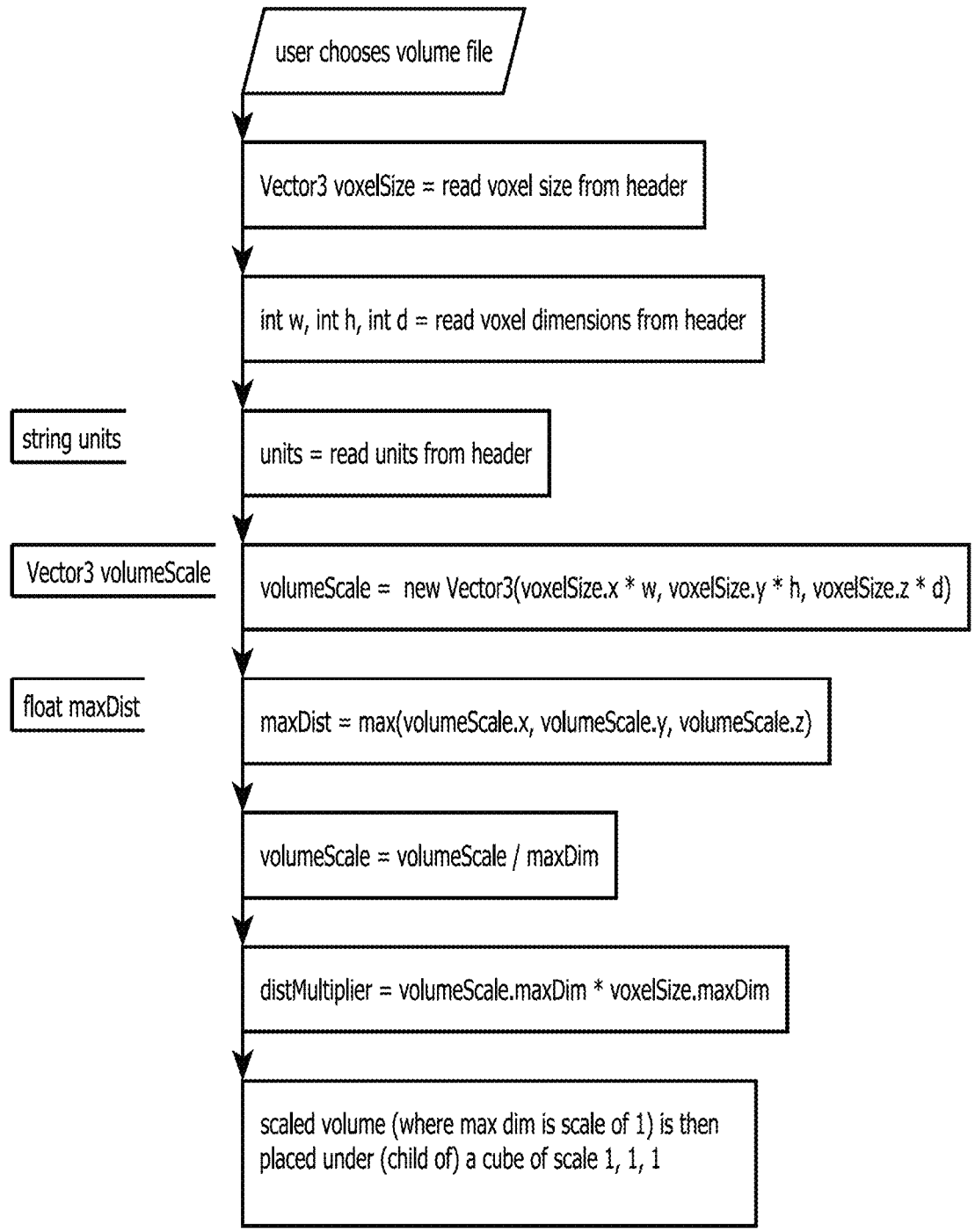
FIG. 28 is a flowchart describing an example method of generating a scaled volume representation of an object in an IMVR environment, using an IMVR system, according to an embodiment.
Figure 34:
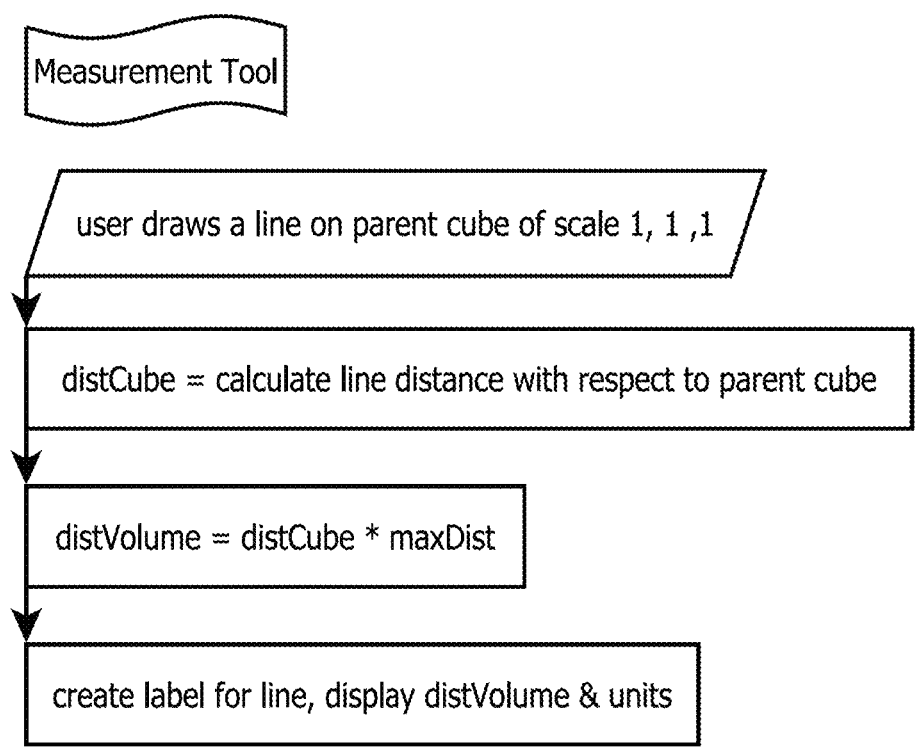
FIG. 34 is a flowchart describing an example method of annotating a representation of an object in an IMVR environment using an annotating tool in an IMVR system, according to an embodiment.
Figure 35:
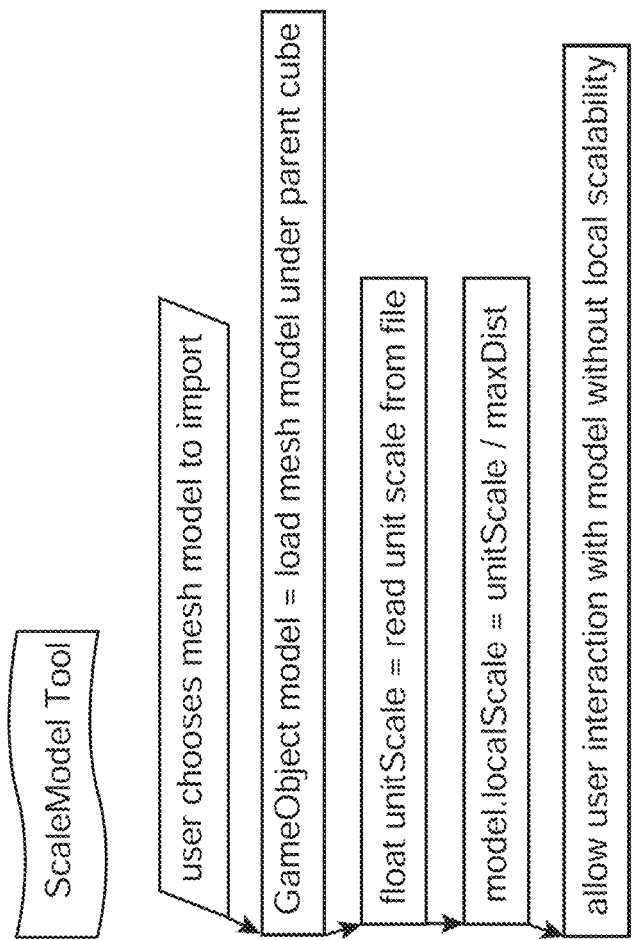
FIG. 35 is a flowchart describing an example method of generating and using a scaled mesh model representation object in an IMVR environment using an IMVR system, according to an embodiment.

FIG. 28 is a flowchart describing an example method to scale a volume of an instance of a rendered object using a volume scaling tool. A renderer can implement the flowchart in FIG. 28 to render based on a scaling factor calculated based a set of user inputs and/or sampling information associated with a user device. For example, a renderer can receive information associated with a voxel size, and voxel dimensions of a data file, and scale the object associated with the data set by a predetermined factor, based on a generated scale vector. FIGS. 29A, 29B, and 30 are flowcharts describing example methods of using an Exclusion, Inclusion and Cross Section tool, respectively. FIGS. 31A-31C, 32A, 32B, 33A, 33B, 34 and 35 are flowcharts describing example methods of implementing additional example tools to manipulate an instance of an object rendered in an IMVR environment. For example, as shown in FIG. 34, a measurement or annotation tool can be used to allow a user to draw a line and label the line as an annotation.

In some instances a user may measure a portion of a rendered object and label the portion with a measurement annotation (e.g. a measurement annotation indicating a scale of a portion of an object). The IMVR system can be configured such that the annotation can be propagated to other users of an IMVR session. The IMVR system can also allow the user to associate the annotation into a portion of a rendered instance of an object and save the instance to send it to other users at a later time point.

In some implementations of an IMVR system one or more user(s) can be provided a set of tools to manipulate objects rendered in the IMVR environment. For example users can bring object closer, magnify, shrink, pivot, turn, nudge, and/or perform any other suitable manipulation to an object. In some instances, users can make objects that are otherwise static be mobilized with user actions. For example users can use one or more hand controllers controlled by each user to throw, catch, roll, and/or initiate a pull in of objects. IMVR system can be configured to modify mobility laws of objects and users in the IMVR environment in any suitable way. As an example, a user can select an object and pull it closer or push it further away by directing the controller joystick. The speed of the moving object can be a function of its distance from the controller. For example, the IMVR system can be configured such that a faraway object moves quickly and slows down as it gets closer to the user in the IMVR environment. An example fishing pole tool can be configured to allow a user controlled device (e.g., a fishing pole) to intersect with object and pull up the object at rate proportional to distance. As another example the IMVR system can be configured such that a when a user tosses an object it coasts, slowly losing momentum before coming to a stop. The user's control can then be released from the tossed object and another user may pick it the tossed object up. An IMVR system can be configured to allow object magnification using two controllers. For example, a user can point at an instance of an object renderer, can grab or select the object using one action and drag using another. For example, the renderer can function such that when the user pulls a trigger associated with a controller, the object gets attached to a pointer and the object can rotate with the user's controller or hand even after the user lets go of a trigger. The last manipulatable object can have a lasting association with the hand controller. Two controllers can be used to double grip the last selected object and a user can pull hands apart or together to expand or contract. The renderer can calculate a distance between the controllers and scale the object based on change in distance while using a fixed center point on the object being scaled. The fixed center point can be any point of interest and upon zooming in, for example, a user can focus on the magnified region without recentering. The user can also rotate the object while changing magnification.

Some embodiments use one or more digital anatomical models and neuroanatomical connection data to render an interactive, functionally representative model of the human nervous system. By rendering simulated neurons that respond visually to the activity of other representative neurons as well as damaging "lesion" objects, such embodiments can convey to users the spatial relationship of the signal pathway, directionality, and/or functional state of a neuroanatomical circuit. For example, if a user places a "lesion" object or other representation of neurologic damage into the neuroanatomical model, the representative system can respond to the interruption of the neurons affected and display a specific representation of the functional loss experienced by a patient. By utilizing multi-user connectivity, such embodiments allow users from the same or distant locations, to be represented by digital avatars in the same common interactive environment, and interact with the same objects in real-time. To increase the ability to diagram and teach in a multi user environment, tools can be provided to users allowing them to create three-dimensional line-drawings anchored to objects in the virtual environment, for example, allowing an instructor to conduct and record lectures using drawings and diagrams in three dimensions while in the IMVR environment. In some embodiments, features disclosed can be utilized to increase a student's intuitive understanding of cross section based medical imaging techniques and the disclosure can be configured to provide two-dimensional cross-sections from any three-dimensional object present in the IMVR environment, allowing user(s) (e.g., students) to simulate the creation of CT and MRI imaging while maintaining the ability to reference the three-dimensional objects that are represented on the cross section. Embodiments not only provide for and/or facilitate real-time interactions (e.g., students and an instructor), the teachings of the disclosure also enable creation of self-contained modules. User interactions and created drawings or cross sections can be recordable/recorded to a transmittable save file. This can be represented as a virtual instructor performing the actions and didactic instruction originally recorded from the instructor. Such an embodiment allows a student user to review content outside of normal instruction periods, and at their own pace. In addition to the cross section based medical imaging noted above, the system is capable of importing DICOM images such as computed tomography (CT), magnetic resonance imaging (MRI), Positron emission tomography-computed tomography (PET-CT), and/or initiation of Magnetoencephalography (MEG) data, as well as one or more other data sources. This information is imported through various software processes and analyzed through bespoke mathematical systems and methods that render the images in virtual reality. Additionally, some embodiments provide for pseudosegmentation of systems (e.g., vascular, bone, tissue), through an innovative transfer function that allows a user to look at data (densities) of interest while dropping off data of no interest. In some implementations, this can provide a clinician/user the ability to highlight or bring to the forefront structures and systems for closer analysis in real time. An opaque plane can be inserted into the volume to display data similar to traditional 2-D images. A user can adjust the transparency embedded in the transfer function to visualize structures as they emerge from the opaque plane. Additionally, some embodiments provide for multi-user interaction in a VR/AR environment. As users do not have to be located in the same location, such embodiments allow for clinical discussions from anywhere in the world with a high-speed network.

Figure 51A:
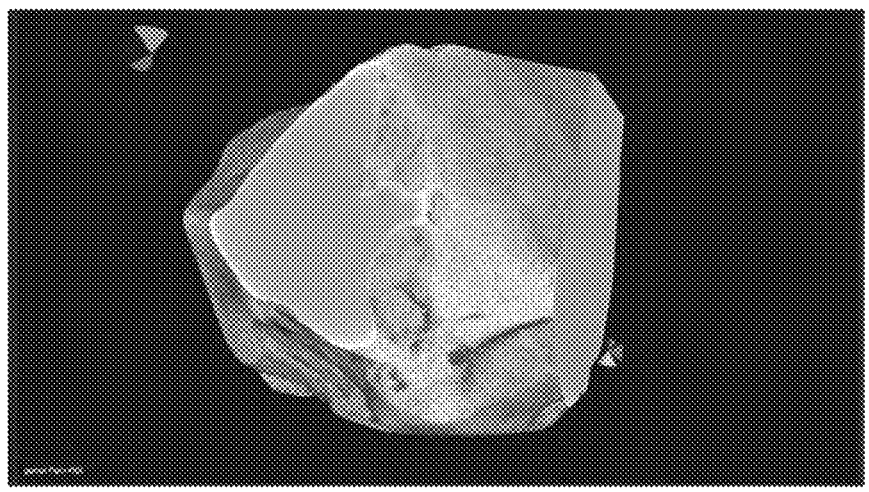
FIGS. 51A-51C illustrate an example embodiment of an IMVR system used for volumization and visualization of gemstones and/or metals, using a spatial data series obtained via CT, according to an embodiment.
Figure 51B:
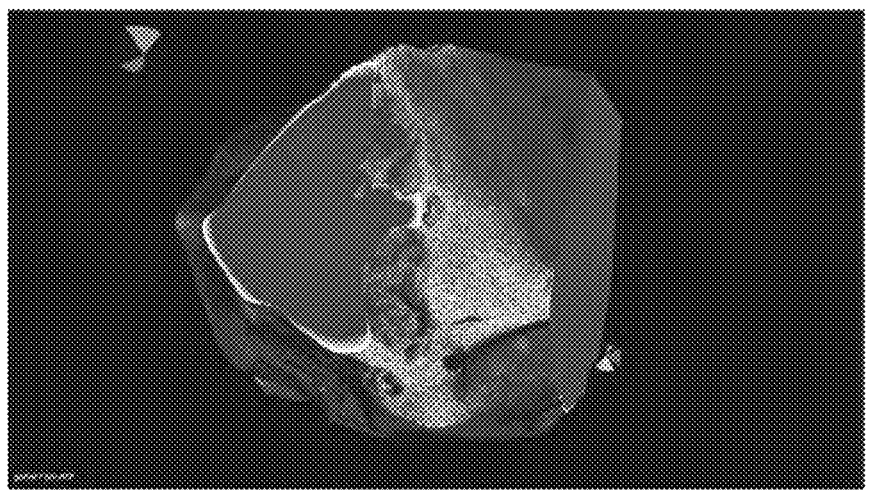
Figure 51C:
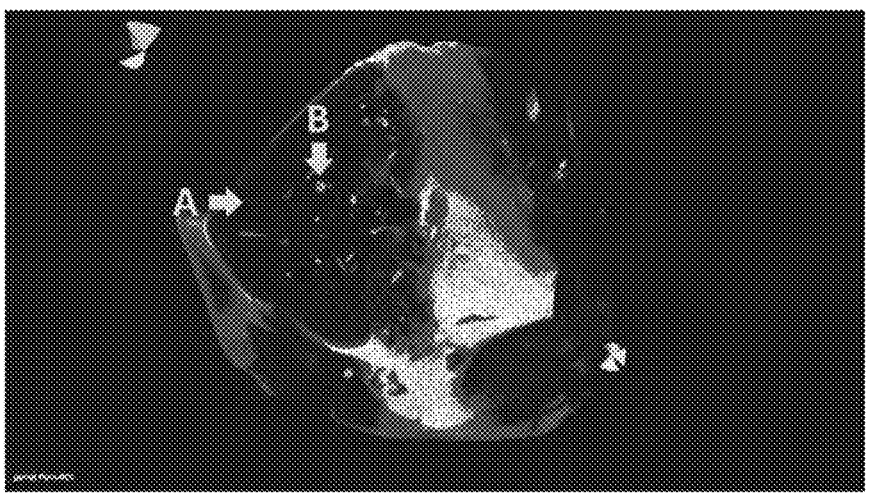

As described above, the IMVR system(s) described above can be used to visualize any spatial data series associated with any object from any field of inquiry. FIGS. 51A-51C illustrate an example embodiment of an IMVR system used for volumization and visualization of gemstones and/or metals, using a spatial data series obtained via CT. FIG. 51A is an image of garnet stone obtained via a CT scan that allows an inspection of inclusion bodies and crystal structure of the stone. FIG. 51B is a colorized rendering of the garnet stone in an IMVR environment. FIG. 51C is a structural view of the garnet stone of FIGS. 51A and 51B, volumized and rendered in an example IMVR environment by an IMVR system according to an embodiment, to show a crystal structure A and an inclusion body B, labeled in FIG. 51C.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In this disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various inventive embodiments have been described and illustrated herein, and it should be understood that a variety of other tools, components, elements, means, and/or structures for performing the function(s) and/or obtaining the result(s) and/or one or more of the advantages described herein, and each of such variations and/or modifications is deemed to be within the scope of the embodiments described herein. Moreover, it is to be understood and appreciated that all parameters, dimensions, materials, and configurations described herein are meant to be exemplary and that the actual parameters, dimensions, materials, and/or configurations can depend upon the specific application or applications for which the embodiments of the disclosure are utilized and/or applied. Those of skill will recognize and/or be able to ascertain using no more than routine experimentation, many equivalents to the specific novel implementations and embodiments described herein. It is, therefore, to be understood that the foregoing embodiments are presented by way of example only and that, within the scope of the disclosed embodiments and equivalents thereto, embodiments may be practiced otherwise than as specifically described and/or illustrated. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments can be implemented in any of numerous ways. For example, the embodiments may be implemented using hardware, software, or a combination thereof. When implemented in software, the software code can be executed on any suitable processor or collection of processors, provided in any of numerous ways.

Further, it should be appreciated that the present disclosure can be used in conjunction with other systems, including medical imaging systems, surgical systems, treatment systems, data processing systems, any of which can be embodied in any of a number ways. Embodiments include methods and apparatuses for efficiently rendering and updating interactive multiuser virtual reality environment that can be served to multiple users via multiple user devices connected within a multiuser VR system. As used herein, in some embodiments, VR systems can include augmented reality (AR) systems. The disclosure includes novel and advantageous methods, systems and apparatuses for rendering, managing, recording, and replaying interactive multiuser VR/AR presentations and experiences, including medical/surgical data, multi-dimensional data transformed for VR/AR, and can include real-time and/or near real-time data, visual data including images, video, audio, streaming media, CT data, MRI data, EEG data, MEG data, and/or the like. In some implementations, some or all of the multi-dimensional data is near real-time or real time, and interactions between multiple users can similarly be coordinated to take advantage of such improvements, for example, during surgery or teaching. Embodiments can be configured to reduce bandwidth required when multiple users are interacting and manipulating data in a shared VR/AR environment. By way of example, teachings of the disclosure can be integrated with the teachings of US Pat. App. Pub. Nos. 2013/0245461 and/or 2016/0191887, and/or U.S. Pat. No. 6,256,529, the entirety of each being herein expressly incorporated by reference for all purposes.

Various methods and/or processes outlined herein can be coded as software that is executable on one or more processors that employ any one of a variety of operating systems or platforms. Additionally, such software can be written using any of a number of suitable programming languages and/or programming or scripting tools, and also can be compiled as executable machine language code or intermediate code that is executed on a framework or virtual machine.

In this respect, various disclosed concepts can be embodied as a non-transitory computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers/compute device and/or other processors to implement various aspects of the present disclosure as discussed above.

The terms "program" or "software" are used herein in a general sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure can be distributed in a modular fashion amongst a number of different compute devices/processors to implement various aspects of the disclosure.

Processor-executable instructions can be in many forms, such as program modules, executed by one or more compute devices, and can include routines, programs, objects, components, data structures, etc. that perform particular tasks or implement particular data types, and the functionality can be combined and/or distributed as appropriate for various embodiments.

Data structures can be stored in processor-readable media in a number of suitable forms. For simplicity of illustration, data structures may be shown to have fields that are related through location in the data structure. Such relationships can likewise be achieved by assigning storage for the fields with locations in a processor-readable medium that conveys relationship(s) between the fields. However, any suitable mechanism/tool can be used to establish a relationship between information in fields of a data structure, including through the use of pointers, tags or other mechanisms/tools that establish relationship between data elements.

Various disclosed concepts can be embodied as one or more methods, of which examples have been provided. The acts performed as part of a particular method can be ordered in any suitable way. Accordingly, embodiments can be constructed in which acts are performed in an order different than illustrated/discussed, which can include performing some acts simultaneously, even though some are shown as sequential acts in illustrative embodiments.

All definitions, as defined and used herein, should be understood to control over dictionary definitions, definitions in documents incorporated by reference, and/or ordinary meanings of the defined terms.

The use of flow diagrams is not meant to be limiting with respect to the order of operations performed. The herein described subject matter sometimes illustrates different components contained within, or connected with, different other components. It is to be understood that such depicted architectures are illustrative examples, and that in fact many other architectures can be implemented in accordance with the teachings herein to achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

The indefinite articles "a" and "an," as used herein, unless clearly indicated to the contrary, should be understood to mean "at least one."

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in claims, shall have its ordinary meaning as used in the field of patent law.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," "composed of" and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
a volatile memory;
a non-volatile memory;
a first processor operatively coupled to the non-volatile memory, the first processor configured to receive a data set associated with an object and user information associated with a first spatial position of a first user with reference to the object and in a virtual environment, the data set including a spatial data series of the object,
the first processor configured to receive a set of inputs from the first user, the set of inputs being associated with a set of predetermined properties associated with a portion of the object; and
a second processor operatively coupled to the volatile memory, the second processor configured to render, based on the user information and the set of inputs, a first instance of the portion of the object in the virtual environment, the first instance of the portion of the object being from a first perspective of the first user, the first perspective being based on the first spatial position of the first user,
at least one of the first processor or the second processor configured to generate a data package associated with the object and transmit the data package to a user device associated with a second user such that a second instance of the portion of the object can be rendered at the user device associated with the second user,
the second processor configured to receive manipulation information related to a manipulation of the first instance of the portion of the object by the first user, the second processor configured to render, based on the manipulation information, an updated first instance of the portion of the object that manifests an effect of the manipulation in the virtual environment,
at least one of the first processor or the second processor configured to generate an updated data package including the manipulation information and transmit the updated data package to the user device associated with the second user such that an updated second instance of the portion of the object can be rendered at the user device associated with the second user, the updated second instance of the portion of the object manifesting the effect of the manipulation,
at least one of the first processor or the second processor configured to record media associated with the rendering of the updated first instance of the portion of the object, the media including spatial information associated with the rendering of the updated first instance of the portion of the object from the first perspective of the first user, the media being configured to be replayed to render the updated first instance of the portion of the object from a second perspective of the second user at a second spatial position and different than the first perspective of the first user.

2. The apparatus of claim 1, wherein the manipulation information is first manipulation information related to a first manipulation by the first user, the effect of the first manipulation is a first effect, the updated first instance of the portion of the object is a first updated first instance of the portion of the object, and the updated data package is a first updated data package, the first processor further configured to:
receive, from the user device associated with the second user, a second updated data package including second manipulation information related to a second manipulation of the second instance of the portion of the object, the second manipulation being made by the second user and related to a second effect manifest at the user device associated with the second user, and
at least one of the first processor or the second processor configured to render, based on the second manipulation information, a second updated first instance of the portion of the object that manifests the second effect of the second manipulation.

3. The apparatus of claim 1, wherein:
at least one of the first processor or the second processor is configured to receive a set of measurement inputs from the first user and based on the set of measurement inputs, add a measurement annotation to the data set such that the measurement annotation is presented with a rendering of the first instance of the portion of the object,
the updated data package including the data set and including the measurement annotation, the updated second instance of the portion of the object including a presentation of the measurement annotation.

4. The apparatus of claim 1, wherein the spatial data series includes a series of multi-dimensional data including images or point-cloud data collected using at least one of Computed Tomography (CT), Magnetic Resonance Imaging (MM), Positron Emission Tomography, Confocal Imaging, Light Microscopy, Electron Microscopy, Electroencephalography (EEG), Magnetocardiography (MCG), or Magnetoencephalography.

5. The apparatus of claim 1, wherein at least one of the first processor or the second processor is configured to:
receive, from the first user, instructions related to sharing of the data package,
transmit, in chunks and based on the instructions, the data package to the user device associated with the second user such that a portion of the data package is stored in a volatile memory associated with the user device associated with the second user for a period of time and not stored in a non-volatile memory associated with the user device associated with the second user, to render the second instance of the portion of the object at the user device associated with the second user, and, after the period of time, the portion of the data package is erased from the volatile memory associated with the user device associated with the second user.

6. The apparatus of claim 1, wherein the set of predetermined properties includes a transparency property and a color property, and the set of inputs include a set of keys, each key from the set of keys configured to provide information including a first value associated with the transparency property and a second value associated with the color property, the second processor configured to interpolate the information obtained from each key from the set of keys to generate a look-up-table.

7. The apparatus of claim 1, wherein the data package is a first data package and at least one of the first processor or the second processor is configured to:
generate a second data package associated with the object,
receive, from the first user, instructions related to sharing of the second data package, the instructions including an authorization from the first user and to a third user to store the second data package in a non-volatile memory associated with a user device associated with the third user, transmit, in chunks and based on the instructions, the second data package and the authorization to the user device associated with the third user such that a portion of the second data package is stored in a volatile memory associated with the user device associated with the third user for a period of time and also stored in a non-volatile memory associated with the user device associated with the third user, to render a third instance of the portion of the object at the user device associated with the third user, and, after the period of time and based on the authorization, the portion of the second data package is erased from the volatile memory but not erased from the non-volatile memory.

8. A non-transitory processor-readable medium storing code representing instructions to be executed by a processor, the code comprising code to cause the processor to:

receive data including medical images associated with an object;

extract a data set associated with a structure of the object and user information associated with a first spatial position of a first user with reference to the object in a virtual environment;

receive a set of inputs from the first user, the set of inputs being associated with a set of predetermined properties associated with a portion of the object in the virtual environment;

render, based on the set of inputs and the user information, a first instance of the portion of the object in the virtual environment from a first perspective of the first user, the first perspective being based on the first spatial position of the first user;

generate a data package associated with the object;

transmit the data package to a user device associated with a second user such that a second instance of the portion of the object can be rendered at the user device associated with the second user;

receive manipulation information related to a manipulation of the rendered first instance of the portion of the object by the first user and in the virtual environment;

render, based on the manipulation information, an updated first instance of the portion of the object that manifests an effect of the manipulation in the virtual environment;

generate an updated data package including the manipulation information;

transmit the updated data package to the user device associated with the second user such that an updated second instance of the portion of the object can be rendered at the user device associated with the second user, the updated second instance of the portion of the object manifesting the effect of the manipulation; and record media associated with the manipulation and the rendering of the updated first instance of the portion of the object, the media including spatial information associated with the rendering of the updated first instance of the portion of the object, from the first perspective of the first user, the media being configured to be replayed to render the updated first instance of the portion of the object from a second perspective of the second user at a second spatial position different than the first perspective of the first user at the first spatial position.

9. The non-transitory processor-readable medium of claim 8, wherein the set of predetermined properties includes at least one of transparency, position, viewability, and color, and the set of inputs includes a set of keys, each key from the set of keys configured to provide a value associated with a predetermined property from the set of predetermined properties, the code to cause the processor to render the first instance of the portion of the object includes code to cause the processor to interpolate the information obtained from each key from the set of keys to generate a look-up-table associated with the predetermined property from the set of predetermined properties, the rendering the first instance being based on the look-up-table.

10. The non-transitory processor-readable medium of claim 8, the code further comprising code to cause the processor to:

receive a set of annotation inputs from the first user;

display, with the first instance of the portion of the object and based on the annotation inputs, an annotation associated with the portion of the object;

generate an updated data set, the updated data set including the annotation incorporated in association with the portion of the object such that the annotation is presented with a rendering of the portion of the object; and save the updated data set in a non-volatile memory associated with the processor.

11. The non-transitory processor-readable medium of claim 8, wherein the data package is a first data package the code further comprising code to cause the processor to:

generate a second data package associated with the object;

receive, from the first user, instructions related to sharing of the second data package;

transmit, in chunks, the second data package to a user device associated with a third user such that a portion of the second data package is stored in a volatile memory associated with the user device associated with the third user and not stored in a non-volatile memory associated with the user device associated with the third user for a period of time to render a third instance of the portion of the object at the user device associated with the third user, and, after the period of time, the portion of the second data package is erased from the volatile memory associated with the user device associated with the third user.

12. The non-transitory processor-readable medium of claim 8, wherein the data set includes spatial data obtained via a spatial data series collected using at least one of Computed Tomography (CT), Magnetic Resonance Imaging (MRI), Positron Emission Tomography, Confocal Imaging, Light Microscopy, Electron Microscopy, Electroencephalography (EEG), Magnetocardiography (MCG), or Magnetoencephalography.

13. The non-transitory processor-readable medium of claim 8, wherein the rendering the first instance of the portion of the object includes defining a measure of a level of completion, the code further comprising code to cause the processor to:

present a set of controls configured to facilitate the manipulation of the first instance of the portion of the object;

determine the measure of the level of completion of the rendering of the first instance to be below a threshold value; and set, based on the determining, the set of controls at an inactive state such that the manipulation information from the first user cannot be received via the set of controls.

14. The non-transitory processor-readable medium of claim 8, the code further comprising code to cause the processor to:
- receive device information associated with the processor, the device information including sampling information; and
- define a scaling factor based on the sampling information, the rendering of the updated first instance of the portion of the object being based on the scaling factor.

15. The non-transitory processor-readable medium of claim 8, the code further comprising code to cause the processor to:
- receive permission information associated with the data; and
- store, based on the permission information, the data in a non-volatile memory associated with the processor.

* * * * *